(12) United States Patent
Kanehira et al.

(10) Patent No.: US 7,329,257 B2
(45) Date of Patent: Feb. 12, 2008

(54) MEDICAL TREATMENT INSTRUMENT

(75) Inventors: Eiji Kanehira, Kanazawa (JP); Koji Iida, Sagamihara (JP); Naomi Sekino, Hachioji (JP); Makoto Inaba, Kunitachi (JP); Norihiko Hareyama, Hachioji (JP); Taisuke Sato, Hachioji (JP); Kenichi Kimura, Hachioji (JP); Hideto Yoshimine, Hachioji (JP)

(73) Assignee: Olympus Optical Co., Ltd., Tokyo (JP)

( * ) Notice: Subject to any disclaimer, the term of this patent is extended or adjusted under 35 U.S.C. 154(b) by 111 days.

(21) Appl. No.: 10/654,178

(22) Filed: Sep. 3, 2003

(65) Prior Publication Data

US 2004/0078035 A1   Apr. 22, 2004

Related U.S. Application Data

(63) Continuation-in-part of application No. 09/793,431, filed on Feb. 26, 2001, now abandoned, which is a continuation-in-part of application No. 09/488,732, filed on Jan. 20, 2000, now abandoned.

(30) Foreign Application Priority Data

| Jan. 25, 1999 | (JP) | 11-015661 |
| Jun. 1, 2000 | (JP) | 2000-164905 |
| Oct. 26, 2000 | (JP) | 2000-327148 |

(51) Int. Cl.
*A61B 18/18* (2006.01)

(52) U.S. Cl. .............. 606/52; 606/45; 606/51

(58) Field of Classification Search .......... 606/41, 606/45, 48–52
See application file for complete search history.

(56) References Cited

U.S. PATENT DOCUMENTS

| 702,472 A | 6/1902 | Pignolet |
| 728,883 A | 5/1903 | Downes |
| 3,613,682 A | 10/1971 | Naylor |
| 4,031,898 A | 6/1977 | Hiltebrandt et al. |
| 4,196,734 A | 4/1980 | Harris |
| 4,359,052 A | 11/1982 | Staub |

(Continued)

FOREIGN PATENT DOCUMENTS

DE   297 02 608   5/1997

(Continued)

OTHER PUBLICATIONS

Office action of Nov. 8, 2005 issued in counterpart Japanese application with English translation.*

(Continued)

*Primary Examiner*—Michael Peffley
(74) *Attorney, Agent, or Firm*—Frishauf, Holtz, Goodman & Chick, P.C.

(57) ABSTRACT

According to the present invention, a heat generating element to be current-carried is provided at a grasp portion on the tip side of a treatment portion, the patient's body tissue grasped between a pair of grasp portions is coagulated by heat of the heat generating element, and a metal scissors blade for cutting the patient's body tissue is provided on the rear side of the grasp portion in the treatment portion.

29 Claims, 48 Drawing Sheets

U.S. PATENT DOCUMENTS

| | | | |
|---|---|---|---|
| 4,685,459 A * | 8/1987 | Koch et al. | 606/51 |
| 5,151,102 A * | 9/1992 | Kamiyama et al. | 606/51 |
| 5,276,306 A | 1/1994 | Huffman | |
| 5,308,311 A | 5/1994 | Eggers et al. | |
| 5,336,221 A | 8/1994 | Anderson | |
| 5,342,381 A | 8/1994 | Tidemand | |
| 5,443,463 A | 8/1995 | Stern et al. | |
| 5,445,638 A | 8/1995 | Rydell et al. | |
| 5,458,598 A * | 10/1995 | Feinberg et al. | 606/52 |
| 5,593,406 A | 1/1997 | Eggers et al. | |
| 5,702,390 A * | 12/1997 | Austin et al. | 606/48 |
| 5,716,366 A | 2/1998 | Yates | |
| 5,792,137 A * | 8/1998 | Carr et al. | 606/29 |
| 5,908,420 A * | 6/1999 | Parins et al. | 606/51 |
| D420,741 S | 2/2000 | Croley | |
| 6,086,586 A * | 7/2000 | Hooven | 606/50 |
| 6,096,037 A * | 8/2000 | Mulier et al. | 606/49 |
| 6,113,598 A * | 9/2000 | Baker | 606/51 |
| 6,174,309 B1 * | 1/2001 | Wrublewski et al. | 606/45 |
| 6,273,887 B1 * | 8/2001 | Yamauchi et al. | 606/48 |
| 6,533,778 B2 * | 3/2003 | Herzon | 606/28 |
| 6,626,901 B1 | 9/2003 | Treat et al. | |
| 6,679,882 B1 * | 1/2004 | Kornerup | 606/51 |
| 6,860,880 B2 | 3/2005 | Treat et al. | |
| 6,908,463 B2 | 6/2005 | Treat et al. | |
| 7,025,763 B2 * | 4/2006 | Karasawa et al. | 606/28 |

FOREIGN PATENT DOCUMENTS

| | | |
|---|---|---|
| JP | 62-127040 A | 6/1987 |
| JP | 06-98150 | 12/1994 |
| JP | 6-511400 | 12/1994 |
| JP | 8-98845 A | 4/1996 |
| JP | 8-505801 | 6/1996 |
| JP | 8-275948 | 10/1996 |
| JP | 10-201770 | 8/1998 |
| JP | 10-286260 A | 10/1998 |
| JP | 11-137563 | 5/1999 |
| JP | 11-192238 A | 7/1999 |
| JP | 11-267132 A | 10/1999 |
| JP | 11-318919 | 11/1999 |
| JP | 11-318927 | 11/1999 |
| JP | 2000-5188 * | 1/2000 |
| JP | 2000-139943 A | 5/2000 |
| WO | WO 98/38935 * | 9/1998 |

OTHER PUBLICATIONS

Office Action of Apr. 23, 2002 issued in the counterpart Japanese application with English translation.

Official Action (Notification of Reasons For Rejection) mailed Jul. 19, 2005 by the Japanese Patent Office and English translation thereof.

* cited by examiner

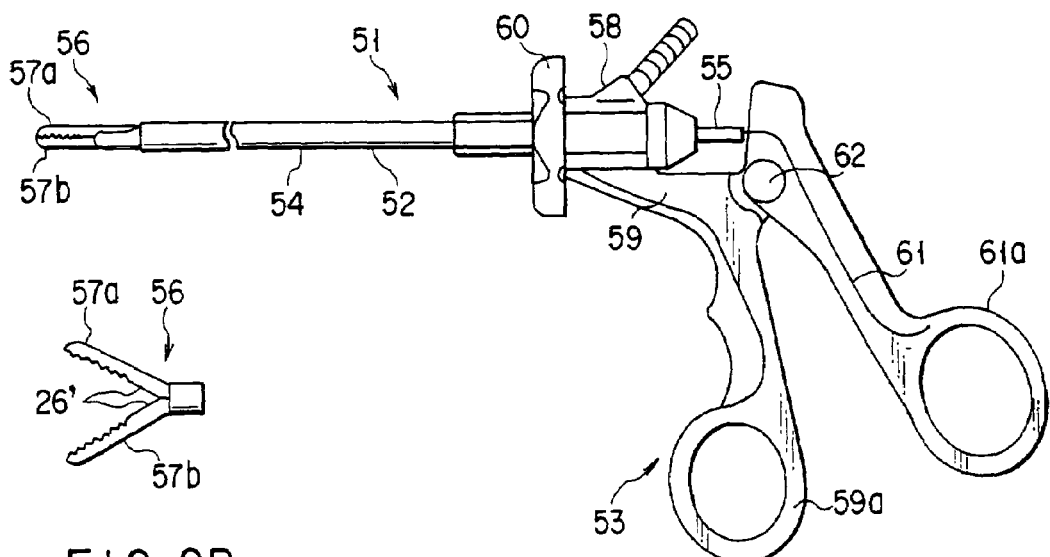
FIG. 9B
FIG. 9A
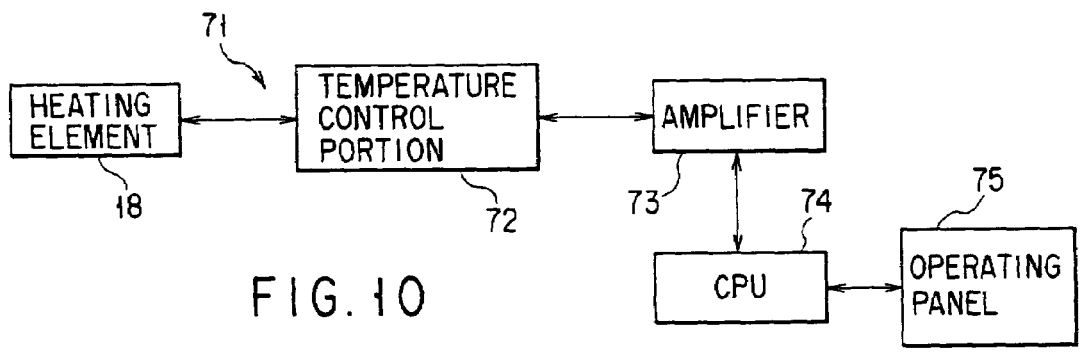
FIG. 10
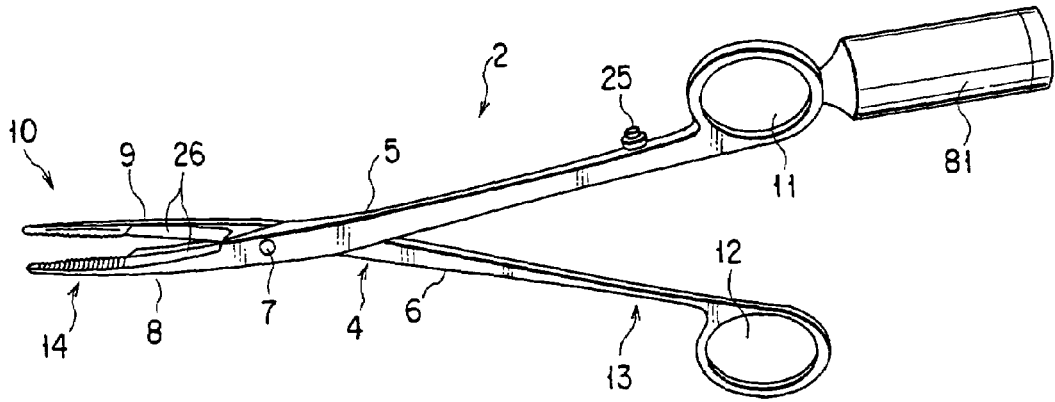
FIG. 11

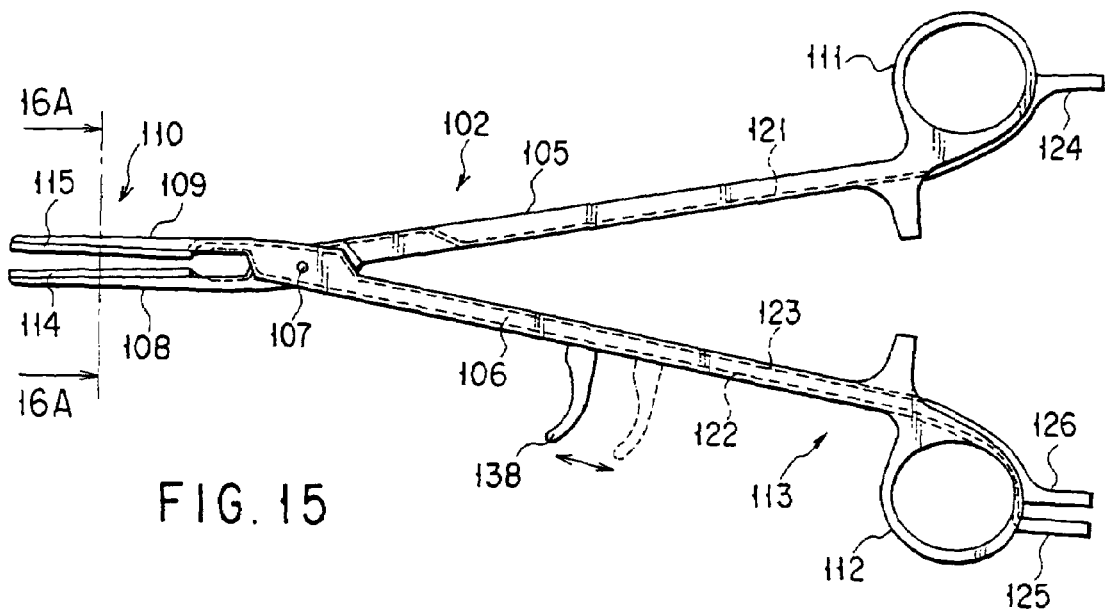
FIG. 15
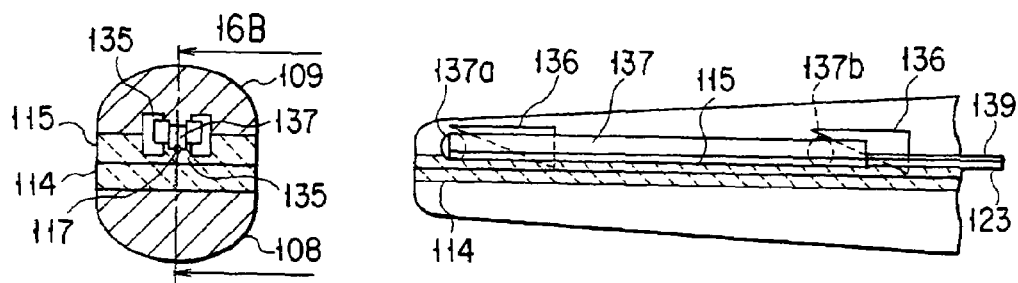
FIG. 16A
FIG. 16B
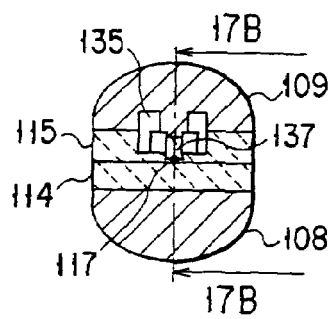
FIG. 17A
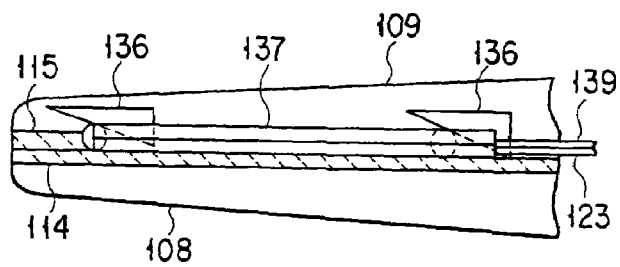
FIG. 17B

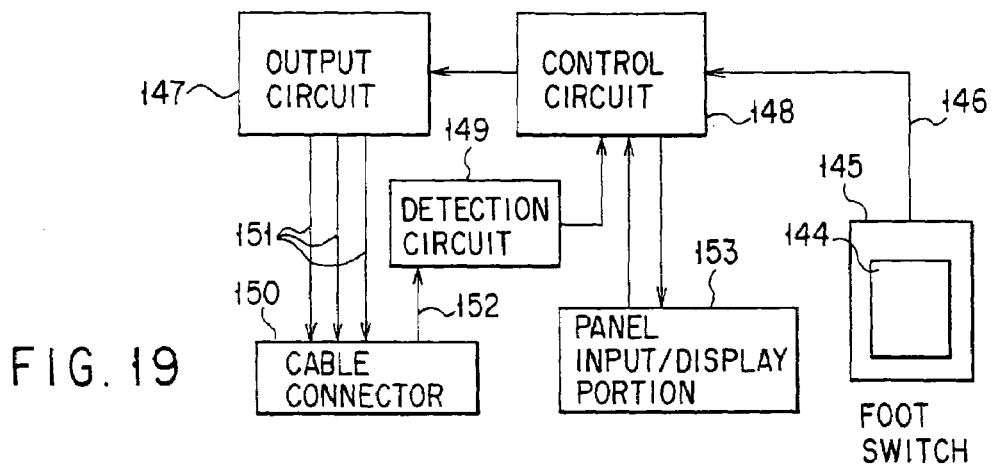
FIG. 19
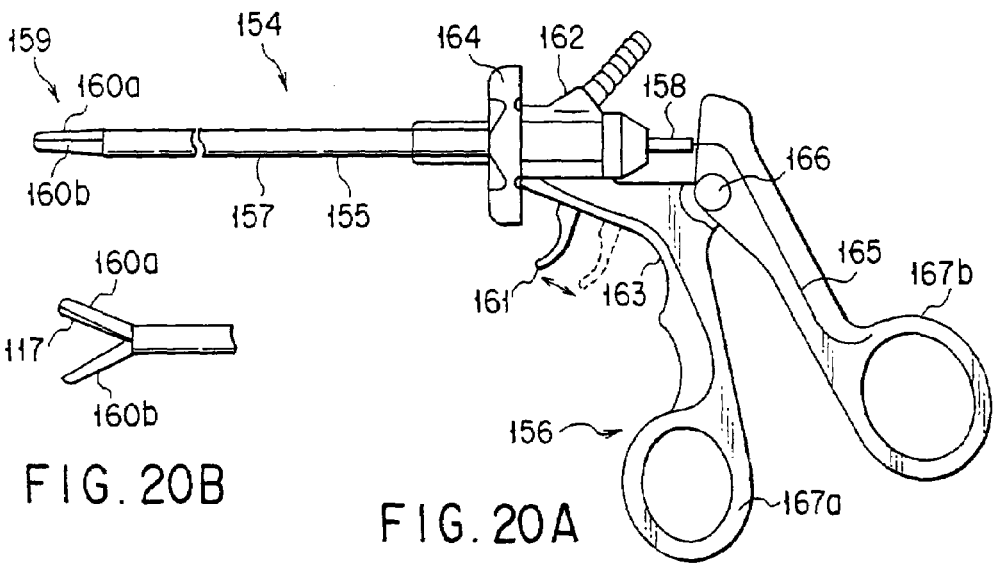
FIG. 20B
FIG. 20A
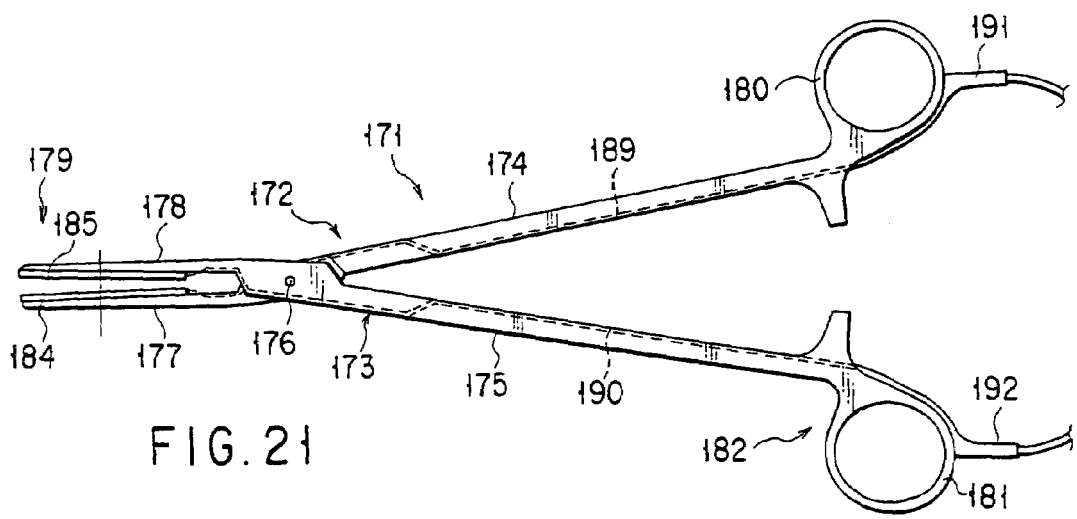
FIG. 21

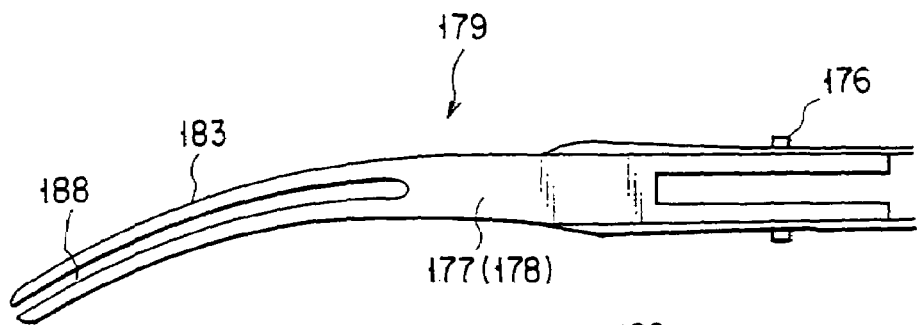
FIG. 22A
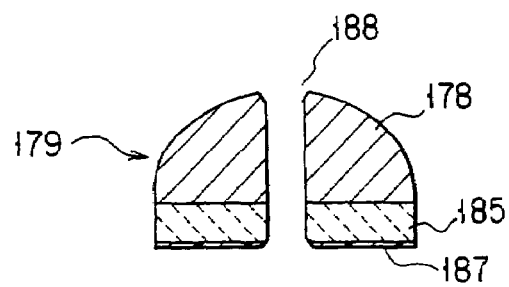
FIG. 22B
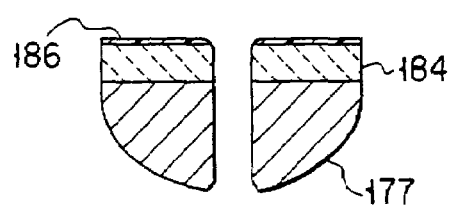
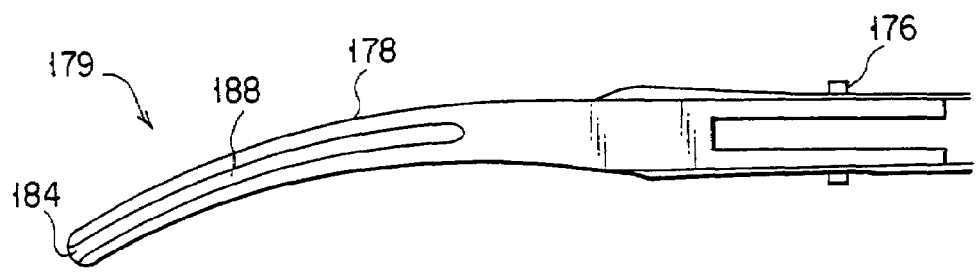
FIG. 23A
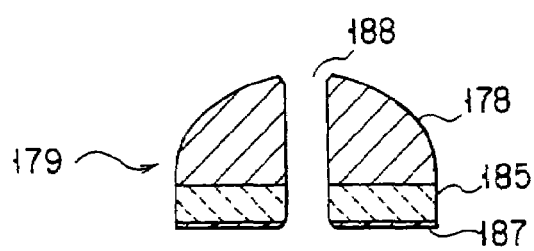
FIG. 23B
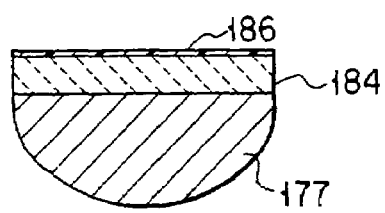

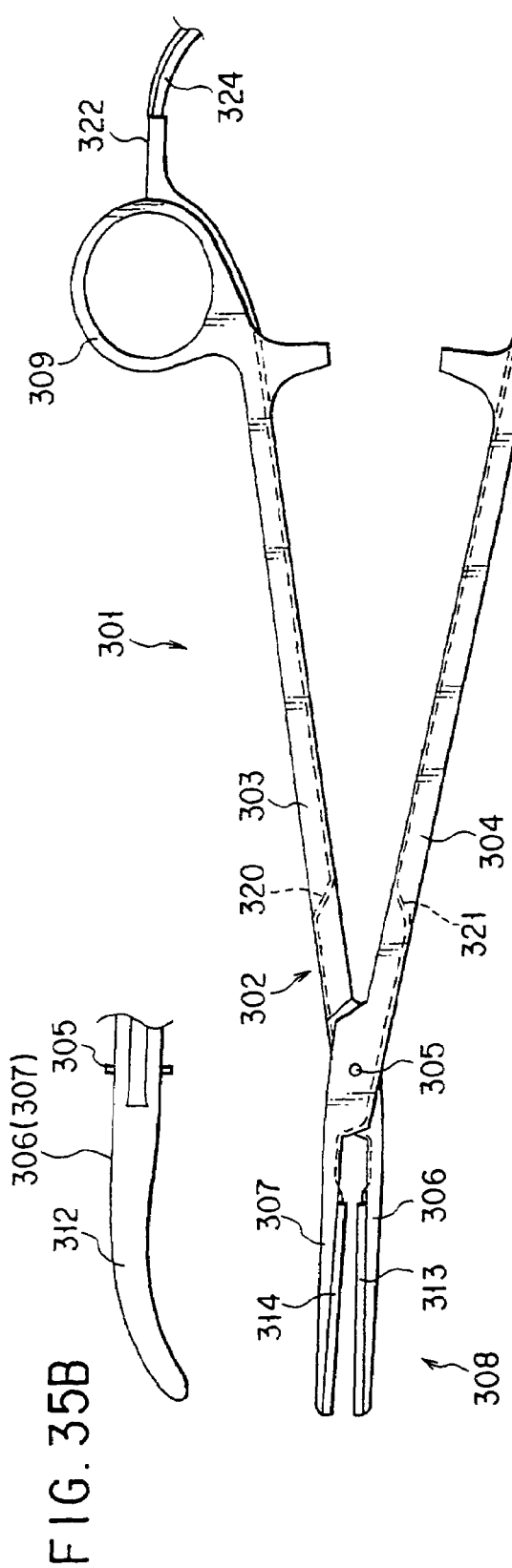
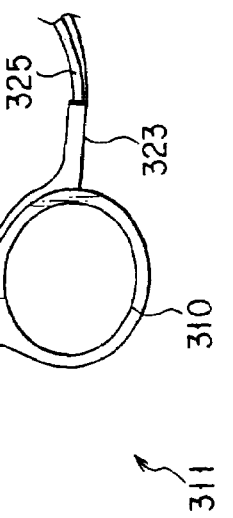
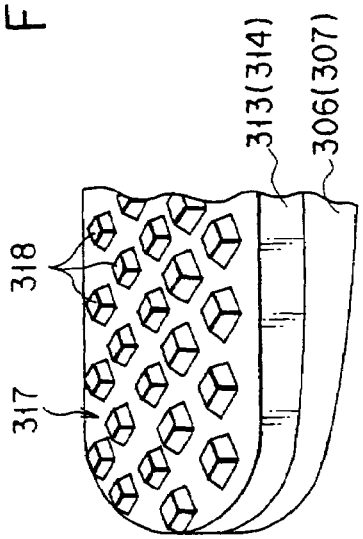
FIG. 35A
FIG. 35B
FIG. 35C

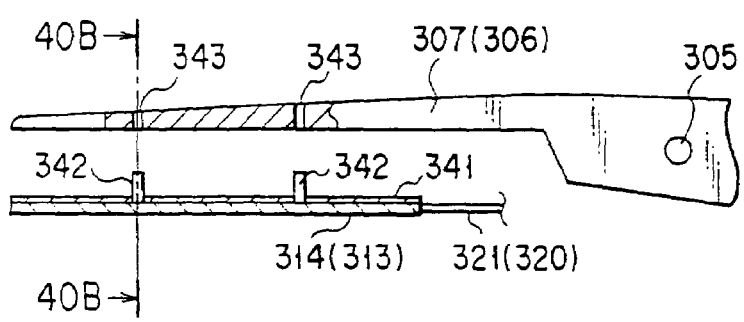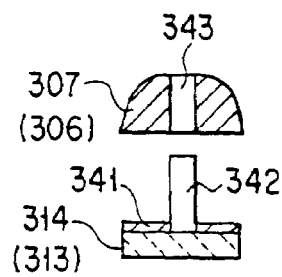
FIG. 40A  FIG. 40B
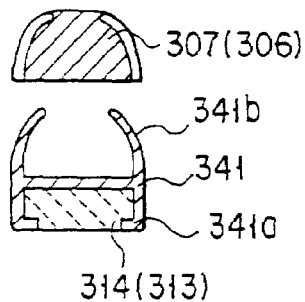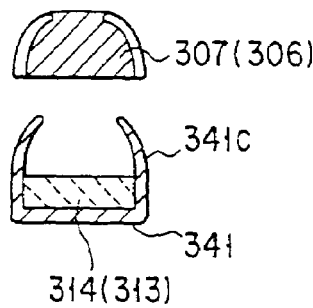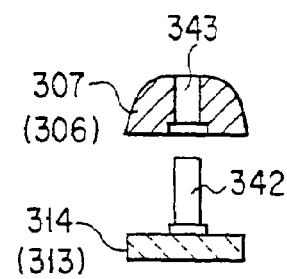
FIG. 41A  FIG. 41B  FIG. 40C
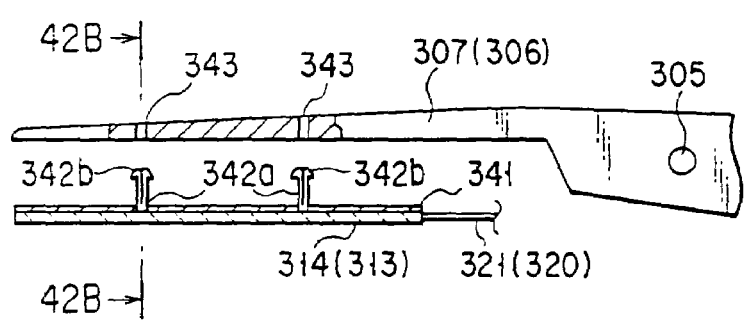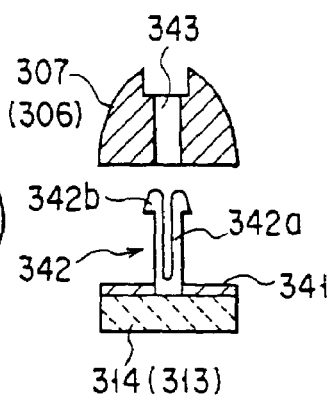
FIG. 42A  FIG. 42B

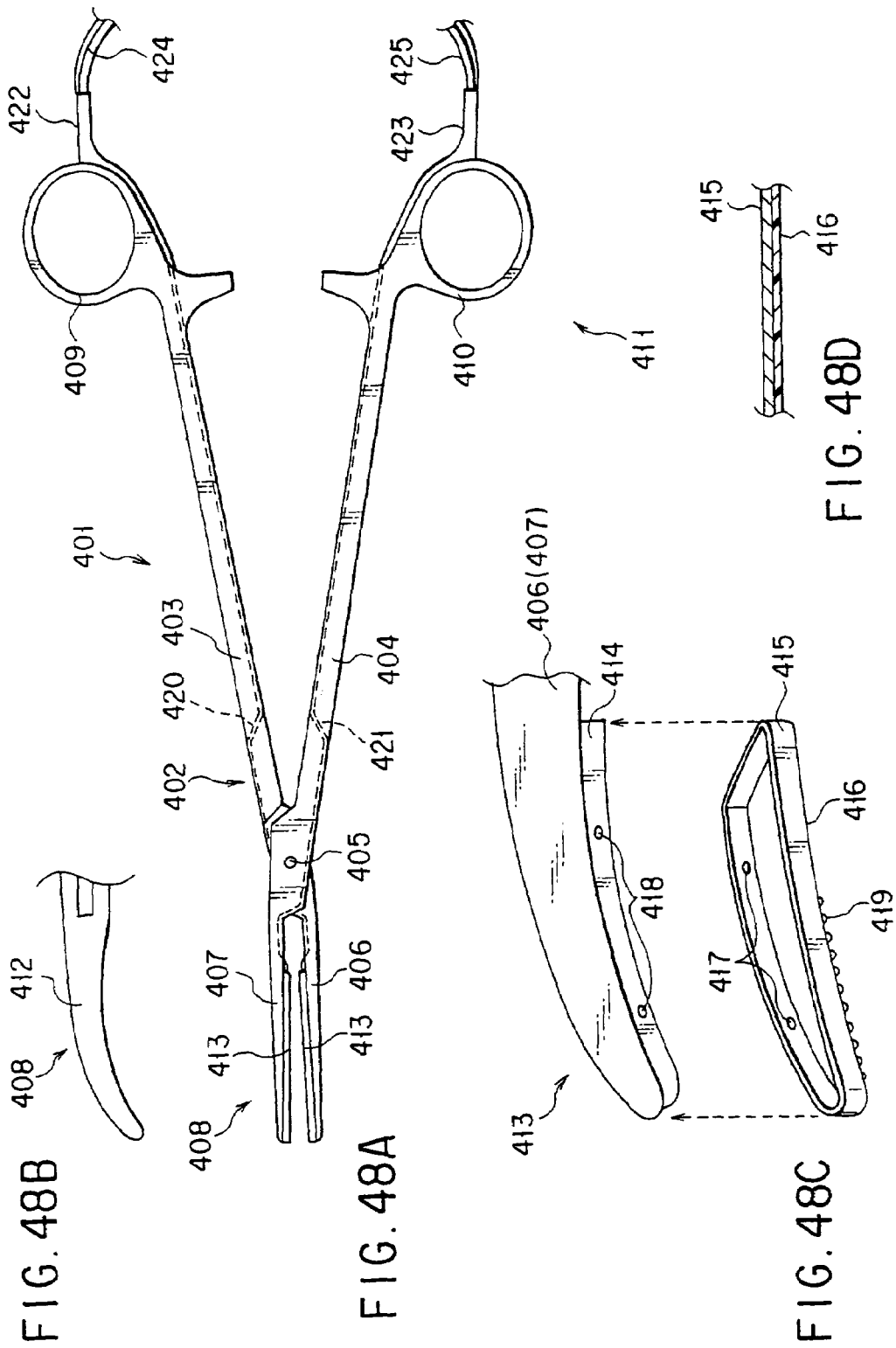

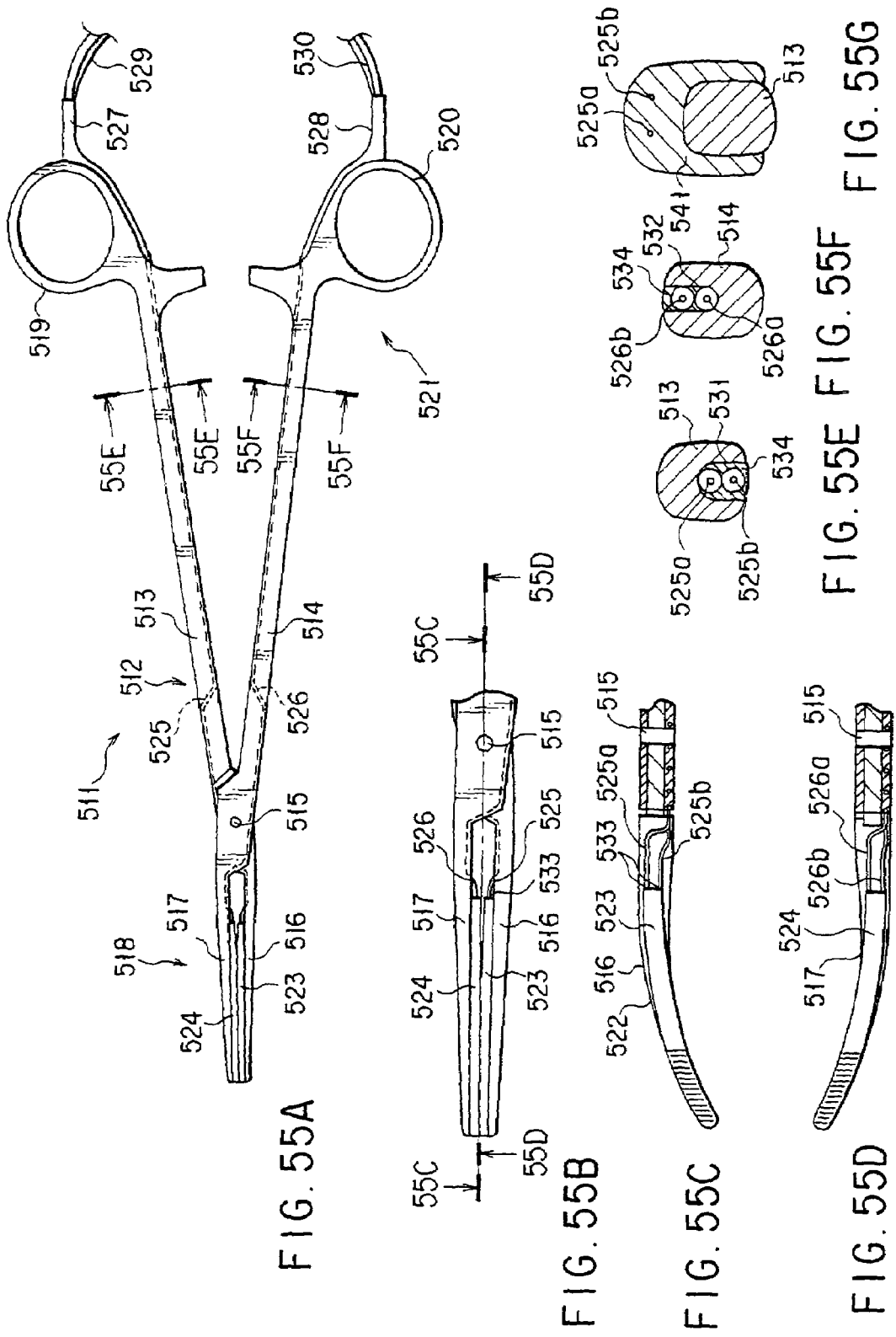

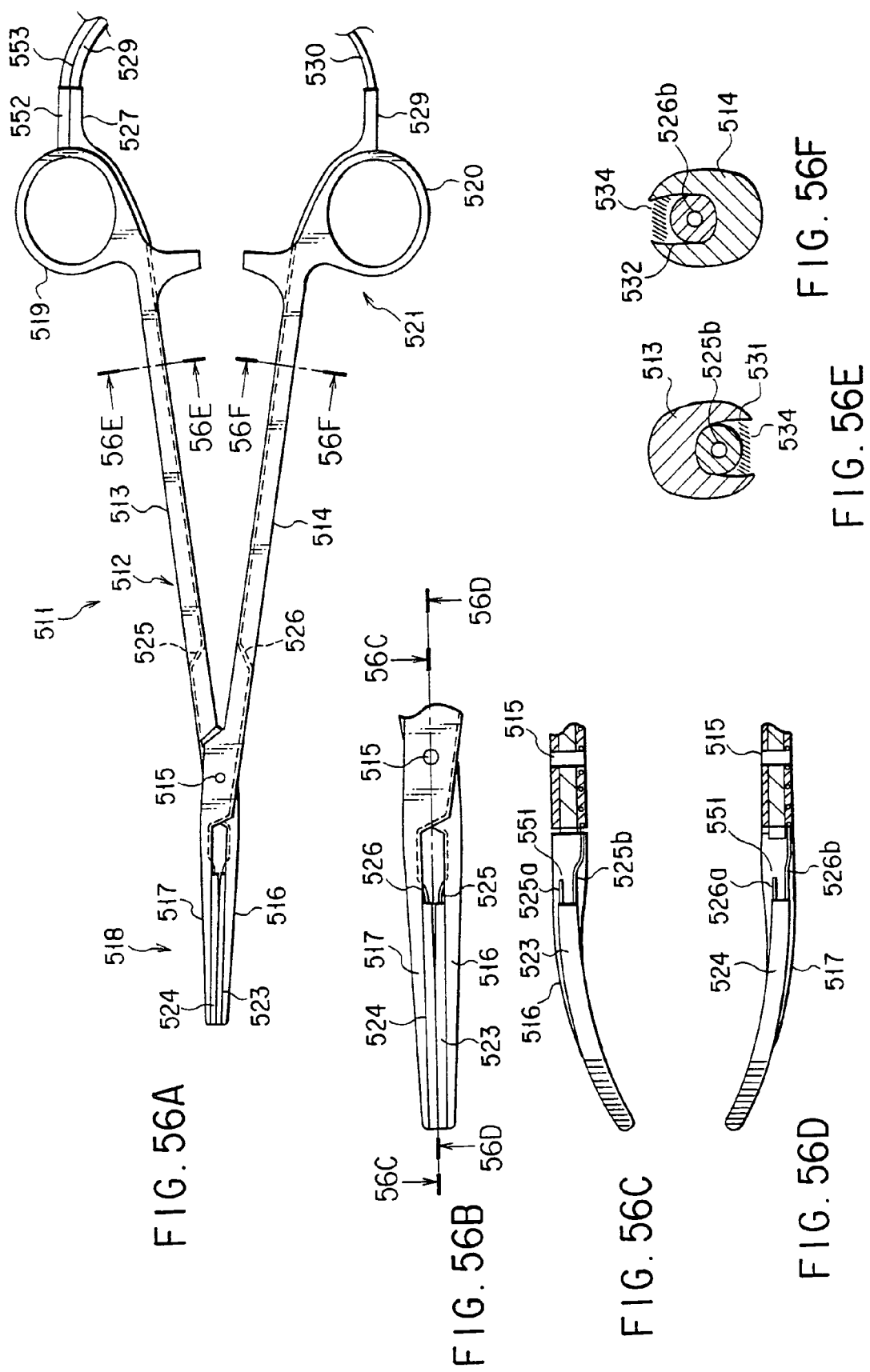

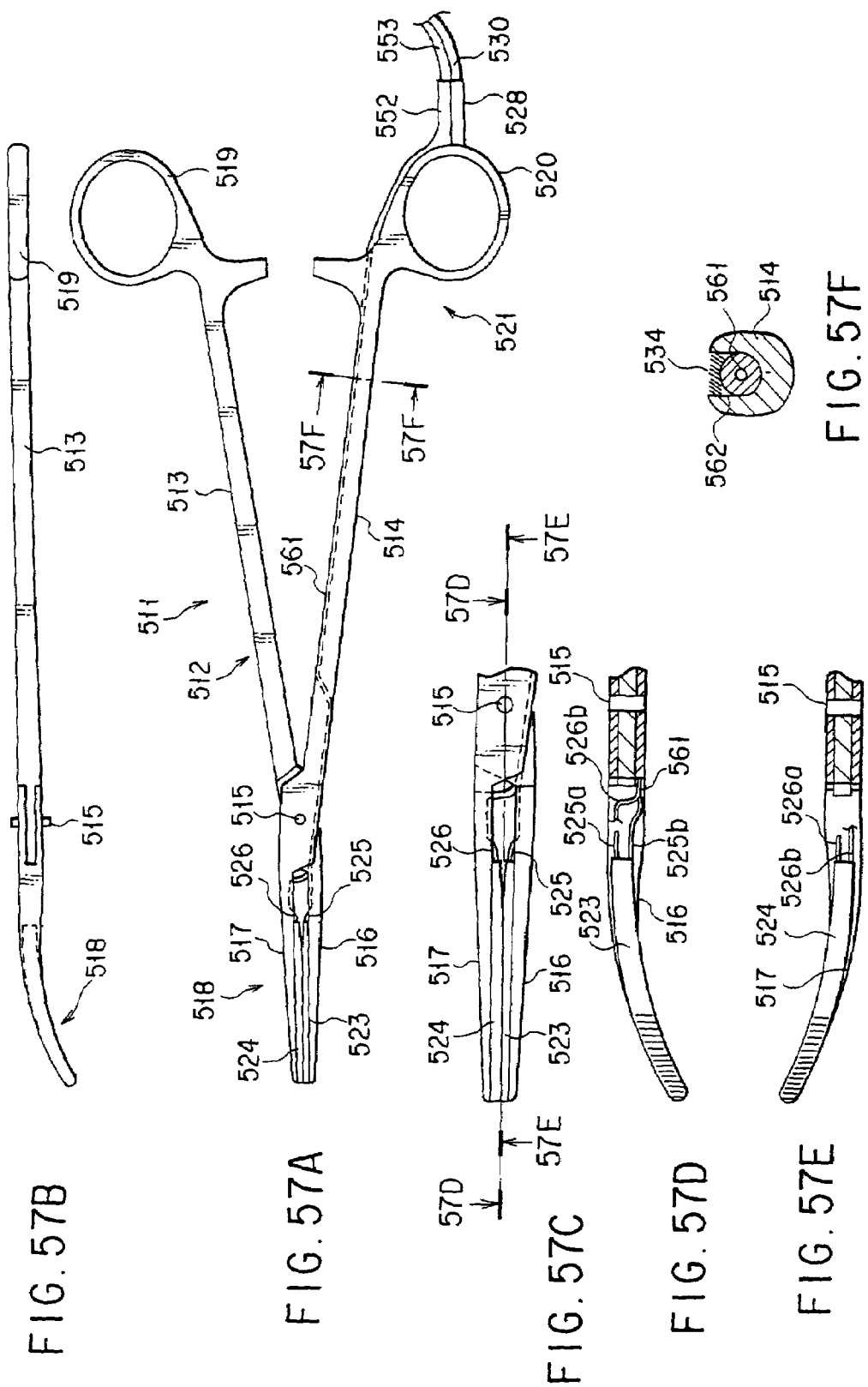

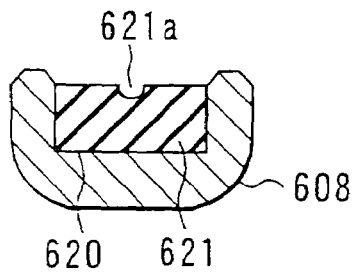 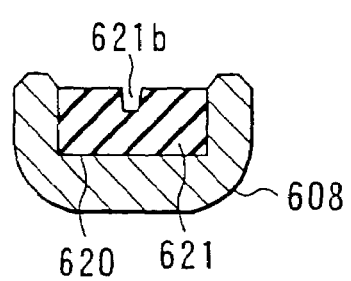 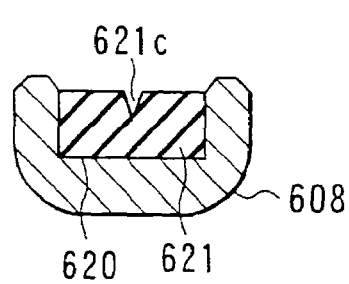
FIG. 68A  FIG. 68B  FIG. 68C
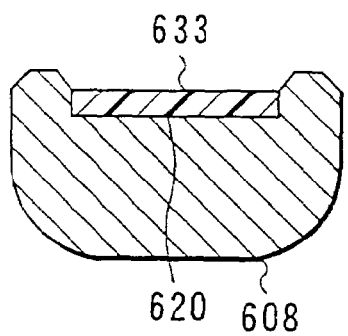
FIG. 69
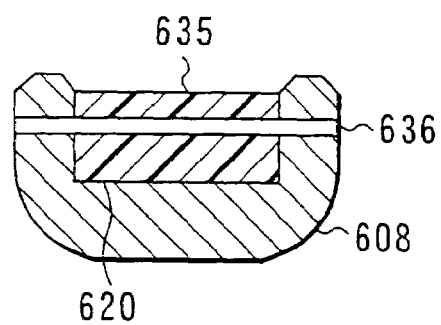
FIG. 70A
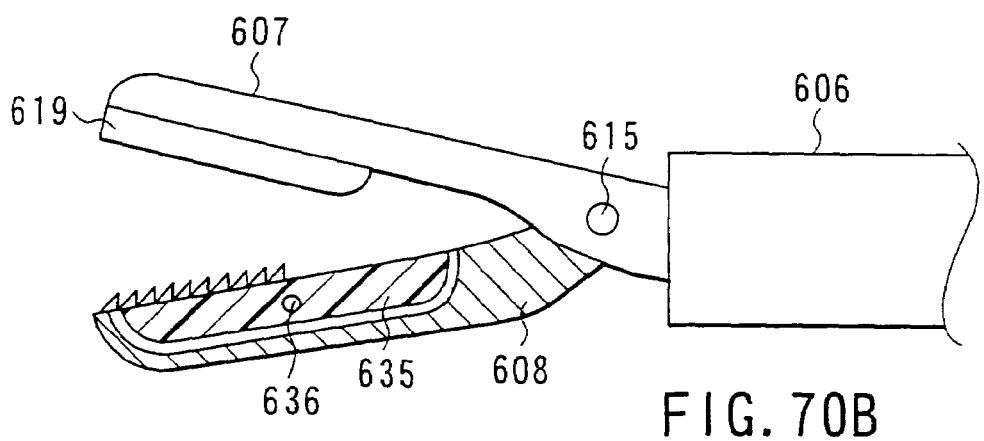
FIG. 70B

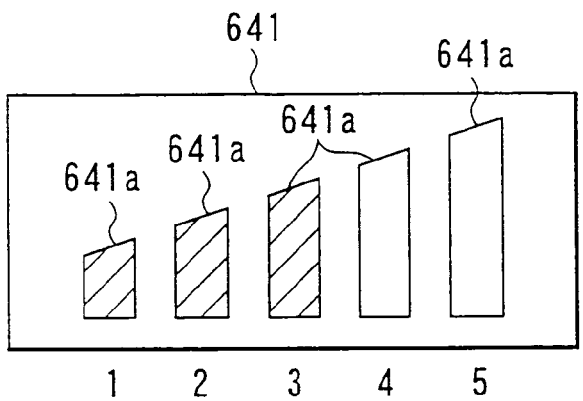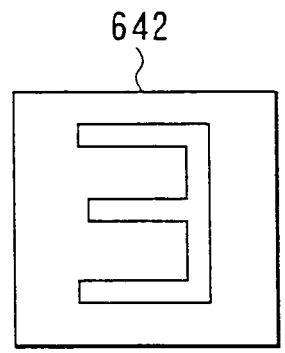
FIG. 71A
FIG. 71B
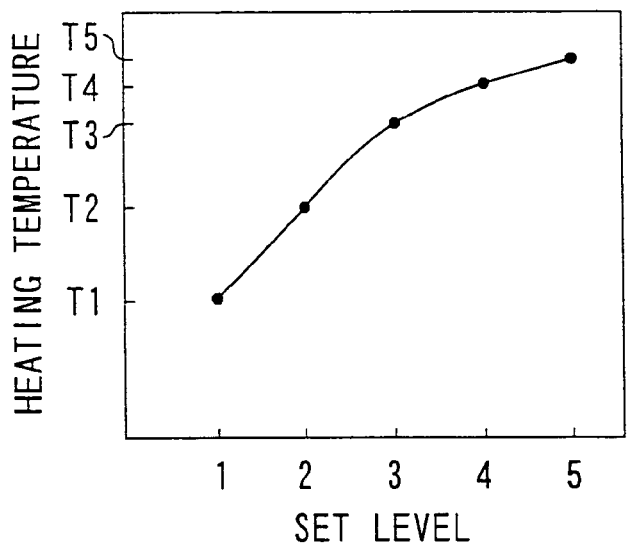
FIG. 72
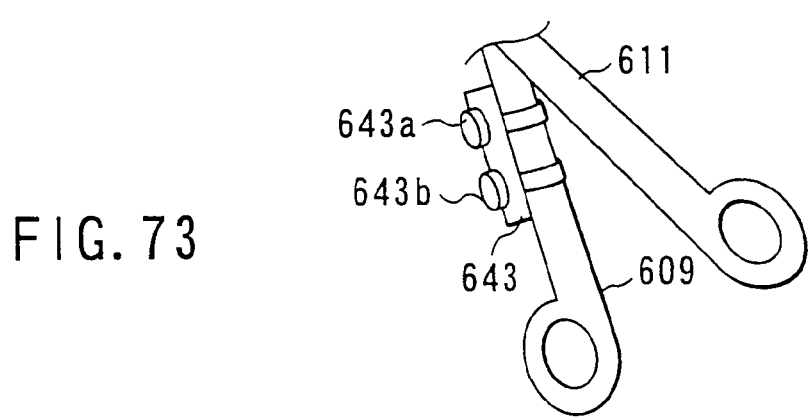
FIG. 73

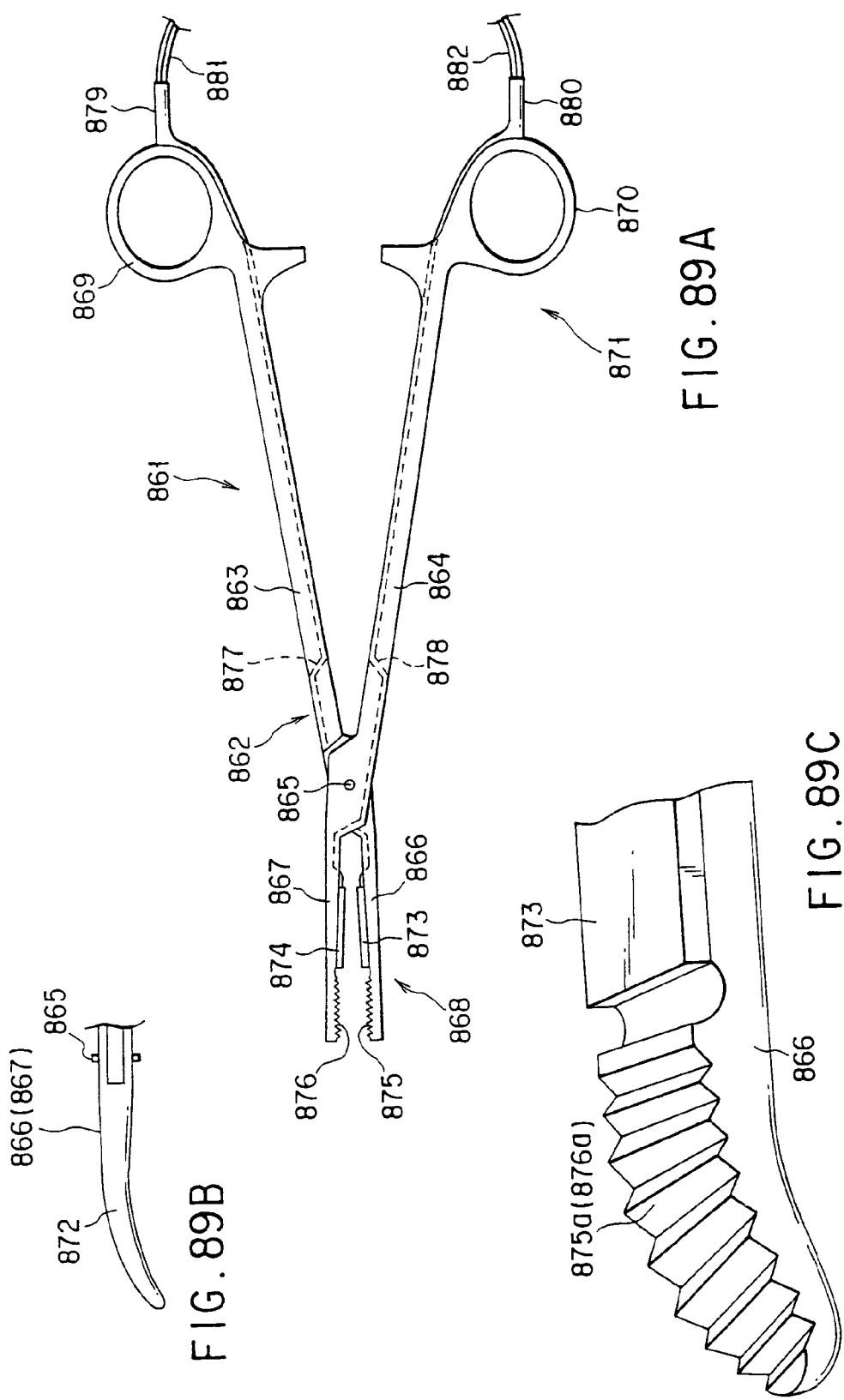

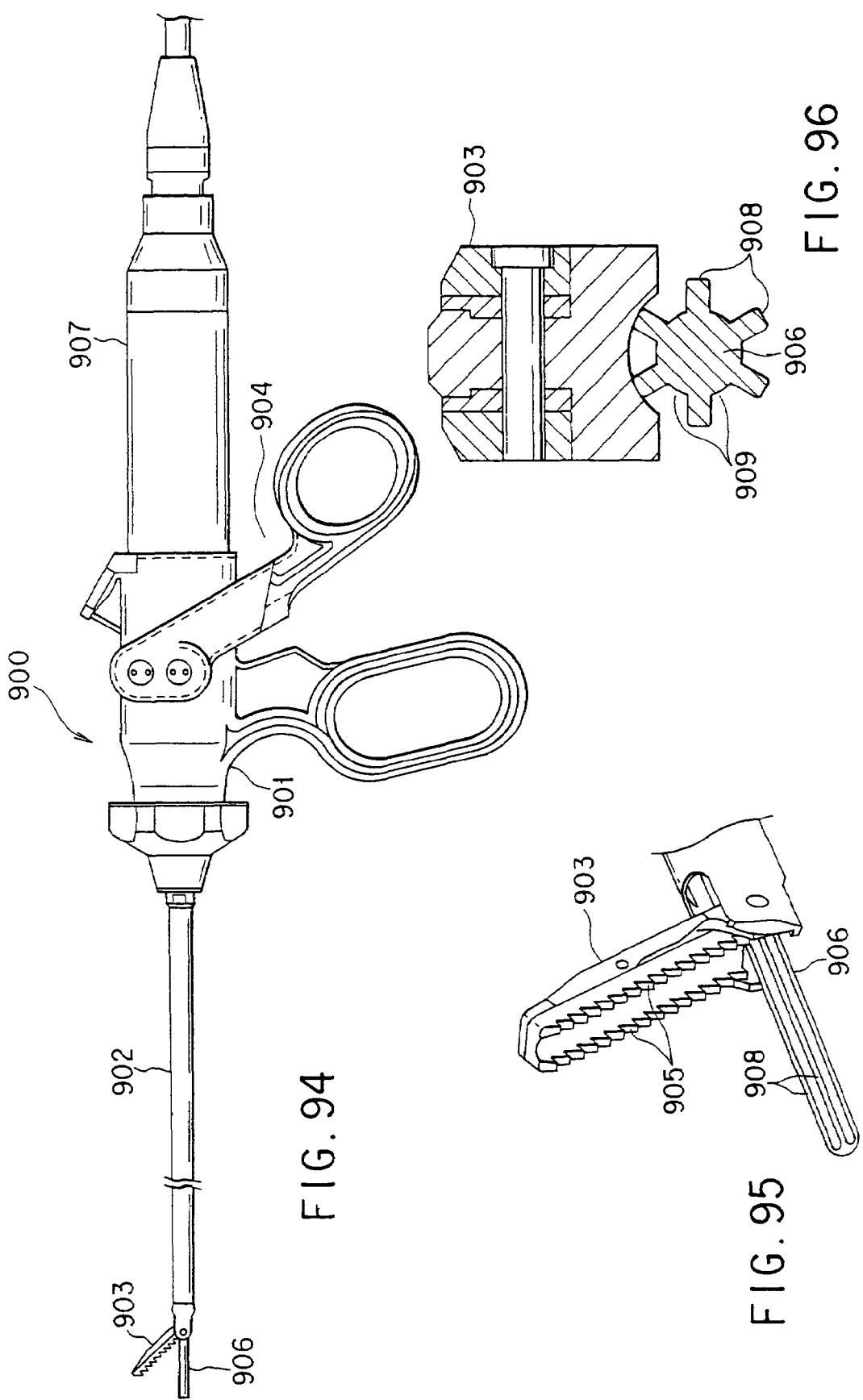

MEDICAL TREATMENT INSTRUMENT

CROSS-REFERENCE TO RELATED APPLICATIONS

This is a continuation of U.S. patent application Ser. No. 09/793,431, filed Feb. 26, 2001, which is abandoned, which is a continuation-in-part of U.S. patent application Ser. No. 09/488,732, filed Jan. 20, 2000, which is abandoned, the entire contents of each of which are incorporated herein by reference.

This application is based upon and claims the benefit of priority from the prior Japanese Patent Applications Nos. 11-015661, filed Jan. 25, 1999; No. 2000-327148, filed Oct. 26, 2000; and No. 2000-164905, filed Jun. 1, 2000, the entire contents of each of which are incorporated herein by reference.

BACKGROUND OF THE INVENTION

The present invention relates to a medical treatment instrument such as scissor forceps used for coagulating and cutting blood vessels or the like by inserting it into the patient's body cavity.

As a medical treatment instrument inserted into the patient's body, for example, a pair of electric heating type scissors is disclosed in German Patent DE 297 02 608 U1. This pair of electric heating type scissors is provided with two scissor constituent members rotatably coupled with each other around a rotating movement pin. A layer capable of electric heating is provided at a part of a dissection region disposed at the tip of these scissor constituent members.

In the electric heating type scissors disclosed in German Patent DE 297 02 608 U1, the two scissor constituent members are formed by relatively sharp cutting blades with thin plate thickness, respectively. Thus, when a patient's body tissue such as blood vessel is grasped between the two scissor constituent members, a contact area between these two scissor constituent members and the patient's body tissue is reduced. As a result, there is a problem that the patient's body tissue such as blood vessel cannot be sufficiently compressed between the two scissor constituent members, and the patient's body tissue such as blood vessel cannot be thermally coagulated.

In addition, in U.S. Pat. No. 5,342,381, there is disclosed a treatment instrument in which a treatment portion comprising a pair of treatment members capable of being opened and closed is arranged at the tip of the main body of the treatment instrument, and a frontal operating portion for opening/closing a pair of treatment members is arranged at the proximal end of the main body of the treatment instrument. In this treatment instrument, a grasp portion for grasping patient's body tissues is arranged at the tip side of the treatment section, and a dissection scissors section is arranged at the rear end of this grasp portion. In this treatment instrument, a bipolar high-frequency current is supplied to the grasp portion during in use; the patient's body tissue grasped by the grasp portion is coagulated by this high-frequency current, and then, a coagulation section of this patient's body tissue is cut at the scissors section.

In addition, the treatment instrument disclosed in U.S. Pat. No. 5,342,381 is configured to supply a bipolar high-frequency current to the grasp portion at the tip side of the treatment section, so that a portion of the scissors section at the rear end of the grasp portion cannot be made of metal. Therefore, in the treatment instrument disclosed in U.S. Pat. No. 5,342,381, the scissors portion of the treatment section is composed of an insulator consisting of ceramics. However, thus, there is a problem that, when a ceramic based scissors portion is used, the dissection capability is gradually degraded due to a friction between slide portions of the scissors portion during in use.

BRIEF SUMMARY OF THE INVENTION

The present invention has been achieved in view of the foregoing circumference. It is an object of the present invention to provide a medical treatment instrument capable of reliably thermally coagulating a patient's body tissue such as blood vessel grasped between a pair of treatment members and capable of reducing degradation of the dissection capability of a dissection portion due to a scissors during in use and maintaining sharpness of the dissection portion for a long period of time.

In order to achieve the foregoing object, according to the present invention, there is provided a medical treatment instrument used for coagulating and cutting the patient's body tissue, the medical treatment instrument comprising:

a treatment portion arranged at the tip of the treatment instrument, the treatment portion being supported to be capable of being opened and closed, comprising a pair of grasp portions for grasping the patient's body tissue;

a frontal operating portion arranged at the proximal end of the treatment instrument, the operating portion opening and closing a pair of the grasp portions;

a heat generating portion provided on at least one of the grasp portions, the heat generating portion current-carried and heated to coagulate the patient's body tissue grasped between the grasp portions; and a cutting portion disposed at each of the grasp portions, the cutting portion cutting the patient's body tissue.

In the present invention, during in use, the heat generating portion at the tip side in the treatment portion is current-carried and heated, and the patient's body tissue such as blood vessel wall grasped between a pair of grasp portions is coagulated by heat of the heat generating portion and is welded. Then, the coagulated site of the patient's body tissue is cut by the cutting portion with a pair of scissors on the rear side of the grasp portions in the treatment portion.

Therefore, according to the present invention, the heat generating portion to be current-carried and heated is provided at least at one grasp portion on the tip side of the treatment portion; the patient's body tissue grasped between a pair of the grasp portions is coagulated by heat of the heat generating portion, and the cutting portion with the scissors and cutting the patient's body tissue on the rear side of the grasp portions is provided. Thus, the patient's body tissue such as blood vessel grasped between a pair of the grasp portions can be reliably thermally coagulated by heat of the heat generating portion. Further, degradation of the cutting capability of the cutting portion due to the scissors during in use is reduced, and the sharpness of the cutting portion can be maintained for a long period of time.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 9A is a side view showing the entire surgical treatment instrument in a fourth embodiment of the present invention;

FIG. 9B is a side view of essential portions showing an opened state of a tip grasp portion of the surgical treatment instrument according to the fourth embodiment;

FIG. 10 is a schematic structural view of essential portions showing a fifth embodiment of the present invention;

FIG. 11 is a perspective view of the entire medical treatment instrument showing a sixth embodiment of the present invention;

FIG. 15 is a plan view of the entire forceps showing a twelfth embodiment of the present invention;

FIG. 16A is a cross sectional view taken along the line 16A-16A of FIG. 15 showing a state in which a heat generating section for dissection treatment in the forceps of the twelfth embodiment is maintained at a standby position departed from a heat generating section for coagulating treatment;

FIG. 16B is a cross sectional view taken along the line 16B-16B of FIG. 16A;

FIG. 17A is a longitudinal sectional view of essential portions of scissor constituent members showing a state in which the heat generating section for dissection treatment in the forceps according to the twelfth embodiment is brought into contact with the heat generating section for coagulating treatment;

FIG. 17B is a cross sectional view taken along the line 17B-17B of FIG. 17A;

FIG. 19 is a schematic structural view showing an electric circuit of a power supply unit in the medical treatment instrument system according to the thirteenth embodiment;

FIG. 20A is a side view showing the entire medical treatment instrument according to a fourteenth embodiment of the present invention;

FIG. 20B is a side view of essential portions showing an opened state of a grasp element of the treatment section in the medical treatment instrument according to the fourteenth embodiment;

FIG. 21 is an entire side view showing a medical treatment instrument according to a fifteenth embodiment of the present invention;

FIG. 22A is a plan view of essential portions showing a curve portion of an opening/closing element of the medical treatment instrument according to the fifteenth embodiment of the present invention;

FIG. 22B is a cross sectional view showing a treatment section of the medical treatment instrument according to the fifteenth embodiment;

FIG. 23A is a plan view of essential portions showing a curve portion of a grasp portion in a medical treatment instrument according to a sixteenth embodiment of the present invention;

FIG. 23B is a cross sectional view of the curve portion in the medical treatment instrument according to the sixteenth embodiment;

FIG. 35A is a side view of the entire coagulating treatment instrument according to a twenty-sixth embodiment of the present invention;

FIG. 35B is a plan view showing the curve shape of the jaw of the coagulating treatment instrument according to the twenty-sixth embodiment;

FIG. 35C is a perspective view showing a non-slip teeth section of the patient's body tissues of a heating element in the coagulating treatment instrument according to the twenty-sixth embodiment;

FIG. 40A is a sectional side view partially showing a state before mounting an intermediate connecting member of the jaw in the coagulating treatment instrument according to the twenty-eighth embodiment;

FIG. 40B is a cross sectional view taken along the line 40B-40B of FIG. 40A;

FIG. 40C is a longitudinal section view showing a modified example of a structure for mounting the connection pin of the connection plate according to the twenty-eighth embodiment;

FIG. 41A is a longitudinal sectional view showing a first modified example of a structure for mounting the intermediate connecting member in the coagulating treatment instrument according to the twenty-eighth embodiment;

FIG. 41B is a longitudinal sectional view showing a second modified example of a structure for mounting the intermediate connecting member in the coagulating treatment instrument according to the twenty-eighth embodiment;

FIG. 42A is a sectional side view partially showing a state before mounting the intermediate connecting member of the jaw in the coagulating treatment instrument according to a twenty-ninth embodiment of the present invention;

FIG. 42B is a cross sectional view taken along the line 42B-42B of FIG. 42A;

FIG. 48A is a front view of the entire coagulating treatment instrument showing a thirty-fourth embodiment of the present invention;

FIG. 48B is a plan view showing a curve shape of the jaw of the coagulating treatment instrument according to the thirty-fourth embodiment;

FIG. 48C is a perspective view of a heater cover of an upper jaw according to the thirty-fourth embodiment;

FIG. 48D is a longitudinal sectional view of essential portions showing the tissue adhesion preventing treatment portion of the cover according to the thirty-fourth embodiment;

FIG. 55A is a front view of the entire coagulating treatment instrument showing a thirty-ninth embodiment of the present invention;

FIG. 55B is an enlarged front view showing the jaw at the tip of the coagulating treatment instrument according to the thirty-ninth embodiment;

FIG. 55C is a cross sectional view taken along the line 55C-55C of FIG. 55B;

FIG. 55D is a cross sectional view taken along the line 55D-55D of FIG. 55B;

FIG. 55E is a cross sectional view taken along the line 55E-55E of FIG. 55A;

FIG. 55F is a cross sectional view taken along the line 55F-55F of FIG. 55A;

FIG. 55G is a cross sectional view of essential portions showing a modified example of the coagulating treatment instrument according to the thirty-ninth embodiment;

FIG. 56A is a front view of the entire coagulating treatment instrument showing a fortieth embodiment of the present invention;

FIG. 56B is an enlarged front view showing the jaw at the tip of the coagulating treatment instrument according to the fortieth embodiment;

FIG. 56C is a cross sectional view taken along the line 56C-56C of FIG. 56B;

FIG. 56D is a cross sectional view taken along the line 56D-56D of FIG. 56B;

FIG. 56E is a cross sectional view taken along the line 56E-56E of FIG. 56A;

FIG. 56F is a cross sectional view taken along the line 56F-56F of FIG. 56A;

FIG. 57A is a front view of the entire coagulating treatment instrument showing a forty-first embodiment of the present invention;

FIG. 57B is a plan view showing the coagulating treatment instrument according to the forty-first embodiment;

FIG. 57C is an enlarged front view showing the jaw at the tip of the coagulating treatment instrument according to the forty-first embodiment;

FIG. 57D is a cross sectional view taken along the line 57D-57D of FIG. 57C;

FIG. 57E is a cross sectional view taken along the line 57E-57E of FIG. 57C;

FIG. 57F is a cross sectional view taken along the line 57F-57F of FIG. 57A;

FIG. 67 is a sectional view of a holding portion of a thermocoagulation cutting forceps according to a forty-seventh embodiment of the invention;

FIG. 68A is a sectional view of a holding portion of a thermocoagulation cutting forceps according to a forty-eighth embodiment of the invention;

FIG. 68B is a sectional view showing a modification of the heating portion of FIG. 68A;

FIG. 68C is a sectional view showing another modification of the heating portion of FIG. 68A;

FIG. 69 is a sectional view of a holding portion of a thermocoagulation cutting forceps according to a forty-ninth embodiment of the invention;

FIG. 70A is a sectional view of a holding portion of a thermocoagulation cutting forceps according to a fiftieth embodiment of the invention;

FIG. 70B is a perspective view showing holding portions of the forceps of the fiftieth embodiment;

FIG. 71A is a diagram showing bars indicative of the temperature level, on a display portion of a power source unit according to a fifty-first embodiment of the invention;

FIG. 71B is a diagram showing a figure indicative of the temperature level, on the display portion of the power source unit of the fifty-first embodiment;

FIG. 72 is a graph showing the relation between the set level and the heating temperature displayed on the display portion of the power source unit of the fifty-first embodiment;

FIG. 73 is a perspective view of an operating portion of a thermocoagulation cutting forceps according to a fifty-second embodiment of the invention;

FIG. 74 is a perspective view of a thermocoagulation cutting forceps according to a fifty-third embodiment of the invention;

Figure 75:
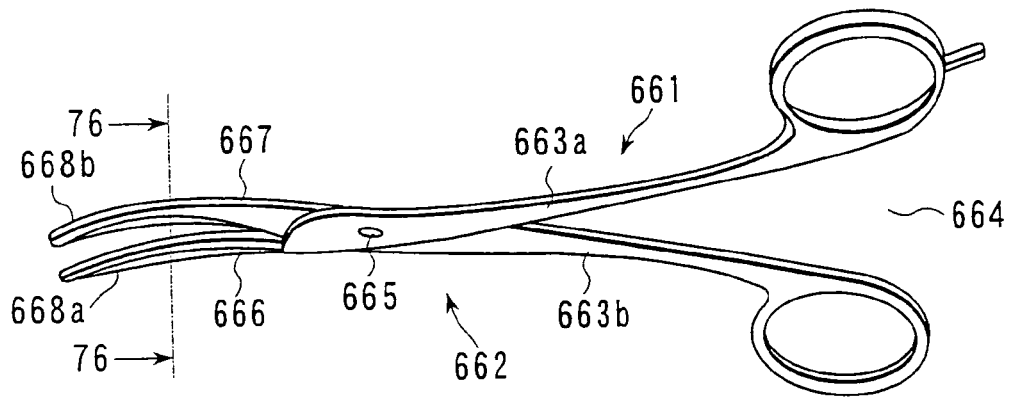
Figure 76:
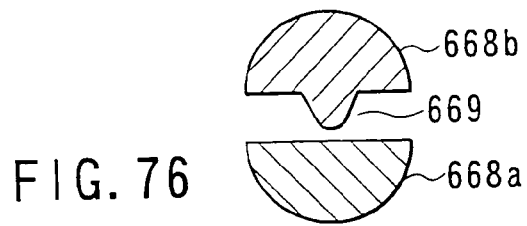
Figure 77A:
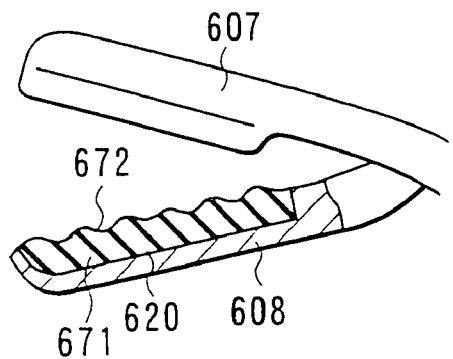
Figure 77B:
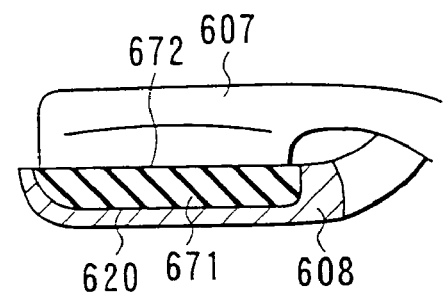
Figure 78A:
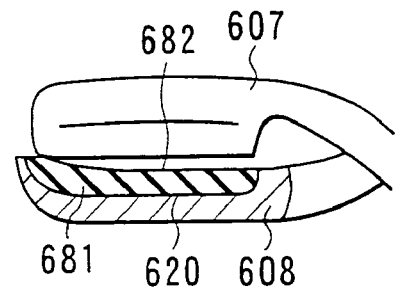
Figure 78B:
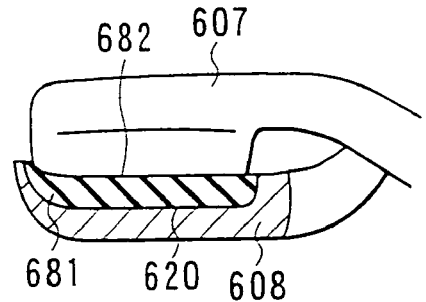
Figure 79A:
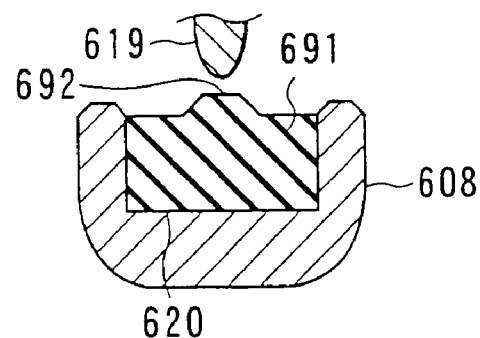
Figure 79B:
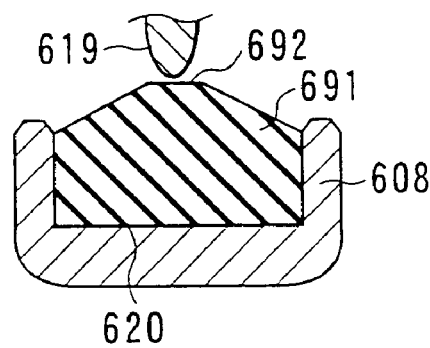
Figure 80A:
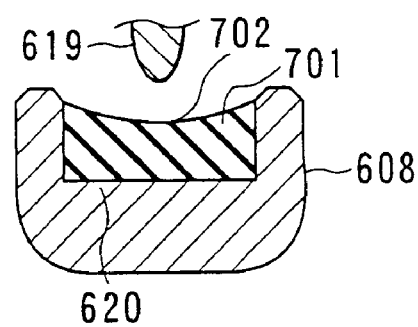
Figure 80B:
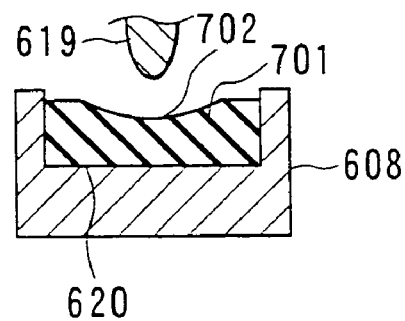
Figure 81:
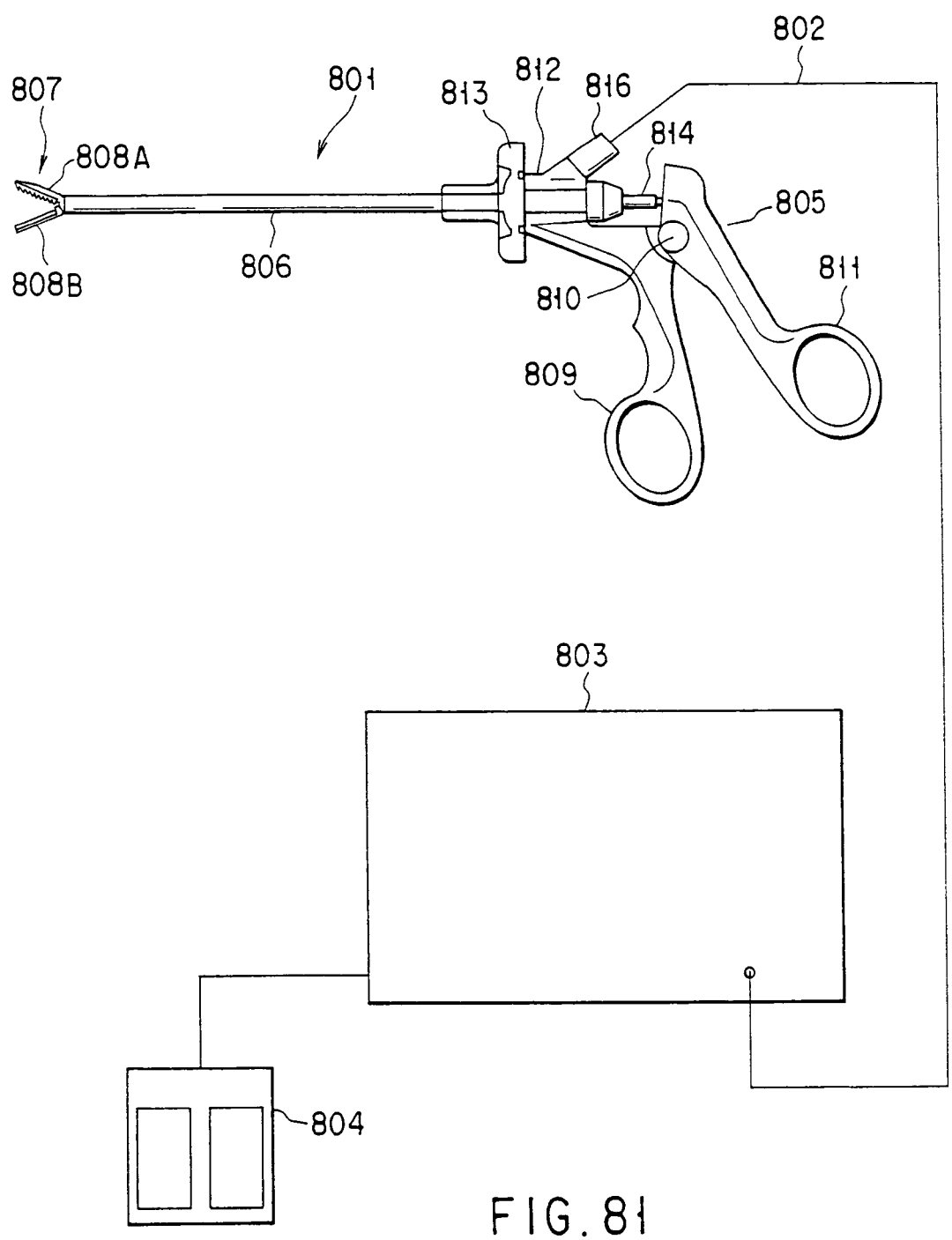
Figure 82:
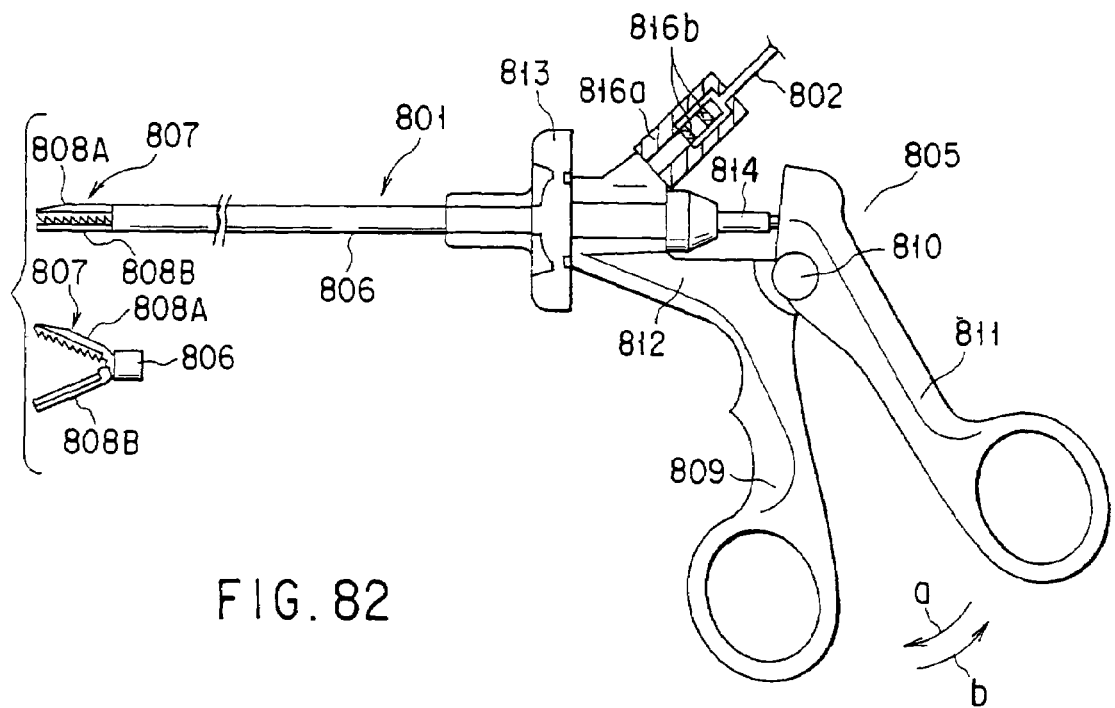
Figure 83:
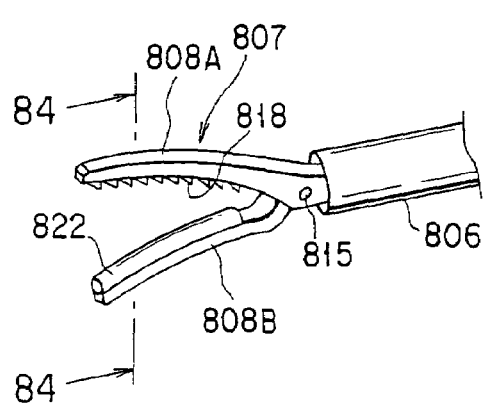
Figure 84:
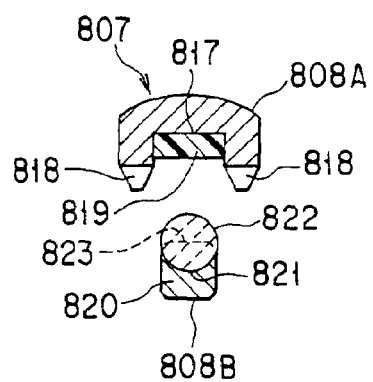
Figure 85:
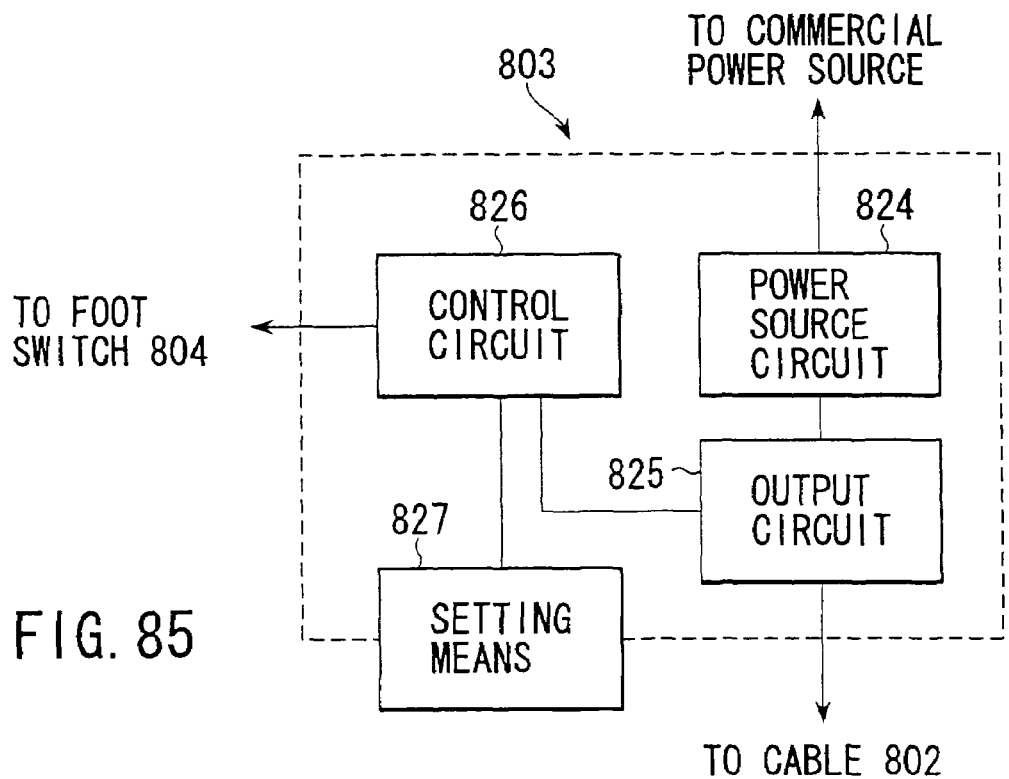
Figure 86:
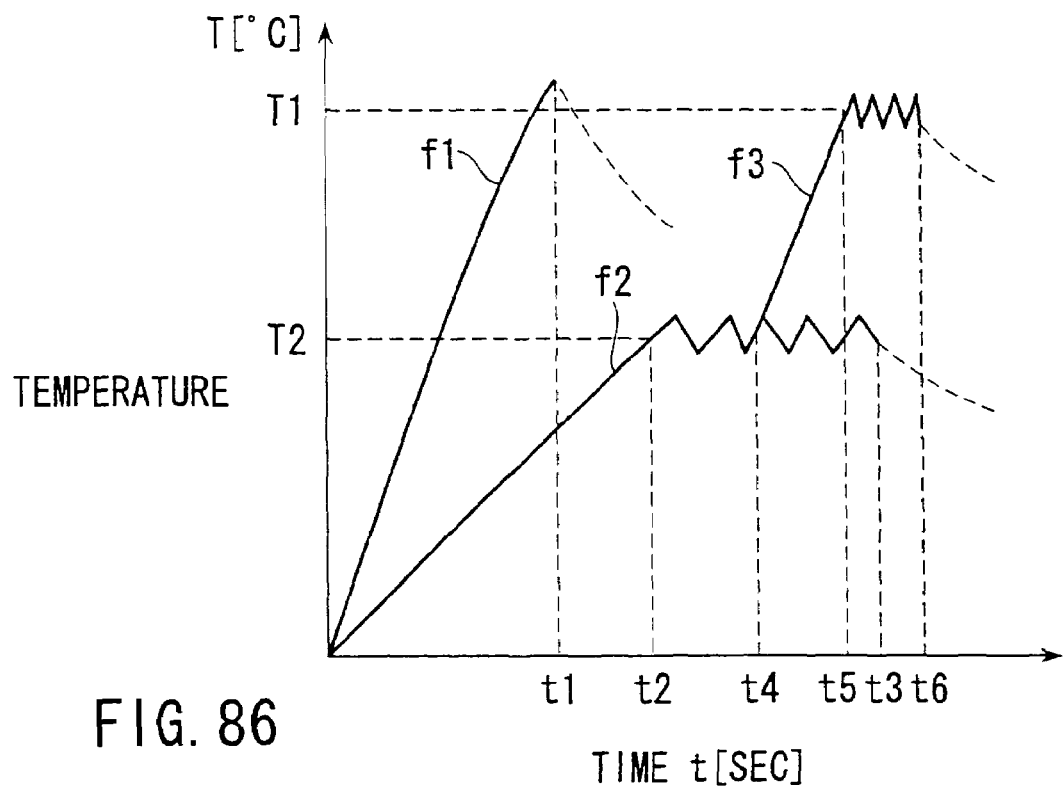
Figure 87A:
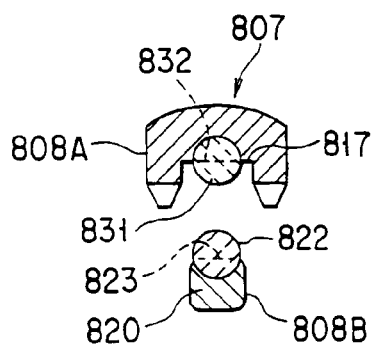
Figure 87B:
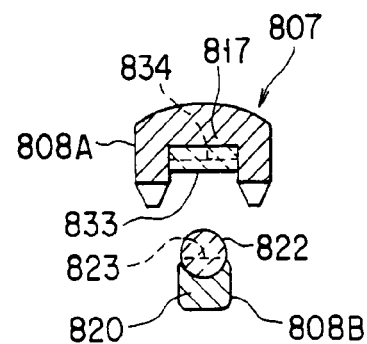
Figure 87C:
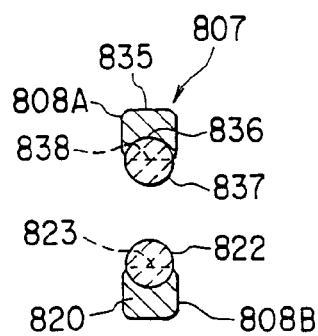
Figure 87D:
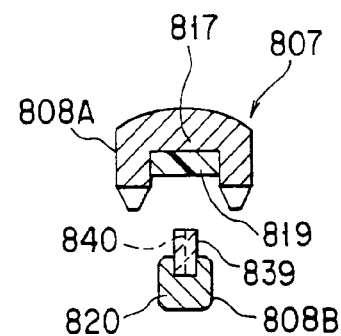
Figure 87E:
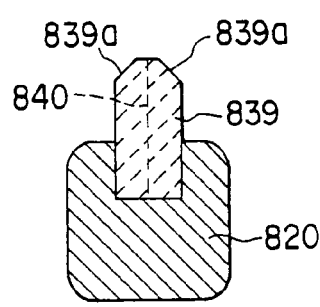
Figure 87F:
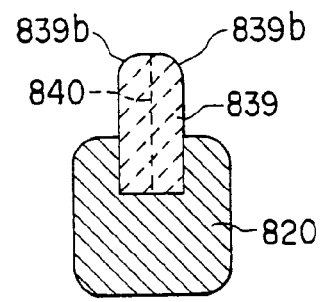
Figure 88:
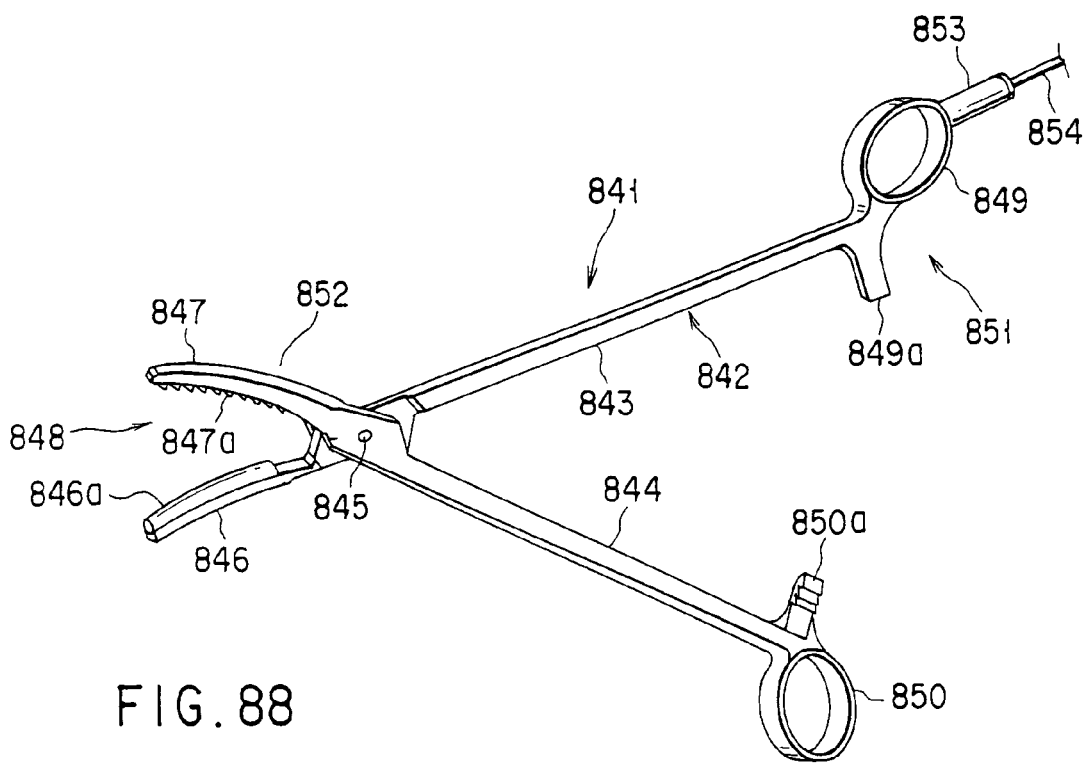
Figure 90:
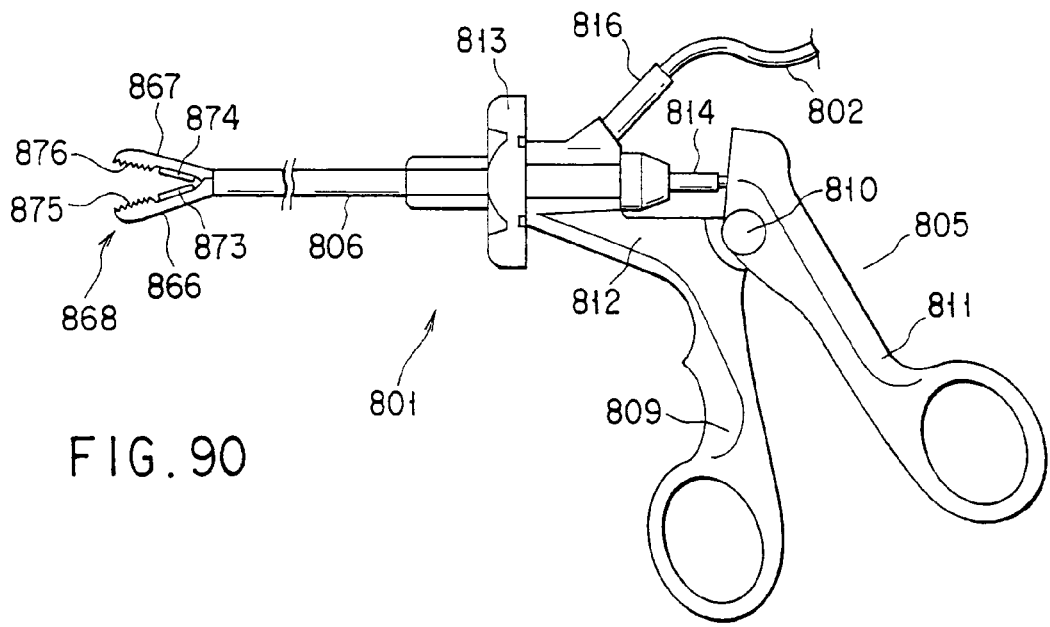
Figure 91:
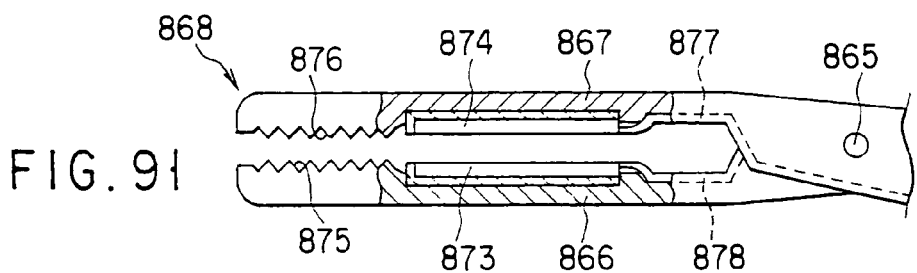
Figure 92:
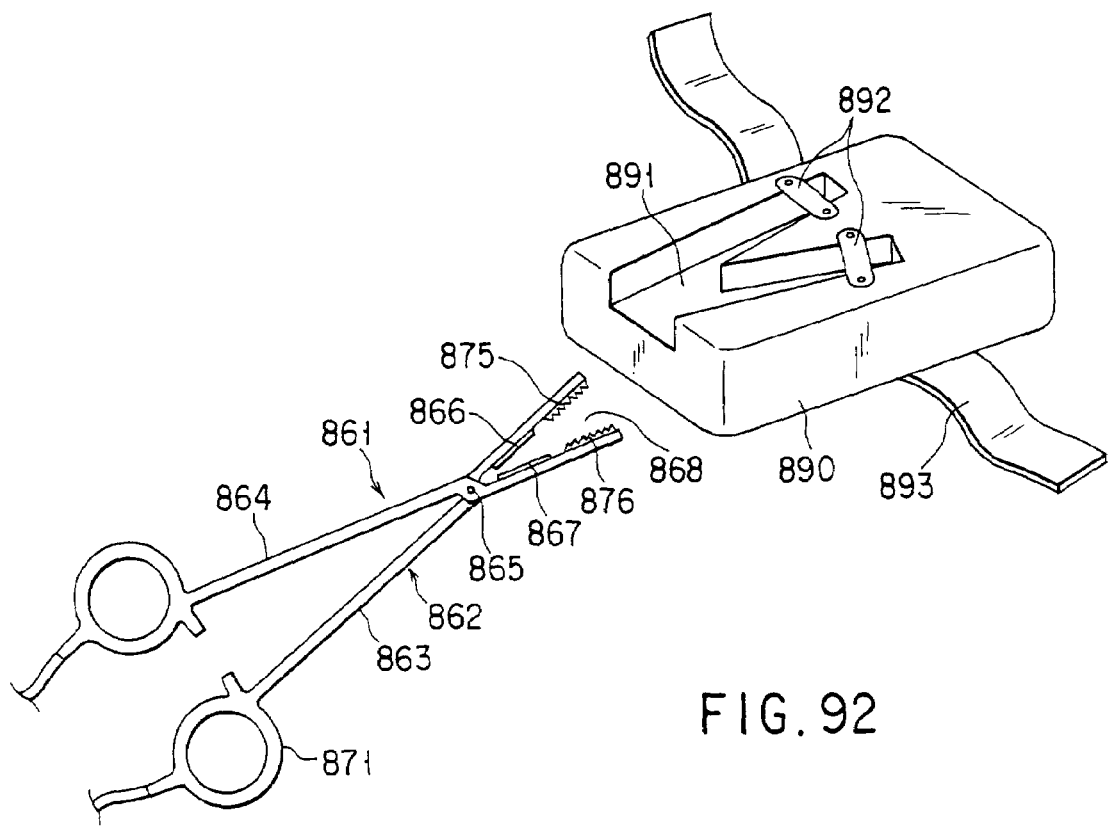
Figure 93:
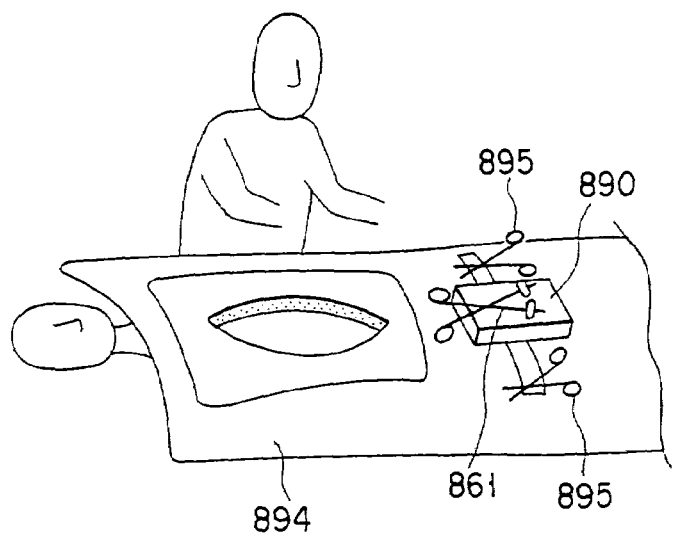

FIG. 75 is a perspective view of a thermocoagulation cutting forceps according to a fifty-fourth embodiment of the invention;

FIG. 76 is a sectional view taken along line 76-76 of FIG. 75;

FIG. 77A is a side view, partially in section, showing an open state of holding portions of a thermocoagulation cutting forceps according to a fifty-fifth embodiment of the invention;

FIG. 77B is a side view, partially in section, showing a closed state of the holding portions of the forceps of the fifty-fifth embodiment;

FIG. 78A is a side view, partially in section, showing an open state of holding portions of a thermocoagulation cutting forceps according to a fifty-sixth embodiment of the invention;

FIG. 78B is a side view, partially in section, showing a closed state of the holding portions of the forceps of the fifty-sixth embodiment;

FIG. 79A is a side view, partially in section, showing an open state of holding portions of a thermocoagulation cutting forceps according to a fifty-seventh embodiment of the invention;

FIG. 79B is a side view, partially in section, showing a closed state of the holding portions of the forceps of the fifty-seventh embodiment;

FIG. 80A is a side view, partially in section, showing an open state of holding portions of a thermocoagulation cutting forceps according to a fifty-eighth embodiment of the invention;

FIG. 80B is a side view, partially in section, showing a closed state of the holding portions of the forceps of the fifty-eighth embodiment;

FIG. 81 is a schematic structural view illustrating an entire system of a surgical instrument denoting a thermocoagulation cutting forceps according to a fifty-ninth embodiment of the present invention;

FIG. 82 is a side view showing the thermocoagulation cutting forceps according to the fifty-ninth embodiment of the present invention;

FIG. 83 is a perspective view of the holding portion of the thermocoagulation cutting forceps according to the fifty-ninth embodiment of the present invention;

FIG. 84 is a cross sectional view along the line 84-84 shown in FIG. 83;

FIG. 85 is an electrical circuit diagram of the fifty-ninth embodiment of the present invention;

FIG. 86 of a graph relating to the fifty-ninth embodiment of the present invention;

FIG. 87A is a cross sectional view showing the state that a ceramic heater is arranged in a treatment portion included in the thermocoagulation cutting forceps according to a sixtieth embodiment of the present invention;

FIG. 87B is a cross sectional view showing a first modification of the treatment portion included in the thermocoagulation cutting forceps according to the sixtieth embodiment of the present invention;

FIG. 87C is a cross sectional view showing a second modification of the treatment portion included in the thermocoagulation cutting forceps according to the sixtieth embodiment of the present invention;

FIG. 87D is a cross sectional view showing a third modification of the treatment portion included in the thermocoagulation cutting forceps according to the sixtieth embodiment of the present invention;

FIG. 87E is a cross sectional view of a gist portion exemplifying another construction of a third modification of the second holding portion included in the thermocoagulation cutting forceps according to the sixtieth embodiment of the present invention;

FIG. 87F is a cross sectional view of a gist portion exemplifying still another construction of a third modification of the second holding portion included in the thermocoagulation cutting forceps according to the sixtieth embodiment of the present invention;

FIG. 88 is a perspective view showing a thermocoagulation cutting forceps according to a sixty-first embodiment of the present invention;

FIG. 89A is a side view showing the entire scissors type coagulation treating instrument according to a sixty-second embodiment of the present invention;

FIG. 89B is a plan view showing the treatment portion of the scissors type coagulation treating instrument according to the sixty-second embodiment of the present invention;

FIG. 89C is a perspective view showing the jaw of the scissors type coagulation treating instrument according to the sixty-second embodiment of the present invention;

FIG. 90 is a side view showing the entire thermocoagulation cutting forceps according to a sixty-third embodiment of the present invention;

FIG. 91 is a cross sectional view, partly broken away, showing the treatment portion included in the thermocoagulation cutting forceps according to the sixty-third embodiment of the present invention;

FIG. 92 is a perspective view showing a housing case for housing the coagulation treating instrument according to a sixty-fourth embodiment of the present invention;

FIG. 93 is a perspective view showing how to use the housing case according to the sixty-fourth embodiment of the present invention;

FIG. 94 is a side view showing the entire ultrasonic wave coagulation cutting instrument according to a sixty-fifth embodiment of the present invention;

FIG. 95 is a perspective view showing the treatment portion according to the sixty-fifth embodiment of the present invention; and FIG. 96 is a cross sectional view at the time when the treatment portion according to the sixty-fifth embodiment of the present invention is closed.

DETAILED DESCRIPTION OF THE INVENTION

Figure 1:
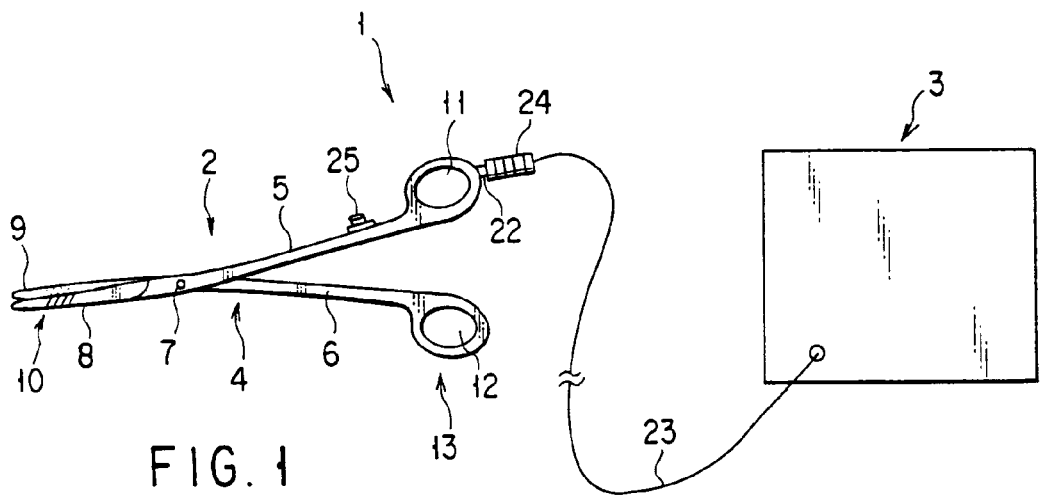
FIG. 1 is a schematic structural view illustrating an entire system of a medical treatment instrument according to a first embodiment of the present invention.

Hereinafter, a first embodiment of the present invention will be described with reference to FIGS. 1 to 5C. FIG. 1 shows a schematic configuration of the entire system of a medical treatment instrument 1 according to the present embodiment. The medical treatment instrument 1 of the present embodiment is provided with a pair of scissor forceps 2 and a generator 3 connected to this scissor forceps 2.

Figure 2:
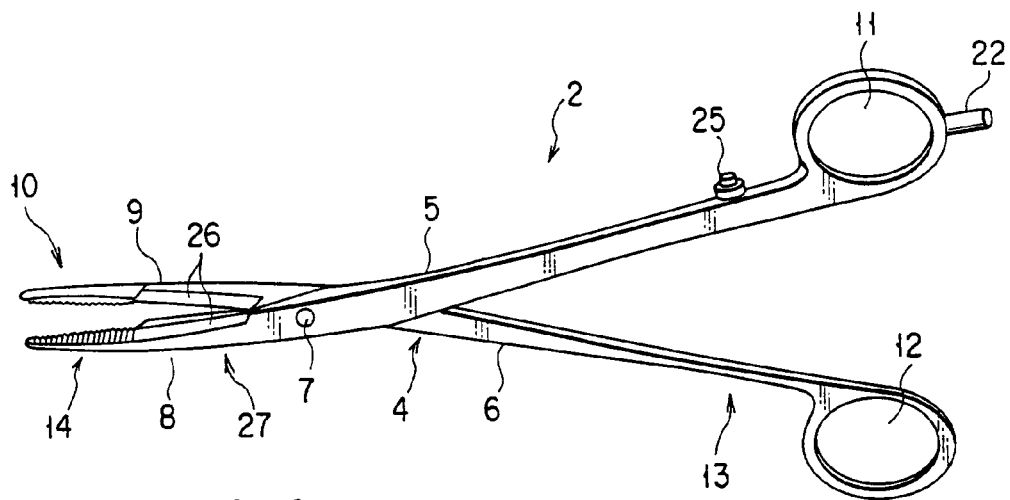
FIG. 2 is a perspective view of a scissor forceps in the medical treatment instrument according to the first embodiment.

Here, a forceps main body (treatment instrument main body) 4 of the scissor forceps 2 is provided with two scissor constituent members 5 and 6 as shown in FIG. 2. These scissor constituent members 5 and 6 are placed so that their intermediate portions substantially cross with each other. Further, a support shaft 7 rotatably linking the scissor constituent members 5 and 6 with each other is arranged at a cross section of both of these scissor constituent members 5 and 6.

In addition, a treatment portion 10 comprising a pair of opening/closing elements 8 and 9 capable of being opened or closed is formed at the tip of the forceps main body 4.

This treatment portion 10 is molded in the substantially same shape as that in a release forceps.

Further, substantially elliptical rings 11 and 12 for receiving fingers are formed at the proximal ends of the scissor constituent members 5 and 6, respectively. A frontal operating portion 13 for opening/closing a pair of opening/closing elements 8 and 9 is formed by portions of these rings 11 and 12.

Figure 3:
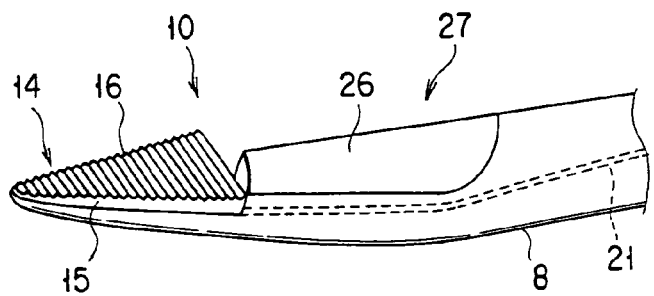
FIG. 3 is a perspective view showing a tip grasp portion and a blade portion of the scissor forceps according to the first embodiment.

At each of the opening/closing elements 8 and 9 of the forceps main body 4, a grasp portion 14 for grasping patient's body tissues is disposed at the tip side, for example, with a length of about 2 cm from the tips of the opening/closing elements 8 and 9, respectively. A substantially planar wide contact plate 15 is arranged at the inner surface side of this grasp portion 14 (an opposite surface to the other grasp portion 14), as shown in FIG. 3. This contact plate 15 is formed by a metal material with its high thermal conductivity, for example, brass. Further, a substantially serrate grasp surface 16 having a plurality of protrusions and recesses arranged thereon is formed on the outer surface of this contact plate 15. A Teflon-coating layer 17 preventing a scorch of patient's body tissues is formed on the outer surface of the contact plate 15 (contact surface with the patient's body tissues).

Figure 4:
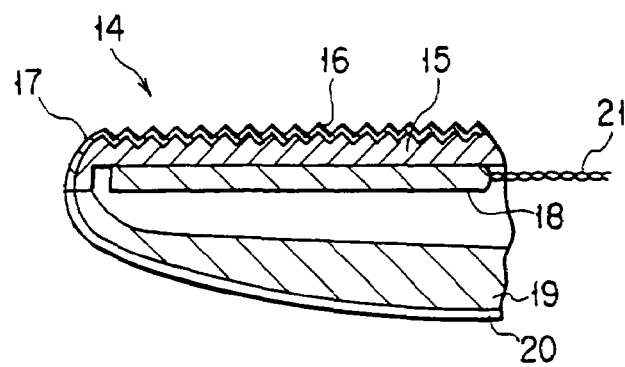
FIG. 4 is a longitudinal sectional view illustrating an internal structure of the tip grasp portion of the scissor forceps according to the first embodiment.

A heating element (heat generating section) 18 is arranged inside the grasp portion 14 of each of the opening/closing elements 8 and 9, as shown in FIG. 4. This heating element 18 is formed, for example, by a ceramic heater or a heating element current-carried and heated to generate heat such as metal resistor. This heating element 18 is fixed to the inner surface of each contact plate 15. In this manner, when the heating element 18 is current-carried, heat of the heating element 18 is transmitted via the contact plate 15 so that the patient's body tissue grasped between the grasp portions 14 is coagulated.

Further, a stainless back plate member 19, for example, is arranged at an opposite side to that of the contact plate 15 in each grasp portion 14. A coat layer 20 to which a heat resistance coating is applied is formed on the outer surface of this stainless back plate member 19.

At one end, a lead wire 21 is connected to the heating element 18. At the other end, this lead wire 21 is extended to the frontal operating portion 13 side. A cable connection portion 22 is protruded on the peripheral surface of one ring 11 at the operating portion 13. At the other end, the lead wire 21 is connected to the inner end of the cable connection portion 22.

Further, a connector 24 arranged at the other end of the connector cable 23 connected to the generator 3 at one end is detachably connected to this cable connection portion 22. When the scissor forceps 2 is used, the heating element 18 is current-carried from the generator 3 via the connector cable 23 and the lead wire 21, and the heating element 18 is current-carried so as to generate heat. At one scissor constituent member 5, an ON/OFF operation switch 25 for heat generation due to the heating element 18 is arranged in the vicinity of the ring 11.

A single-blade scissor blade (dissection portion) 26 is formed on the rear side of the grasp portion 14 in each of the opening/closing elements 8 and 9. This scissor blade 26 is molded integrally with the back plate member 19 in each grasp portion 14 by a stainless material, for example. A coat layer 20 is not formed at a portion of this scissor blade 26, and a stainless metal surface is exposed. A metal scissors dissection portion 27 for cutting a patient's body tissue by the scissor blades 26 of both of the opening/closing elements 8 and 9 is provided. Further, at the forceps main body 4 of the scissor forceps 2, a portion other than each grasp portion 14 and scissor blade 26 is formed by heat resistance plastic, for example.

Now, an operation of the medical treatment instrument 1 with the above structure according to the present embodiment will be described. Here, an example of work of treating a lesion in blood vessels or the like brought into close contact with patient's body tissues such as internal organs by using the scissor forceps 2 according to the present embodiment will be described with reference to FIGS. 5A to 5C.

Figure 5A:
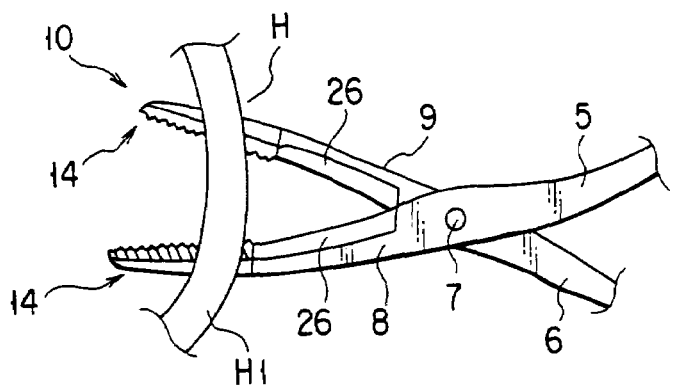
FIG. 5A is a view for illustrating a release process of a blood vessel using the scissor forceps according to the first embodiment.

First, as shown in FIG. 5A, a treatment portion 10 at the tip of the scissor forceps 2 is inserted between a blood vessel H1 brought in close contact with a patient's body tissue H such as internal organs and the patient's body tissue H. At this time, while a pair of opening/closing elements 8 and 9 of the treatment portion 10 is closed in advance, these elements are both inserted between the blood vessel H1 and the patient's body tissue H. Then, an interval between the blood vessel H1 and the patient's body tissue H is released by opening a pair of the opening/closing elements 8 and 9.

Figure 5B:
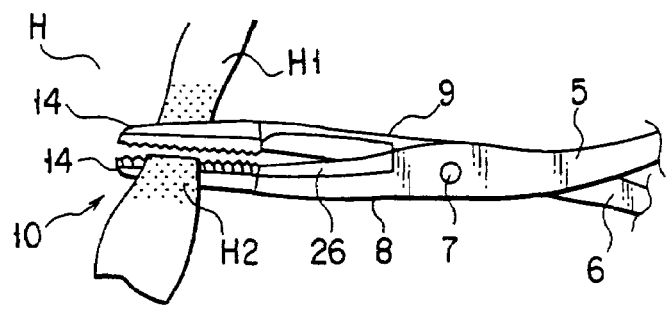
FIG. 5B is a view for illustrating a coagulation process of a blood vessel.

Thereafter, the blood vessel H1 released as shown in FIG. 5B is grasped between the grasp portions 14 of the opening/closing elements 8 and 9. At this time, the blood vessel H1 is maintained while being compressed between the grasp portions 14 at a proper pressure.

In this state, a switch 25 is turned ON, and the heating element 18 is current-carried and heated. At this time, heat of the heating element 18 is transmitted to the blood vessel H1 between the grasp portions 14 via the contact plate 15. In this manner, a wall of the blood vessel H1 grasped between the grasp portions 14 is coagulated and welded, and a coagulated-welded portion H2 is formed.

In addition, after the wall of the blood vessel H1 has been coagulated and welded, the coagulated-welded portion H2 of this blood vessel H1 is separated by the scissor blade 26 of the dissection portion 27 on the rear side of the grasp portion 14 in each of the opening/closing elements 8 and 9.

With the above structure, the following effect is obtained. That is, in the medical treatment instrument 1 according to the present embodiment, a substantially planar wide contact plate 15 is arranged at the grasp portion 14 of each of the opening/closing elements 8 and 9 of the forceps main body 4, so that the blood vessel H1 is grasped between the two contact plates 15. Thus, the heating element 18 on the tip of the treatment portion 10 is current-carried and heated, whereby the patient's body tissue such as blood vessel H1 grasped between a pair of the grasp portions 14 can be thermally coagulated reliably by heat of the heating element 18.

Further, the patient's body tissue such as blood vessel H1 has been thermally coagulated, the coagulated-welded portion H2 is cut by the dissection portion 27 using the metal scissor blade 26 on the rear side of the grasp portion 14 in the treatment portion 10. Unlike a case in which a ceramic based scissors portion is used, there is less possibility that the dissection capability is gradually degraded due to a friction between the slide portions of the scissors portion during in use. Thus, the degradation of the dissection capability of the dissection portion 27 due to the scissor blade 26 while the scissor forceps 2 is used is minimized, and the sharpness of the dissection portion 27 can be maintained for a long period of time.

In the present embodiment, work of releasing the blood vessel H1 brought into close contact with the patient's body tissue H such as internal organ from the patient's body tissue H; work of coagulating and welding the wall of the blood vessel H1; or work of separating the suspected coagulated-welded portion H2 of the blood vessel H1 can be performed by a single scissor forceps 2. Thus, unlike a case in which these work are performed by using respective individual treatment instruments, work of replacing one treatment instrument with another can be eliminated, thus improving usability. Further, the number of treatment instruments used in the above treatments can be reduced, making it advantageous in cost efficiency.

In the present embodiment, at the forceps main body 4 of the scissor forceps 2, a portion other than each grasp portion 14 and scissor blade 26 is formed by heat resistance plastic, for example. Thus, there is achieved an effect that the patient's body tissues adjacent to a treatment portion treated by each grasp portion 14 and the scissor blade 26 can be protected, and the surgeon's hands can also be protected.

Figure 5C:
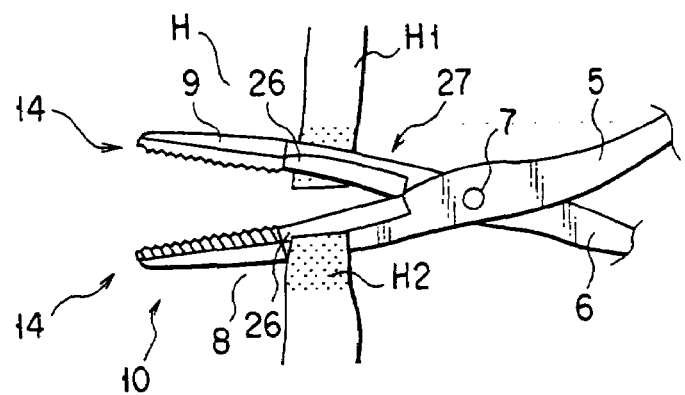
FIG. 5C is a view for illustrating a dissection process of a blood vessel.
Figure 6:
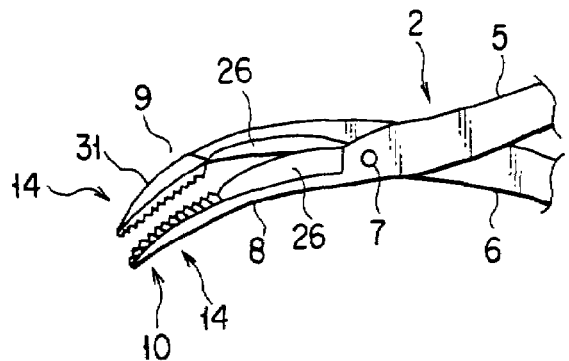
FIG. 6 is a perspective view showing a structure of essential portions of the scissor forceps according to a second embodiment of the present invention.

FIG. 6 shows a second embodiment of the present invention. In the present embodiment, a configuration of the scissor forceps 2 in the medical treatment instrument 1 according to the first embodiment (refer to FIGS. 1 to 5C) is modified as follows:

That is, in the scissor forceps 2 according to the present embodiment, a curve portion 31 gently curved in the substantial arc shape is formed at the grasp portion 14 disposed at the tip of the forceps main body 4. A configuration of the other portion is similar to that of the first embodiment. Like elements identical to those in the first embodiment is represented by like reference numerals, and a description thereof will be omitted here.

According to the present embodiment, an effect substantially similar to that of the first embodiment is obtained. Further, in the present embodiment, in particular, a curve portion 31 gently curved in the substantial arc shape is formed at the grasp portion 14 disposed at the tip of the forceps main body 4 of the scissor forceps 2. Thus, as shown in FIG. 5A, work of inserting the treatment portion 10 at the tip of the scissor forceps 2 between the blood vessel H1 brought into close contact with the patient's body tissue H such as internal organ and the patient's body tissue H can be performed more easily.

Figure 7:
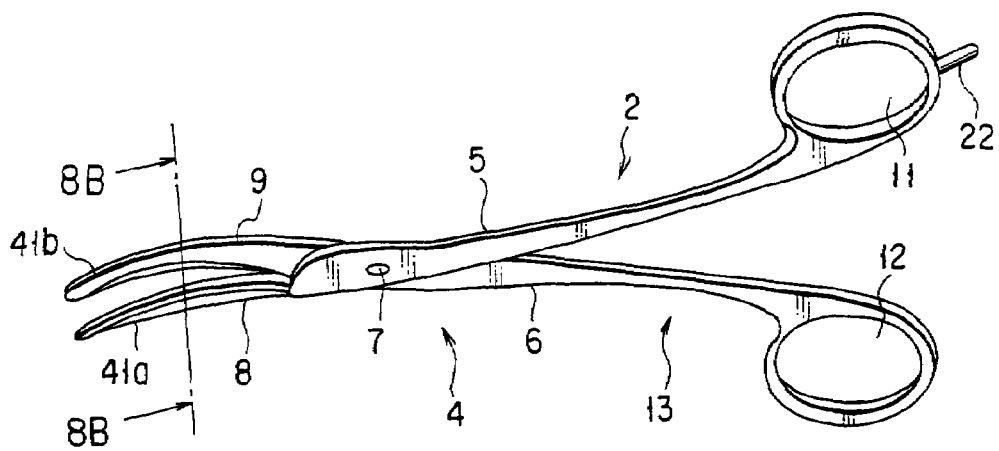
FIG. 7 is a perspective view showing a scissor forceps according to a third embodiment of the present invention.
Figure 8A:
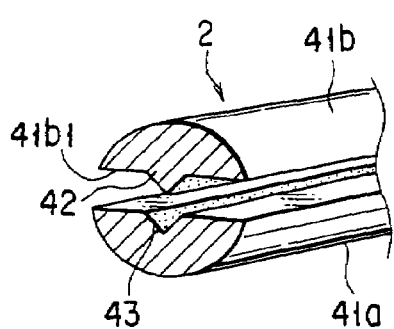
FIG. 8A is a sectional perspective view showing a tip grasp portion of the scissor forceps according to the third embodiment.
Figure 8B:
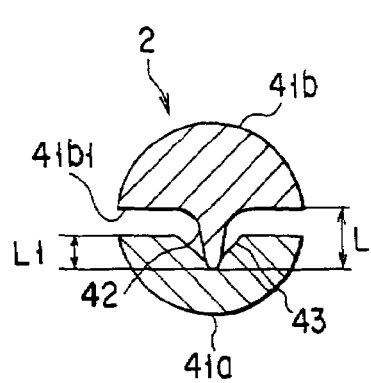
FIG. 8B is a cross sectional view taken along the line VIIIB-VIIIB.

FIGS. 7, 8A and 8B show a third embodiment of the present invention. In the present embodiment, a configuration of the scissor forceps 2 in the medical treatment instrument 1 according to the first embodiment (refer to FIGS. 1 to 5C) is modified as follows:

That is, in the scissor forceps 2 of the present embodiment, grasp portions 41a and 41b gently curved in the substantial arc shape are formed, respectively, at the portions of a pair of opening/closing elements 8 and 9 at the tip side of the forceps main body a rather than the support shaft 7.

Further, as in the first embodiment, the heating element 18 shown in FIG. 4 is arranged inside each of the grasp portions 41a and 41b of each of the opening/closing elements 8 and 9. When the heating element 18 is current-carried, heat of this heating element 18 is transmitted to the surface side of the grasp portions 41a and 41b via the contact plate 15 so that the patient's body tissue grasped between the grasp portions 41a and 41b of each of the opening/closing element 8 and 9 is coagulated.

In addition, in the scissor forceps 2 of the present embodiment, as shown in FIGS. 8A and 8B, a dissection blade portion 42 for cutting the patient's body tissue toward one grasp portion 41a side is protruded toward the other grasp portion 41b side. At one grasp portion 41b, this blade portion 42 is disposed at the substantial center site of the opposite surface 41b1 to the other grasp portion 41a, and is extended in longitudinal direction of this grasp portion 41b.

Further, a recess-shaped long groove portion (recess portion) 43 meshed with the blade portion 42 of the grasp portion 41b is formed on the other grasp portion 41a side. Here, as shown in FIG. 8B, a depth L1 of the long groove portion 43 is set to be lower than a height L2 of the blade portion 42 of the grasp portion 41b (L1<L2). When the frontal operating portion 13 is firmly gripped and moved in a direction in which an interval between the grasp portions 41a and 41b is closed, a top part of the blade portion 42 of the grasp portion 41b abuts against the inner bottom of the long groove portion 43 so as to maximize the pressure of this abutment portion.

Next, an operation in the above structure will be described. When a lesion in a blood vessel or the like brought into close contact with the patient's body tissue such as internal organ is treated by using the scissor forceps 2 of the present embodiment, a process for releasing the blood vessel H1 and the patient's body tissue H from each other shown in FIG. 5A is performed through operation similar to that in the first embodiment.

Thereafter, the blood vessel H1 released as shown in FIG. 5B is grasped between the grasp portions 41a and 41b of the opening/closing elements 8 and 9 respectively in the scissor forceps 2. At this time, the blood vessel H1 is compressed between the grasp portions 41a and 41b with a relatively gentle pressure to an extent such that the blood vessel H1 is not cut by the blade portion 42 of the grasp portion 41b.

In this state, the heating element 18 is current-carried and heated, whereby heat of the heating element 18 is transmitted to the blood vessel H1 between the grasp portions 41a and 41b via the contact plate 15. In this manner, the wall of the blood vessel H1 grasped between the grasp portions 41a and 41b is coagulated and welded, and the coagulated-welded portion H2 is formed.

Further, after the wall of the blood vessel H1 has been coagulated and welded, the frontal operating portion 13 is firmly gripped, and is moved in a direction in which an interval between the grasp portions 41a and 41b is closed. At this time, a top part of the blade portion 42 of the grasp portion 41b is strongly pressed in a direction in which the top part abuts against the inner bottom of the long groove portion 43, whereby the coagulated-welded portion H2 is separated by the blade portion 42 of the grasp portion 41b as shown in FIG. 5C.

With the above structure, the following effect is obtained. That is, in the scissor forceps 2 of the present embodiment, when the released blood vessel H1 is grasped between the grasp portions 41a and 41b of the opening/closing elements 8 and 9 respectively, the blood vessel H1 is compressed between the grasp portions 41a and 41b with a relatively gentle pressure to an extent such that the blood vessel H1 is not cut by the blade portion 42 of the grasp portion 41b. In this state, the heating element 18 is current-carried and heated, whereby the wall of the blood vessel H1 grasped between the grasp portions 41a and 41b can be coagulated and welded. Further, after the wall of the blood vessel H1 has been coagulated and welded, the frontal operating portion 13 is firmly gripped, and is further moved in a direction in which an interval between the grasp portions 41a and 41b is closed. Then, the top part of the blade portion 42 of the grasp portion 41b is strongly pressed in a direction in which the top part abuts against the inner bottom of the long groove portion 43 of the grasp portion 41a, whereby the coagulated-welded portion H2 of the blood vessel H1 can be separated by the blade portion 42 of the grasp portion 41b.

Therefore, in the scissor forceps 2 of the present embodiment, as is substantially similar to the first embodiment, work of releasing the blood vessel H1 brought into close contact with the patient's body tissue H such as internal organ from the patient's body tissue H1; work of coagulating and welding the wall of the blood vessel H1; or work of separating the coagulated-welded portion H2 of the blood vessel H1 can be performed by a single scissor forceps 2. Thus, unlike a case in which each of these work is performed by using the respective individual treatment instruments, work of replacing one treatment instrument with another can be eliminated, making it advantageous in usability and cost efficiency.

Further, also in the scissor forceps 2 of the present embodiment, the coagulated-welded portion H2 of the blood vessel H1 is cut by the metal blade portion 42. Thus, there is less possibility that the dissection capability is gradually degraded due to a friction between the slide portions of the scissors portion while in use when a ceramic scissors portion is used. Therefore, in the scissor forceps 2 of the present embodiment also, as is substantially similar to the first embodiment, the degradation of the dissection capability of the blade portion 42 while the scissor forceps 2 is used can be reduced, and the sharpness of the blade portion 42 can be maintained for a long period of time.

Figure 8C:
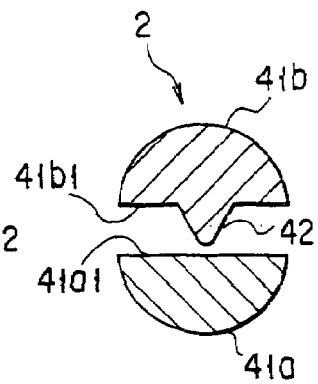
FIG. 8C is a cross sectional view of essential portions showing a modified example of the scissor forceps according to the third embodiment.

FIG. 8C shows a modified example of the scissor forceps 2 according to the third embodiment (refer to FIGS. 7, 8A and 8B). In the scissor forceps 2 of the present embodiment, at one grasp portion 41b side, the dissection blade portion 42 for cutting the patient's body tissue is protruded toward the other grasp portion 41a side. At one grasp portion 41b side, this blade portion 42 is disposed at the substantial center of an opposite surface to the other grasp portion 41a, and is extended in longitudinal direction of this grasp portion 41b.

Further, a smooth contact surface 41a1 is formed on the other grasp portion 41a side. When the frontal operating portion 13 is firmly gripped, and is moved in a direction in which an interval between the grasp portions 41a and 41b is closed, the top part of the blade portion 42 of the grasp portion 41b abuts against the contact surface 41a1 so as to maximize the pressure of this abutment portion.

FIGS. 9A and 9B show a fourth embodiment of the present invention. FIG. 9A shows a schematic structure of the entire surgical treatment instrument 51 used for surgical operation under endoscope that is a medical treatment instrument of the present embodiment. A treatment instrument 51 of the present embodiment is provided with an elongated insert portion 52 to be inserted into the patient body through trocar (not shown); and a frontal operating portion 53 coupled with the proximal end of this insert portion 52.

In addition, the insert portion 52 is provided with a tubular insert tube body 54. A driving shaft 55 relatively driven in axial direction of the insert portion 52 is inserted into this insert tube body 54. Further, a treatment portion 56 is arranged at the tip of the insert portion 52. This treatment portion 56 is provided with a pair of grasp members (opening/closing elements) 57a and 57b capable of being opened and closed. Here, a pair of the grasp members 57a and 57b is coupled with the tip of the driving shaft 55 via a driving mechanism (not shown) such as cam mechanism. An interval between the grasp members 57a and 57b of the treatment portion 56 is driven to be opened and closed via the driving mechanism together with retracting movement of the driving shaft 55.

In addition, the grasp member 57 of the present embodiment is structured in a manner substantially similar to that in the grasp portion 14 of each of the opening/closing elements 8 and 9 of the scissor forceps 2 in the first embodiment (refer to FIGS. 1 to 4).

That is, as in the first embodiment, the heating element 18 shown in FIG. 4 is arranged inside the grasp members 57a and 57b of the present embodiment. When the heating element 18 is current-carried and heated, heat of this heating element 18 is transmitted to the surface side of the grasp members 57a and 57b via the contact plate 15 so that the patient's body tissue grasped between the grasp members 57a and 57b is coagulated.

In the treatment instrument 51 of the present embodiment, each single-blade scissor blade (dissection portion) 26' is formed on the rear side of the grasp members 57a and 57b.

In addition, the frontal operating portion 53 is provided with an operating portion main body 58 for rotatably holding the proximal end of the insert portion 52. A fixing handle 59 is formed integrally with this operating portion main body 58. A rotation operation knob 60 for rotating the proximal end of the insert portion 52 is arranged at the tip of the operating portion main body 58.

Further, a link portion of a movable handle 61 is rotatably linked with the fixing handle 59 via the support shaft 62. The proximal end of the driving shaft 55 is coupled with this movable handle 61.

Furthermore, a first finger receiving ring 59a capable of inserting the operator's finger thereinto is formed at the end of the fixing handle 59. Still furthermore, a second finger receiving ring 61a capable of inserting the operator's finger thereinto is formed similarly at the end of the movable handle 61. The driving shaft 55 is driven to be retracted along axial direction together with opening/closing (rotating movement) operation of the movable handle 61 for the fixing handle 59 so that an interval between the grasp members 57a and 57b of the treatment portion 56 is driven to be opened and closed.

Now, an operation in the above structure will be described. When the surgical treatment instrument 51 of the present embodiment is used, the operator's fingers are inserted into the ring 59a of the fixing handle 59 and into the ring 61a of the movable handle 61, respectively. In this state, the movable handle 61 is rotated with respect to the fixing handle 59. At this time, together with the rotating movement of the movable handle 61, the driving shaft 55 is moved in axial direction relative to the insert tube body 54 of the insert portion 52, and an interval between the grasp members 57a and 57b of the treatment portion 56 at the tip of the insert portion 52 is driven to be opened and closed via a driving mechanism.

As in the first embodiment, in the case where a lesion in a blood vessel or the like brought into close contact with the patient's body tissue such as internal organ is treated by using the treatment instrument 51 of the present embodiment, a process for releasing the blood vessel H1 and the patient's body tissue H shown in FIG. 5A is performed through operation similar to that in the first embodiment.

Thereafter, the blood vessel H1 released as shown in FIG. 5B is grasped between the grasp members 57a and 57b in the treatment instrument 51. At this time, the blood vessel H1 is maintained while it is compressed between the grasp members 57 with a proper pressure.

In this state, the heating element 18 is current-carried and heated, whereby heat of the heating element 18 is transmitted to the blood vessel H1 between the grasp members 57 via the contact plate 15. In this manner, the wall of the blood vessel H1 grasped between the grasp members 57 is coagulated and welded, and the coagulated-welded portion H2 is formed.

Further, after the wall of the blood vessel H1 has been coagulated and welded, the coagulated-welded portion H2 is separated by the scissor blade 26' on the rear side of the grasp members 57a and 57b.

When the blood vessel H1 released by the treatment instrument 51 having the above structure of the present embodiment is grasped between the grasp members 57a and 57b in the treatment instrument 51, the blood vessel H1 is grasped between two contact plates 15 of the grasp members 57a and 57b. Thus, the heating element 18 is current-carried and heated, thereby the wall of the blood vessel H1 grasped between the grasp members 57a and 57b can be coagulated and welded reliably.

Furthermore, after the wall of the blood vessel H1 has been coagulated and welded, the coagulated-welded portion H2 of the blood vessel H1 is cut by the metal scissor blade 26' on the rear side of the grasp members 57a and 57b. Thus, unlike a case in which the ceramic based scissors portion is used, there is less possibility that the dissection capability is gradually degraded due to a friction between the slide portions of the scissors portion during in use. Therefore, even in the treatment instrument 51 of the present instrument, as is substantially similar to the first and third embodiments, work of releasing the blood vessel H1 brought into close contact with the patient's body tissue H such as internal organ from the patient's body tissue H; work of coagulating and welding the wall of the blood vessel H1; or work of separating the coagulated-welded portion H2 of the blood vessel H1, or the like can be performed by a single treatment instrument 51. Thus, unlike the case in which each of these work is treated by using respective individual treatment instruments, work of replacing the treatment instrument can be eliminated, making it advantageous in usability and cost efficiency.

FIG. 10 shows a fifth embodiment of the present invention. In the present embodiment, control means 71 of the heating element 18 of the scissor forceps 2 in the medical treatment instrument 1 is provided according to the first embodiment. The control means 71 of the present embodiment is provided with a temperature control portion 72 connected to the heating element 18 of the scissor forceps 2. A CPU 74 is connected to this temperature control portion 72 via an amplifier 73. Further, an operating panel 75 for temperature setting is connected to the CPU 74.

The heating element 18 mounted on the scissor forceps 2 of the present embodiment is formed by a metal resistor such as molybdenum in which a resistance value is changed due to a temperature, and the temperature and resistance value change linearly.

In the temperature control portion 72 of the present embodiment, a current amplified by the amplifier 73 is controlled, whereby the resistance value of the heating element 18 of the scissor forceps 2, i.e., the temperature of the heating element 18 can be adjusted within an arbitrary temperature range, for example, within the range from 60° C. to 150° C.

FIG. 11 shows a sixth embodiment of the present invention. In the present embodiment, a structure of the medical treatment instrument 1 according to the first embodiment (refer to FIGS. 1 to 5C) is modified as follows:

That is, in the present embodiment, a battery housing portion 81 is connected to a cable connection portion 22 of the finger insert ring 11 of one scissor constituent member 5 in the scissor forceps 2 of the first embodiment so that a driving current is supplied from a battery housed in the battery housing portion 81 to the heating element 18 of the scissor forceps 2.

With the above structure, a generator 3 used in the medical treatment instrument 1 of the first embodiment is not required, and thus, the connector cable 23 connecting the scissor forceps 2 and the generator 3 is not also required. Therefore, unlike the first embodiment, there is no possibility that movement of the scissor forceps 2 is restricted by the connector cable 23, and thus, there is an effect that operability of the scissor forceps 2 can be improved more significantly.

Figure 12:
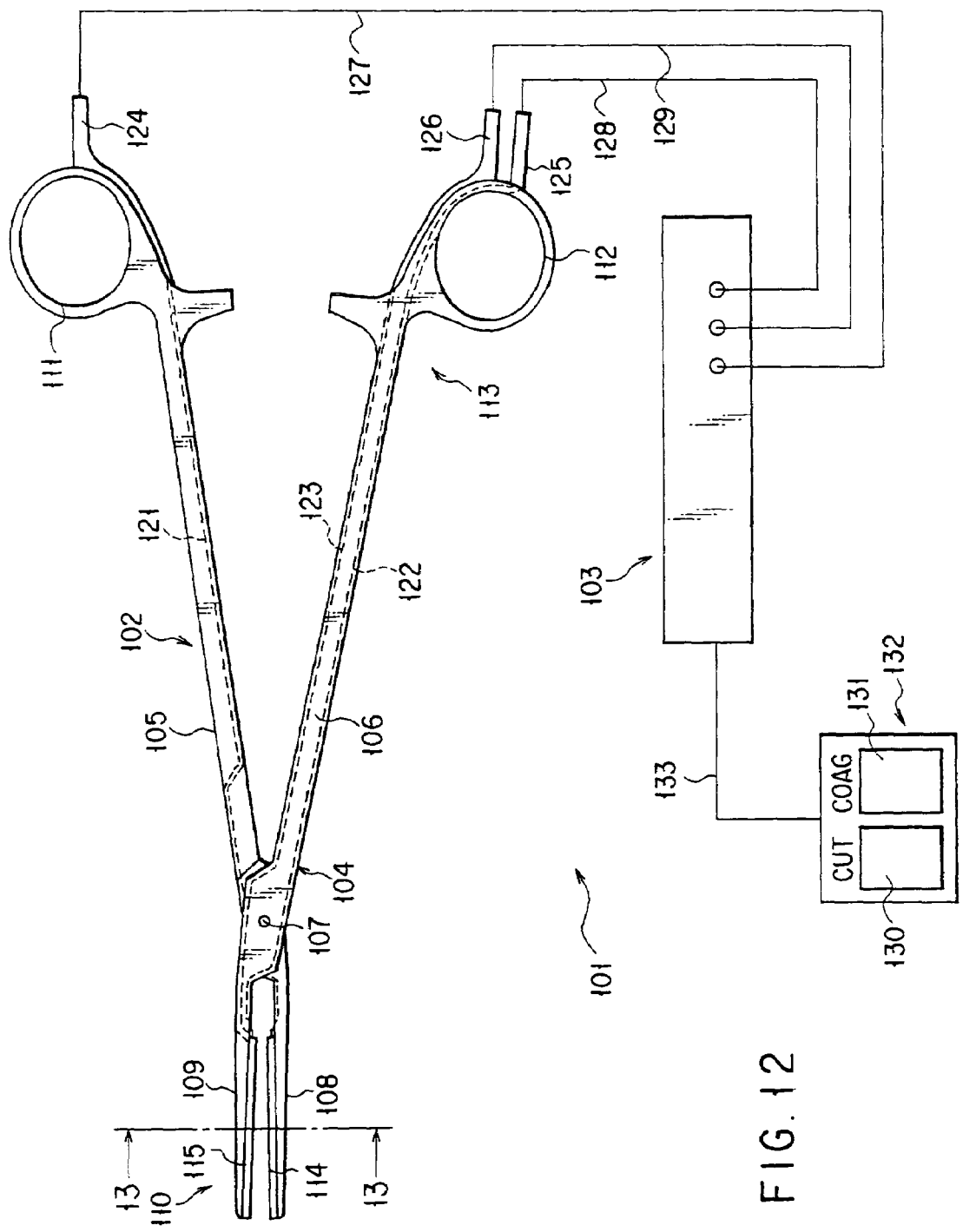
FIG. 12 is a schematic structural view showing the entire system of the medical treatment instrument according to a seventh embodiment of the present invention.
Figure 13:
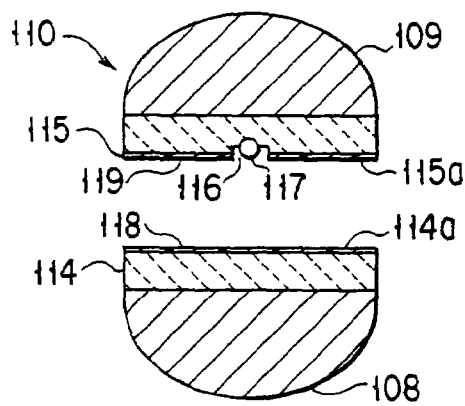
FIG. 13 is a cross sectional view taken along the line XIII-XIII of FIG. 12.

FIGS. 12 and 13 show a seventh embodiment of the present invention. FIG. 12 shows a schematic structure of the entire system of a medical treatment instrument 101 according to the present embodiment. The system of the medical treatment instrument 101 according to the present embodiment is provided with a forceps 102 and a power supply unit 103 connected to this forceps 102.

A main body 104 of the forceps 102 is provided with two scissor constituent members 105 and 106. These scissor constituent members 105 and 106 are placed in a state in which the intermediate portions substantially cross with each other. Further, a support shaft 107 is arranged at the cross section of these scissor constituent members 105 and 106 to rotatably link the scissor constituent members 105 and 106.

In addition, a treatment portion 110 comprising a pair of grasp portions 108 and 109 capable of being opened and closed, which grasps the patient's body tissue, is arranged at the tip of the forceps main body 104. This treatment portion 110 is molded in the substantially same shape as the release forceps.

Further, the substantially elliptical finger insert rings 111 and 112 are formed at the proximal ends of the scissor constituent members 105 and 106, respectively. The frontal operating portion 13 for opening/closing a pair of grasp portions 108 and 109 is formed by the portions of these finger insert rings 111 and 112.

In addition, at the grasp portions 108 and 109 of the forceps main body 104, as shown in FIG. 13, the substantially planar, wide rectangular coagulation treatment heat generating portions 114 and 115 are arranged, respectively, on the contact surface side with the patient's body tissue. These coagulation treatment heat generating portions 114 and 115 are formed by a heating element current-carried to generate heat such as ceramic heater or PTC heater (heater formed by a positive temperature coefficient material).

A substantially smooth surface 114a and 115a are formed on the contact surface side with the patient's body tissue in the coagulation treatment heat generating portion 114, 115 of the grasp portions 108 and 109.

A recess portion 116 extended along the centerline direction of the grasp portion 109 at the substantially center site of a smooth surface 115a is formed at the coagulation treatment heat generating portion 115 on the grasp portion 109 side. A dissection treatment heat generating portion 117 is arranged in this recess portion 116. This dissection treatment heat generating portion 117 is such as nichrome wire, and is formed by a sectional, substantially circular heating wire current-carried to generate heat. The outer end surface of the dissection treatment heat generating portion 117 is located so as to be substantially coincident with a smooth surface 115a on the outer surface of the coagulation treatment heat generating portion 115.

Further, a Teflon-coating layers 118 and 119 for preventing a scorch of the patient's body tissue are formed, respectively, at the smooth outer surfaces 114a and 115a (contact surface with the patent's body) of the coagulation treatment heat generating portions 114 and 115.

As shown in FIG. 1, a single lead wire 121 is arranged at one scissor constituent member 105, and two lead wires 122 and 123 are arranged, respectively, at the other scissor constituent member 106. At the tip, the lead wire 121 is connected to the coagulation treatment heat generating portion 114. Further, at the tip, the lead wire 122 is connected to the coagulation treatment heat generating portion 115. Furthermore, at the tip, the lead wire 123 is connected to the dissection treatment heat generating portion 117.

A single cable connection portion 124 is protruded on the peripheral surface of the finger insert ring 111 on the scissor constituent member 106 side. Further, two cable connection portions 125 and 126 are protruded on the peripheral surface of the finger insert ring 12 on the scissor constituent member 106 side. A proximal end of the lead wire 121 is connected to the cable connection portion 124 on the scissor constituent member 105 side, and the lead wires 122 and 123 are connected, respectively, to the cable connection portions 125 and 126 on the scissor constituent member 106.

Further, each of the connector cables 127, 128, and 129, one end of which is connected to a power supply unit 103, is detachably connected to each of these cable connection portions 124, 125, and 126 at the other end. A foot switch 132 is connected to the power supply unit 103 via a cable 133. This foot switch 132 is provided with a dissection output operating portion 130 and a coagulation output operating portion 131.

Now, an operation of the medical treatment instrument 101 with the above structure according to the present embodiment will be described. First, the treatment portion 110 at the tip of the forceps 102 is inserted into the patient's body tissue including the site targeted for treatment such as blood vessel (not shown) while it is closed. Thereafter, a pair of grasp portions 108 and 109 is opened, whereby the site targeted for treatment such as blood vessel is released from the other patient's body tissue and is exposed.

Subsequently, the released blood vessel or the like is grasped between the grasp portions 108 and 109 of the forceps 102 while it is compressed with a proper pressure suitable to coagulating treatment. In this state, the coagulation output operating portion 131 of the foot switch 132 is operated. In this manner, the coagulation treatment heat generating portions 114 and 115 are current-carried and heated. At this time, a site targeted for treatment such as blood vessel grasped between the grasp portions 108 and 109 is coagulated and treated by heat of the coagulation treatment heat generating portions 114 and 115, and is sufficiently thermally coagulated.

Thereafter, the dissection output operating portion 130 of the foot switch 132 is subsequently operated. In this manner, the dissection treatment heat generating portion 117 is current-carried and heated. This dissection treatment heat generating portion 117 is heated at a high temperature in comparison with the coagulation treatment heat generating portions 114 and 115. Thus, a part of the site targeted for treatment such as coagulated blood vessel is locally heated and cut by heat of the dissection treatment heat generating portion 117.

With the above structure, the following effect is obtained. That is, in the medical treatment instrument 101 of the present embodiment, the wide coagulation treatment heat generating portions 114 and 115 are arranged, respectively, at the grasp portions 108 and 109 of the forceps main body 104. Thus, a site targeted for treatment such as blood vessel grasped between the grasp portions 108 and 109 of the forceps main body 104 can be thermally coagulated reliably due to heat of these coagulation treatment heat generating portions 114 and 115 while it is compressed with a proper pressure.

Further, a recess portion 116 is formed on a smooth surface 115a of the coagulation treatment heat generating portion 115 on the grasp portion 109 side, and the dissection treatment heat generating portion 117 is arranged in this recess portion 115. After a site targeted for treatment such as blood vessel has been thermally coagulated due to heat of the coagulation treatment heat generating portions 114 and 115, the tissues of the site targeted for treatment such as coagulated blood vessel can be cut immediately due to heat of the dissection treatment heat generating portion 117. Therefore, unlike a case in which the patient's body tissue is cut by a blade, there is less possibility that the cutting capability is gradually degraded by repeatedly using the blade, making it impossible to reuse the blade, thereby making it advantageous in cost efficiency.

Figure 14A:
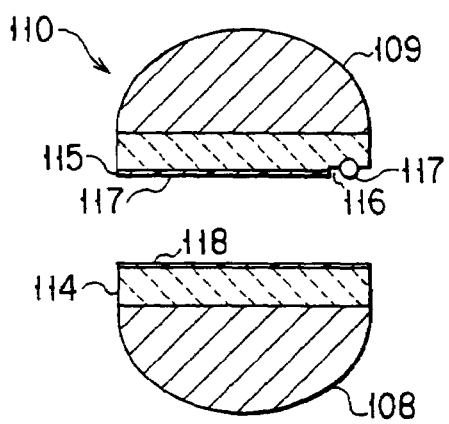
FIG. 14A is a longitudinal sectional view of essential portions showing an eighth embodiment of the present invention.

FIG. 14A shows an eighth embodiment of the present invention. In the present embodiment, a structure of the treatment portion 110 at the tip of the forceps 102 in the medical treatment instrument 101 of the seventh embodiment (refer to FIGS. 12 and 13) is modified as follows:

That is, in the present embodiment, the recess portion 116 is disposed at the side end of the smooth surface 115a in the coagulation treatment heat generating portion 115 on the grasp portion 109 side, and the dissection treatment heat generating portion 117 is arranged in this recess portion 116. The structures of the other portions are similar to those in the seventh embodiment.

Now, an operation in the above structure will be described. When the forceps 102 of the present embodiment is used to perform treatment in a way similar to that in the seventh embodiment, the following work are performed. First, the forceps 102 is operated in accordance with the procedure similar to that in the seventh embodiment to release the site targeted for treatment such as blood vessel that is a tissue in the patient's body cavity. The released blood vessel or the like is grasped while it is compressed between the grasp portions 108 and 109 with a proper pressure suitable to coagulating treatment. In this state, the coagulation treatment heat generating portions 114 and 115 are current-carried and heated, and the site targeted for treatment such as blood vessel between the grasp portions 108 and 109 is thermally coagulated.

Thereafter, after the coagulation state has been confirmed by opening the grasp portions 108 and 109, the dissection treatment heat generating portion 117 is subsequently set according to the center position of the coagulated site targeted for treatment, and the grasp portions 108 and 109 are closed again. In this state, the dissection output operating portion 130 of the foot switch 132 is operated. In this manner, the dissection treatment heat generating portion 117 is current-carried and heated, and a part of the site targeted for treatment such as coagulated blood vessel is locally heated and cut due to heat of the dissection treatment heat generating portion 117.

With the above structure, the following effect is obtained. That is, in the forceps 102 of the present embodiment, the dissection treatment heat generating portion 117 on the grasp portion 109 side is disposed at the side end on the coagulation treatment heat generating portion 115. Thus, the treatment portion 110 at the tip of the forceps 102 is visually checked transversely, whereby the dissection treatment heat generating portion 117 on the grasp portion 119 side can be easily checked. Therefore, in the case where the coagulated patient's body tissue is cut, as in the case of operating the scissors, the cutting position can be easily aligned by the patient's intention, and cutting operation can be performed safely.

Figure 14B:
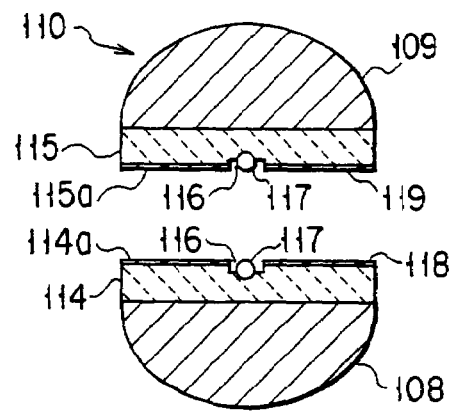
FIG. 14B is a longitudinal sectional view of essential portions showing a ninth embodiment of the present invention.

FIG. 14B shows a ninth embodiment of the present invention. In the present embodiment, a structure of the treatment portion 110 at the tip of the forceps 102 in the medical treatment instrument 101 of the seventh embodiment (refer to FIGS. 12 and 13) is modified as follows:

That is, in the seventh embodiment, there is shown a structure in which the dissection treatment heat generating portion 117 is arranged at only the coagulation treatment heat generating portion 115 only. In contrast, in the present embodiment, in addition to this structure, the recess portion 116 extended along the centerline direction of the grasp portion 108 is formed at the substantial center site of the smooth surface 114a similarly, and the dissection treatment heat generating portion 117 is arranged in this recess portion 116.

Now, an operation in the above structure will be described. When the forceps 102 of the present embodiment is used to perform treatment in a manner similar to that in the seventh embodiment, the following work are performed. First, the forceps 102 is operated in accordance with the procedure similar to that in the seventh embodiment to release a site targeted for treatment such as blood vessel that is a tissue in the patient's body cavity. Then, the released blood vessel or the like is grasped between the grasp portions 108 and 109 of the forceps 102 while it is compressed with a proper pressure suitable to coagulating treatment. In this state, the coagulation treatment heat generating portions 114 and 115 are current-carried and heated, and a site targeted for treatment such as blood vessel between the grasp portions 108 and 109 is thermally coagulated.

Thereafter, the dissection output operating portion 130 of the foot switch 132 is subsequently operated. In this manner, the dissection treatment heat generating portions 117 of both of the grasp portions 108 and 109 are current-carried and heated simultaneously. At this time, a part of the site targeted for treatment such as coagulated blood vessel is locally heated and cut by heat of the dissection treatment heat generating portions 117 on both sides.

With the above structure, the following effect is obtained. That is, in the forceps 102 of the present embodiment, the dissection treatment heat generating portions 117 are arranged, respectively, at the coagulation treatment heat generating portion 115 on the grasp portion 109 side and the coagulation treatment heat generating portion 114 on the grasp portion 108 side. Thus, the heat can be locally concentrated at the thermally coagulated portion of the site targeted for treatment such as blood vessel from the dissection treatment heat generating portion 117 on both sides. Therefore, the thermally coagulated portion of a site targeted for treatment such as coagulated blood vessel can be easily cut by heat of the dissection treatment heat generating portions 117 on both sides. The thermally coagulated patient's body tissue can be easily cut, and the treatment time can be reduced.

Figure 14C:
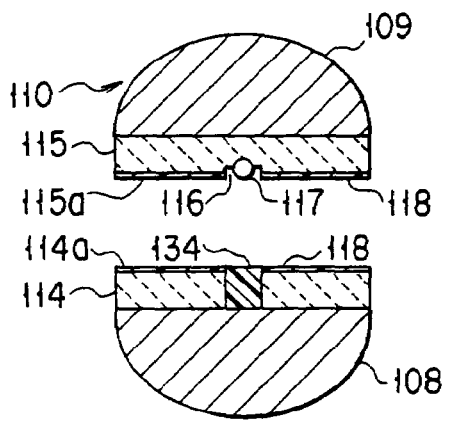
FIG. 14C is a longitudinal sectional view of essential portions showing a tenth embodiment of the present invention.

FIG. 14C shows a tenth embodiment of the present invention. In the present embodiment, a structure of the treatment portion 110 at the tip of the forceps 102 in the medical treatment instrument 101 of the seventh embodiment (refer to FIGS. 12 and 13) is modified as follows:

That is, in the seventh embodiment, there is shown a structure in which the recess portion 116 is formed at the substantial center site of the smooth surface 115a of the coagulation treatment heat generating portion 115 on the grasp portion 109 side; the dissection treatment heat generating portion 117 is arranged in this recess portion 116; and only the smooth surface 114a is provided on a surface opposite to the coagulation treatment heat generating portion 115 in the coagulation treatment heat generating portion 114 on the grasp portion 108 side. In the present embodiment, a porous heat insulation material 134 such as ceramic, for example, is arranged at a site opposite to the dissection treatment heat generating portion 117 at the grasp portion 109 side on the smooth surface 114a of the coagulation treatment heat generating portion 114 on the grasp portion 108 side.

In the forceps 102 of the present embodiment, the dissection treatment heat generating portion 117 is current-carried and heated. When the dissection treatment heat generating portion 117 is heated, the heat of the dissection treatment heat generating portion 117 can be prevented from escaping to the grasp portion 108 side by means of the heat insulation material 134 of the smooth surface 114a of the coagulation treatment heat generating portion 114 on the grasp portion 108 side. There is achieved an effect that the heat of the dissection treatment heat generating portion 117 can be intensively acted on a thermally coagulated portion of a site targeted for treatment such as blood vessel between the grasp portions 108 and 109 of the forceps 102, and thus, the thermally coagulated patient's body tissue can be easily cut.

Figure 14D:
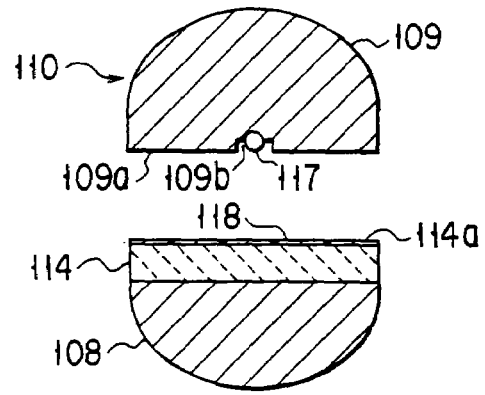
FIG. 14D is a longitudinal sectional view of essential portions showing an eleventh embodiment of the present invention.

FIG. 14D shows an eleventh embodiment of the present invention. In the present embodiment, a structure of the treatment portion 110 at the tip of the forceps 102 in the medical treatment instrument 101 of the seventh embodiment (refer to FIGS. 12 and 13) is modified as follows:

That is, in the present embodiment, the coagulation treatment heat generating portion 114 is provided at only one grasp portion 108 of a pair of the grasp portions 108 and 109; a recess portion 109b extended along the centerline direction of the grasp portion 109 is formed at the substantial center site on the contact surface 109a side with the patient's body tissue at the other grasp portion 109; and a dissection treatment heat generating portion 117 is arranged in this recess portion 109b.

In the present embodiment, an effect substantially similar to that in the seventh embodiment can be achieved. A Teflon coating layer may be provided on the contact surface 109a side with the patient's body tissue in the grasp portion 109. Further, the coagulation treatment heat generating portion is provided on the grasp portion 109 side only, whereby the dissection treatment heat generating portion 117 may be arranged.

FIGS. 15 to 17B show a twelfth embodiment of the present invention. In the present embodiment, a structure of the forceps 102 in the medical treatment instrument 101 of the seventh embodiment (refer to FIGS. 12 and 13) is modified as follows:

That is, in the forceps 102 of the present embodiment, the dissection treatment heat generating portion 117 on the grasp portion 109 side can be moved to a standby position shown in FIGS. 16A and 16B and a use position shown in FIGS. 17A and 17B.

Here, in the forceps 102 of the present embodiment, as shown in FIGS. 16A and 16B, a space 135 for movement of the dissection treatment heat generating portion 117 is formed on the grasp portion 109 side. Further, a gap 135a communicating with this movement space 135 is provided on a centerline at the coagulation treatment heat generating portion 115 on the grasp portion 109 side.

In addition, two front and rear triangular guide members 136 for guiding movement of the dissection treatment heat generating portion 117 are fixed, respectively, to the inner side of the movement space 135 on the grasp portion 109 side.

Further, the dissection treatment heat generating portion 117 is supported by means of a support member 137. Columnar smooth members 137a and 137b in contact with an inclined surface of the guide member 136 are fixed, respectively, to the front end and rear end of this support member 137. The dissection treatment heat generating portion 117 is movably maintained at the standby position shown in FIGS. 16A and 16B and the use position shown in FIGS. 17A and 17B while slide members 137a and 137b of the support member 137 move along the inclined surface of the guide member 136. At the standby position shown in FIGS. 16A and 16B, the dissection treatment heat generating portion 117 is maintained while it is apart from the coagulation treatment heat generating portion 114 of the grasp portion 108. At the use position shown in FIGS. 17A and 17B, the dissection treatment heat generating portion 117 is moved in a direction in which the section 117 abuts against the coagulation treatment heat generating portion 114 of the grasp portion 108.

In addition, an operating lever 138 retracting in the forward/backward direction is arranged between the support shaft 107 of the scissor constituent member 106 and the finger insert ring 112. This operating lever 138 is supported retractably from the forward position indicated by solid line in FIG. 15 to the backward position indicated by dotted line in the figure.

Further, the proximal end of an operating wire 139 for moving the dissection treatment heat generating portion 117 is fixed to this operating lever 138. The tip of this operating wire 139 is fixed to the rear end of the support member 137. When the operating lever 138 is maintained at the forward position indicated by solid line in FIG. 15, the dissection treatment heat generating portion 117 is maintained at the standby position shown in FIGS. 16A and 16B. When the operating lever 138 is operated to be moved to the backward position indicated by dotted line in FIG. 15, the dissection treatment heat generating portion 117 is moved to the use position shown in FIGS. 17A and 17B.

Now, an operation in the above structure will be described. When the forceps 102 of the present embodiment is used to perform treatment in a manner similar to that in the seventh embodiment, the following work are performed. First, the operating lever 138 of the scissor constituent member 106 is generally maintained at the forward position indicated by solid line in FIG. 15, the dissection treatment heat generating portion 117 is maintained at the standby position shown in FIGS. 16A and 16B. In this state, the forceps 102 is operated in accordance with the procedure similar to that in the seventh embodiment to release the site targeted for treatment such as blood vessel of the patent's body cavity, and is grasped between the grasp portions 108 and 109 to perform thermal coagulation.

Thereafter, the operating lever 138 is substantially moved from the forward position indicated by solid line in FIG. 15 to the backward position indicated by dotted line. At this time, an operating wire 139 is pulled backward together with backward operation of the operating lever 138, and the slide members 137a and 137b of the support member 137 is inclined backward along the inclined portion of the guide member 136. As a result, the dissection treatment heat generating portion 117 is moved to the use position shown in FIGS. 17A and 17B, and this dissection treatment heat generating portion 117 is abutted against the coagulation treatment heat generating portion 114.

In this state, when the dissection output operating portion 130 of the foot switch 132 is operated, the dissection treatment heat generating portion 117 is current-carried and heated. The thermally coagulated patient's body tissue is cut by the heat of the dissection treatment heat generating portion 117.

With the above structure, the following effect will be achieved. That is, in the forceps 102 of the present embodiment, the dissection treatment heat generating portion 117 is made movable to the standby position shown in FIGS. 16A and 16B and the use position shown in FIGS. 17A and 17B. In the case where the thermally coagulated patent's body tissue is cut, the dissection treatment heat generating portion 117 is moved to the use position shown in FIGS. 17A and 17B, and is abutted against the coagulation treatment heat generating portion 114 to come into close contact with the section 114. Thus, there is an effect that the thermally coagulated patent's body tissue can be thermally cut reliably, and the cut patent's body tissue is not left.

Figure 18:
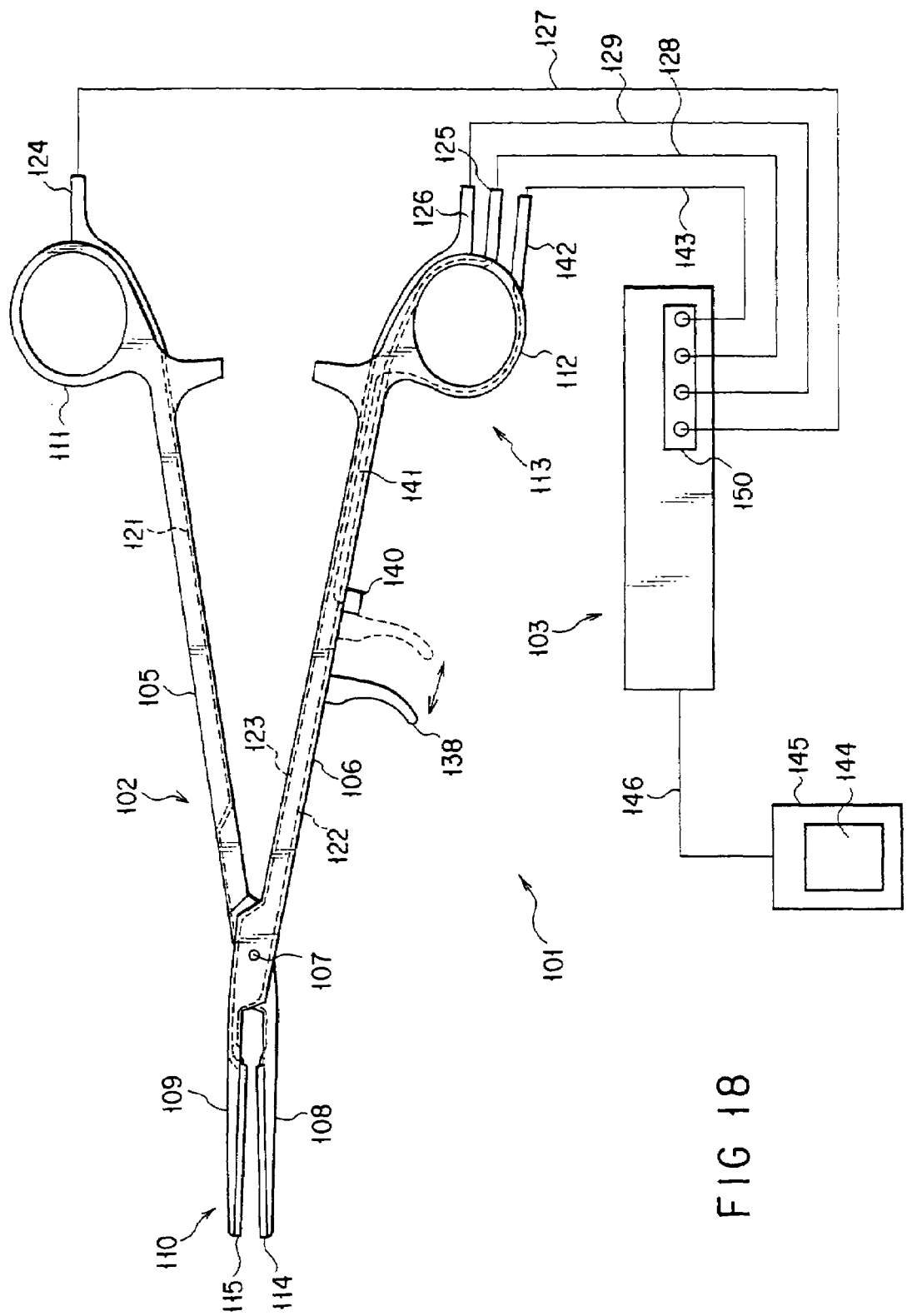
FIG. 18 is a schematic structural view showing the entire system of a medical treatment instrument according to a thirteenth embodiment of the present invention.

FIGS. 18 and 19 show a thirteenth embodiment of the present invention. In the present embodiment, a structure of the medical treatment instrument 101 of the twelfth embodiment (refer to FIGS. 15 to 17B) is modified as follows:

That is, in the forceps 102 of the present embodiment, switch means 140 for turning on/off the dissection treatment heat generating portion 117 is further arranged at the backward position of the operating lever 138 shown in the twelfth embodiment. At one end, a lead wire 141 is connected to this switch means 140. At the other end, this lead wire 141 is connected to the inner end of the cable connection portion 142 protruded on the peripheral surface of the finger insert ring 112 of the scissor constituent member 106. At one end, the connector cable 143 is detachably connected to the outer end of this cable connection portion 142. At the other end, this connector cable 143 is connected to the power supply unit 103.

In addition, a foot switch 145 comprising a coagulation output operating portion 144 is connected to the power supply unit 103 via a cable 146. Further, as shown in FIG. 19, an output circuit 147, a control circuit 148, and a detection circuit 149 are provided, respectively, inside the power supply unit 103. The output circuit 147, a detection circuit 149, a panel input/display portion 153 arranged on the operating panel of the power supply unit 103, and a foot switch 145 are connected, respectively, to the control circuit 148. The control circuit 148 is connected to the panel input/display portion 153 so that data is input and output bidirectionally. At the panel input/display portion 153, the output or temperature setting input or the temperature setting display or the like is performed.

Further, at an inner end side, the cable connector 150 provided at the power supply unit 103 is connected to the output circuit 147 via three output lines 151, and is connected to the detection circuit 149 via a detection line 152.

Now, an operation in the above structure will be described. When the forceps 102 of the present embodiment is used to perform treatment in a manner similar to that in the twelfth embodiment, the following work are performed.

First, as in the twelfth embodiment, the operating lever 138 of the scissor constituent member 106 is held at the forward position indicated by solid line in the FIG. 18, and the dissection treatment heat generating portion 117 is held at the standby position (shown in FIGS. 16A and 16B). In this state, the forceps 102 is operated in accordance with the procedure similar to that in the thirteenth embodiment, and the site targeted for treatment such as blood vessel that is the tissue in the patient's body cavity is released and grasped between the grasp portions 108 and 109. At this time, the coagulation output operating portion 144 of the foot switch 145 is operated, whereby the coagulation treatment heat generating portions 114 and 115 are current-carried and heated, and the site targeted for treatment such as blood vessel is thermally coagulated.

Thereafter, the operating lever 138 is subsequently operated to be moved from the forward position indicated by solid line in FIG. 18 to the backward position indicated by dotted line. At this time, the operating wire 139 is pulled back together with backward movement of the operating lever 138; the dissection treatment heat generating portion 117 is moved to the use position shown in FIGS. 17A and 17B; and this dissection treatment heat generating portion 117 is abutted against the coagulation treatment heat generating portion 114. Further, when the operating lever 138 is operated to be moved to the backward position, switch means 140 is actuated, and a signal is output from this switch means 140. At this time, the signal output from the switch means 140 is input to a detection circuit 149 of the power supply unit 103. Thus, the state in which operating lever 138 is moved to the backward position is detected by means of this detection circuit 149. When the state in which this operating lever 138 is moved to the backward position is detected, a control circuit 148 controls an output of the output circuit 147. Then, the dissection treatment heat generating portion 117 is current-carried and heated, and the thermally coagulated patent's body tissue is cut by the heat of the dissection treatment heat generating portion 117.

With the above structure, the following effect is obtained. That is, in the medical treatment instrument 101, when the operating lever 138 is operated to be moved to the backward position, the switch means 140 is actuated at the same time so as to switch an output of the power supply unit 103. Thus, there is no possibility that the coagulation treatment heat generating portions 114 and 115 and the dissection treatment heat generating portion 117 are mistakenly actuated due to mistaken stepping of the foot switch 145, and there is an effect that coagulating and cutting operations can be performed safely.

FIGS. 20A and 20B show a fourteenth embodiment of the present invention. In the present embodiment, the present invention is applied to a surgical treatment instrument 154 used for surgical operation under endoscope as a medical treatment instrument. FIG. 20A shows a schematic structure of the entire surgical treatment instrument 154.

The treatment instrument 154 of the present embodiment is provided with an elongated insert portion 155 to be inserted into the patent's body through a trocar (not shown) and a frontal operating portion 156 linked with the proximal end of this insert portion 155.

The insert portion 155 is provided with a tubular insert tube body 157. A driving shaft 158 relatively moved in axial direction of the insert portion 155 is inserted into this insert tube body 157. Further, a treatment portion 159 is arranged at the tip of the insert portion 155. This treatment portion 159 is provided with a pair of grasp members 160a and 160b capable to be opened and closed. A pair of grasp members 160a and 160b is coupled with the tip of the driving shaft 158 via a driving mechanism such as cam mechanism (not shown). An interval between the grasp members 160a and 160b is driven to be opened and closed via the driving mechanism together with retracting movement of the driving shaft 158.

The grasp members 160a and 160b of the present embodiment are structured in a manner substantially similar to that of each of the grasp portions 108 and 109 in the forceps 102 of the present embodiment (refer to FIGS. 15 to 17B).

That is, as in each of the grasp portions 108 and 109 of the twelfth embodiment, the grasp members 160a and 160b of the present embodiment are internally provided with the coagulation treatment heat generating portion 114, coagulation treatment heat generating portion 115, dissection treatment heat generating portion 117, support member 137, slide members 137a and 137b, guide member 136, and operating wire 139 shown in FIGS. 16A, 16B, 17A and 17B.

In addition, the frontal operating portion 156 is provided with an operating portion main body 162 for rotatably holding the proximal end of the insert portion 155. A fixing handle 163 is formed integrally with this operating portion main body 162. A rotating operation knob 164 for rotationally operating the proximal end of the insert portion 155 is arranged at the tip of the operating portion main body 162.

Further, a link portion of a movable handle 165 is rotatably linked with the fixing handle 163 via a support shaft 166. The proximal end of the driving shaft 158 is linked with this movable handle 165.

Further, a first finger insert ring 167a into which the operator's finger can be inserted is formed at the end of the fixing handle 163. Still further, a second finger insert ring 167b into which the operator's finger can be inserted is formed similarly at the end of the movable handle 165. The driving shaft 158 is driven retractably along axial direction together with opening/closing (rotating) operation of the movable handle 165 relative to the fixing handle 163, and an interval between the grasp members 160a and 160b of the treatment portion 159 is driven to be opened and closed.

Further, in the fixing handle 163 of the present embodiment, there is arranged the operating lever 161 in which the dissection treatment heat generating portion 117 is operated to be moved to be the standby position shown in FIGS. 16A and 16B and to the use position shown in FIGS. 17A and 17B. This operating lever 161 is supported retractably from the forward position indicated by solid line in FIG. 20A to the backward position indicated by dotted line in the figure. The dissection treatment heat generating portion 117 is moved to a direction in which the section 117 is close to/distant from the coagulation treatment heat generating portion 114 together with operation of this lever 161.

Now, an operation in the above structure will be described. When the surgical treatment instrument 154 of the present embodiment is used, the operator's fingers are inserted into a ring 167a of the fixing handle 163 and into a ring 167b of the movable handle 165. In this state, the movable handle 165 is rotated relative to the fixing handle 163. At this time, the driving shaft 158 is moved in axial direction relative to the insert portion 155 together with rotating operation of the movable handle 163, and an interval between the grasp members 160a and 160b of the treatment portion 159 is driven to be opened and closed at the tip of the insert portion 155 via the driving mechanism.

Further, the lever 161 is operated by fingers other than those inserted into the rings 167a and 167b, whereby the operating wire 139 of the dissection treatment heat generating portion 117 is moved in axial direction relative to the insert portion 155, and is operated to be moved to a direction in which the wire is close to/distant from the tissue grasp surface of the coagulation treatment heat generating portion 114 in which the grasp portion 160a is provided with the dissection treatment heat generating portion 117.

As in the twelfth embodiment, when the treatment instrument 154 of the present embodiment is used to treat a site targeted for treatment such as blood vessel in the patent's body tissue, a site targeted for treatment such as blood vessel that is a tissue in the patient's body cavity is released through operation similar to that in the twelfth embodiment, and is grasped between the grasp members 160a and 160b to perform thermal coagulation.

When the lever 161 is subsequently operated to be moved from the solid line position to the dotted line position in FIG. 20A, the wire 139 is pulled backward, and slide members 137a and 137b fixed to the support member 137 are moved to be inclined backward along the inclined portion of the guide member 136. As a result, as shown in FIGS. 17A and 17B, the dissection treatment heat generating portion 117 is abutted against the coagulation treatment heat generating portion 114. In this state, the dissection output operating portion 130 of the foot switch 132 is operated, whereby the dissection treatment heat generating portion 117 is current-carried and heated, and the thermally coagulated tissue is cut.

With the above structure, the following effect is obtained. That is, in the treatment instrument 154 of the present embodiment, the dissection treatment heat generating portion 117 is protruded and recessed on the centerline of the coagulation treatment heat generating portion 114. Thus, the thermally coagulated patients body tissue can be thermally cut reliably, the cut patient's body tissue is not left, and the treatment time can be reduced.

In addition, FIGS. 21, 22A and 22B show a fifteenth embodiment of the present invention. FIG. 21 shows a structure of a forceps 172 that is a medical treatment instrument 171 of the present embodiment.

A main body 173 of the forceps 172 is provided with two scissor constituent members 174 and 175. These scissor constituent members 174 and 175 are placed in a state in which the intermediate portions substantially cross with each other. Further, a support shaft 176 for rotatably linking the scissor constituent members 174 and 175 with each other is arranged at the cross section of the scissor constituent members 174 and 175.

In addition, a treatment portion 179 comprising a pair of the grasp portions 177 and 178 capable of being opened and closed, which grasps the patients body tissue, is arranged at the tip of the forceps main body 173. This treatment portion 179 is molded in the substantially same shape as that in the release forceps.

Further, substantially elliptical finger insert rings 180 and 181 are formed at the proximal end of each of the scissor constituent members 174 and 175. A frontal operating portion 182 for opening/closing a pair of grasp portions 177 and 178 is formed by the portions of these finger insert rings 180 and 181.

A substantially arc-shaped, gently curved curve portion 183 is formed at a treatment portion 179 of the forceps main body 173, as shown in FIG. 22A. Furthermore, at each of the grasp portions 177 and 178 of the forceps main body 173, as shown in FIG. 22B, coagulation treatment heat generating portions 184 and 185 having substantially planar, wide rectangular cross section are arranged, respectively, on the contact surface side with the patient's body tissue. These coagulation treatment heat generating portions 184 and 175 such as ceramic heater or PTC heater are current-carried to generate heat, and is formed by a heating element.

Teflon coating layers 186 and 187 for preventing scorch of the patient's body tissue are formed, respectively, on the outer surface of the coagulation treatment heat generating portions 184 and 185 (the contact surface with the patient's body).

Further, at the widthwise center portion of each of the grasp portions 177 and 178 of the treatment portion 179, as shown in FIG. 22A, a gap 188 gently curved in the arc shape is provided along the curve shape of the curve portion 183. This gap 188 is formed as a route-to the coagulation treatment heat generating portions 184 and 185 in the same width. The tip of this gas 188 is structured of having opened at the tip of each of the grasp portions 177 and 178.

As shown in FIG. 21, a lead wire 189 is arranged at one scissor constituent member 174, and a lead wire 190 is arranged at the other scissor constituent member 175, respectively. At the tip, the lead wire 189 is connected to the coagulation treatment heat generating portion 184. At the tip, the lead wire 190 is connected to the coagulation treatment heat generating portion 185.

Further, a cable connection portion 191 is protruded on the peripheral surface of the finger insert ring 180 on the scissor constituent member 174 side. Furthermore, a cable connection portion 192 is protruded on the peripheral surface of the finger insert ring 181 on the scissor constituent member 175 side. The proximal end of the lead wire 189 is connected to the cable connection portion 191 on the scissor constituent member 174 side, and the lead wire 190 is connected to the cable connection portion 192 on the scissor constituent member 175 side.

Now, an operation of the medical treatment instrument 171 with the above structure according to the present embodiment will be described. First, the treatment portion 179 is inserted into the patient's body tissue including a site targeted for treatment such as blood vessel (not shown) while it is closed at the tip of the forceps 172. Thereafter, a pair of grasp portions 177 and 178 are opened, whereby the site targeted for treatment such as blood vessel is released from the patent's body tissue, and is exposed.

Subsequently, the released blood vessel or the like is grasped between the grasp portions 177 and 178 while it is compressed with a proper pressure suitable to coagulating treatment. In this state, when a power supply unit (not shown) is output, the coagulation treatment heat generating portions 184 and 185 of the grasp portions 177 and 178 are current-carried and heated. At this time, a site targeted for treatment such as blood vessel between the grasp portions 177 and 178 is well thermally coagulated due to the heat of the coagulation treatment heat generating portion 184 and 185.

Thereafter, in this state, a surgical knife (not shown) or a high-frequency knife is inserted into the gap 188 of each of the grasp portions 177 and 178 of the treatment portion 179, and the site targeted for treatment such as blood vessel is cut.

With the above structure, the following effect is obtained. In the medical treatment instrument 101 of the present embodiment, a wide coagulation treatment heat generating portions 184 and 185 are arranged at the grasp portions 177 and 178 of the forceps main body 173. Thus, the site targeted for treatment such as blood vessel grasped between the grasp portions 177 and 178 of the forceps main body 173 can be thermally coagulated reliably due to the heat of these coagulation treatment heat generating portions 184 and 185 while it is compressed with a proper pressure.

Further, in the present embodiment, the gap 188 is provided at the widthwise center portion of each of the grasp portions 177 and 178 of the treatment portion 179. After the site targeted for treatment such as blood vessel has been thermally coagulated, another cutting means such as surgical knife or high-frequency knife is inserted into the gap 188 between the grasp portions 177 and 178 in the treatment portion 179, whereby the tissue of the site targeted for treatment such as coagulated blood vessel can be cut. Therefore, in particular, the site can be treated simply and speedily by abdominal cutting surgery. In addition, the structure is simplified and advantageous in cost efficiency in comparison with the structure in which the coagulating function and cutting function of the tissue of the site targeted for treatment are performed by a single instrument.

FIGS. 23A and 23B show a sixteenth embodiment of the present invention. In the present embodiment, a structure of the treatment portion 179 at the tip of the forceps 172 in the medical treatment instrument 171 according to the fifteenth embodiment (refer to FIGS. 21, 22A and 22B) is modified as follows:

That is, in the present embodiment, the gap 188 is not provided on the grasp portion 177 side of one scissor constituent member 174, and the gap 188 is provided on the grasp portion 178 side only of the other scissor constituent member 175.

Now, an operation in the above embodiment will be described. When the forceps 172 of the present embodiment is used to perform treatment in a manner similar to the fifteenth embodiment, the following work are performed. First, the forceps 172 is operated in accordance with the procedure similar to that in the fifteenth embodiment, whereby the site targeted for treatment such as blood vessel that is a tissue in the patent's body cavity is released, and grasped between the grasp portions 177 and 178 to perform thermal coagulation.

Then, in this state, the surgical knife (not shown) or the high-frequency knife is inserted into the gap 188 of one grasp portion 178 of the treatment portion 179, and the site targeted for treatment such as coagulated blood vessel is cut.

With the above structure, the following effect is obtained. That is, in the present embodiment, when a surgical knife or a high-frequency knife is inserted into the gap 188, the tip of the knife is pressed to be abutted against the surface of the coagulation treatment heat generating portion 184 of the grasp portion 177 of the treatment portion 179, and the subsequent inserting operation is stopped. Therefore, the tip of the knife is prevented from penetrating the outside of the gap 188, and there is no possibility that a portion other than the site targeted for treatment is cut, which is safe.

Figure 24:
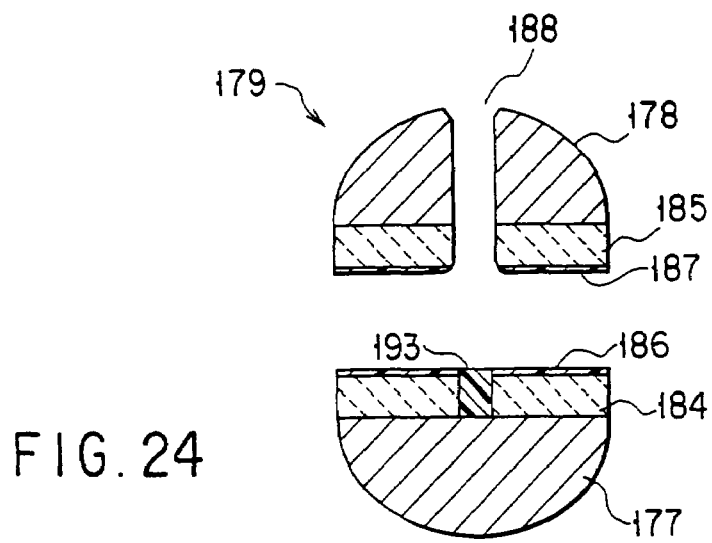
FIG. 24 is a cross sectional view of essential portions showing a medical treatment instrument according to a seventh embodiment of the present invention.

FIG. 24 shows a seventeenth embodiment of the present invention. In the present embodiment, a structure of the treatment portion 179 at the tip of the forceps 172 in the medical treatment instrument 171 according to the fifteenth embodiment is modified as follows:

That is, in the present embodiment, as in the sixteenth embodiment (refer to FIGS. 23A and 23B), the gap 188 is not provided at the grasp portion 177 side of one scissor constituent member 174, and the gap 188 is provided on the grasp portion 178 side only of the other scissor constituent member 175. Further, in the present embodiment, in addition to these scissor constituent members, on the grasp portion 177 side of the scissor constituent member 174, a receiving member 193 consisting of an ultra hard metal such as tungsten is arranged instead at a site corresponding to the gap 188 of the grasp portion 178 side.

Now, an operation in the above structure will be described. When the forceps 172 of the present embodiment is used to perform treatment in a manner similar to that in the fifteenth embodiment, the following work are performed. First, the forceps 172 is operated in accordance with the procedure similar to that in the fifteenth embodiment, whereby the site targeted for treatment such as blood vessel that is a tissue in the patent's body cavity is released, and is grasped between the grasp portions 177 and 178 to perform thermal coagulation.

Then, in this state, the surgical knife (not shown) or the high-frequency knife is inserted into the gap 188 of one grasp portion 178 of the treatment portion 179, and the site targeted for treatment such as coagulated blood vessel is cut.

With the above structure, the following effect is obtained. That is, in the present embodiment, when the surgical knife or the high-frequency knife is inserted into the gap 188, the tip of the knife is pressed to be abutted against the surface of the receiving member 193 of the grasp portion 177, and the subsequent inserting operation is stopped. Therefore, the tip of the knife is prevented from penetrating the outside of the gap 188, and there is no possibility that a portion other than the site targeted for treatment is cut, which is safe.

Further, in the present embodiment, the receiving member 193 is made of an ultra hard metal. When the tip of the knife is pressed to be abutted against the receiving member 193, the degradation due to damage caused on the surface can be prevented.

Figure 25:
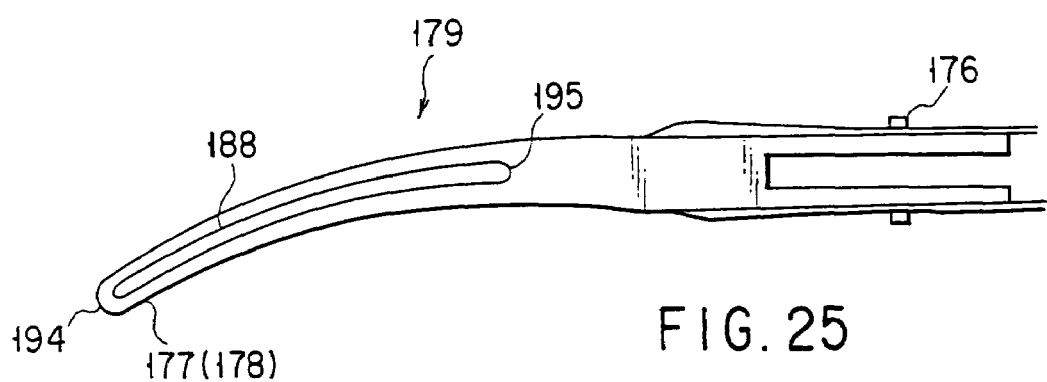
FIG. 25 is a plan view of essential portions showing the curve portion of a grasp portion of a medical treatment instrument according to an eighteenth embodiment of the present invention.

FIG. 25 shows an eighteenth embodiment of the present invention. In the present embodiment, a structure of the treatment portion 179 at the tip of the forceps 172 in the medical treatment instrument 171 according to the fifteenth embodiment (refer to FIGS. 21, 22A and 22B) is modified as follows:

That is, in the present embodiment, a closing portion 194 for closing the tip of the gap 188 of each of the grasp portions 177 and 178 of the treatment portion 179 is provided so that the tip of the gap 188 of each of the grasp portions 177 and 178 is not opened.

With the above structure, when the surgical knife or the high-frequency knife is inserted into the gap 188 to cut the site targeted for treatment, the knife movement range is restricted between the closing portion 194 at the tip of the gap 188 and a terminal end 195 of this gap 188. Therefore, in particular, when a parenchymal organ such as liver is coagulated and cut, there is no possibility that a site not coagulated other than a site targeted for dissection is cut and blooded, and there is an effect that the site can be treated safely.

Figure 26:
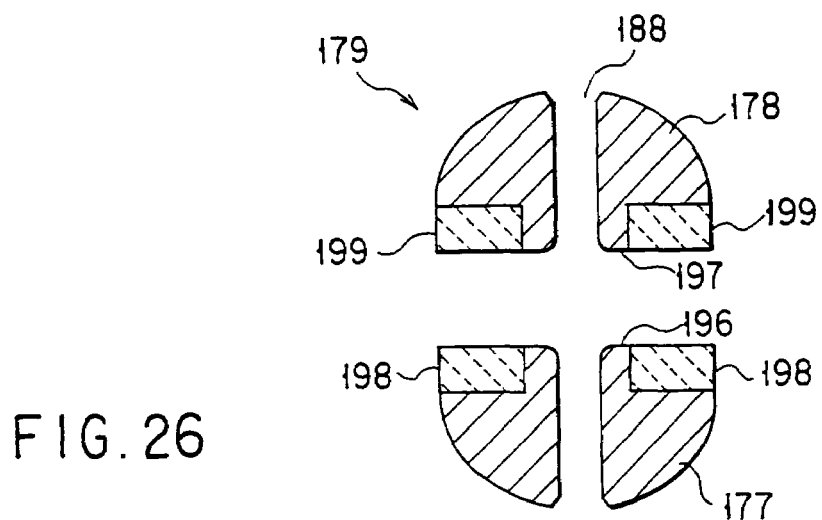
FIG. 26 is a cross sectional view of essential portions showing the medical treatment instrument according to a nineteenth embodiment of the present invention.

FIG. 26 shows a nineteenth embodiment of the present invention. In the present embodiment, the treatment portion 179 at the tip of the forceps 172 in the medical treatment instrument 171 according to the fifteenth embodiment (refer to FIGS. 21, 22A and 22B) is changed for high-frequency treatment.

That is, in the present embodiment, the forceps main body 173 in the forceps 172 is entirely made of an insulation material. Further, at the grasp portions 177 and 178 of the forceps main body 173, insulation portions 196 and 197 covered with an insulation material are structured of being formed, respectively, on the inner surface side of the gap 188.

In addition, at the grasp portions 177 and 178, a pair of sectional, rectangular electrodes 198 and 199 are arranged, respectively, at their positions opposite to each other on the outside of the insulation portions 196 and 197 on both sides of the gap 188. Each of the electrodes 198 and 199 is connected to a high-frequency power supply unit (not shown) via a lead wire.

Now, an operation in the above structure will be described. When the forceps 172 of the present embodiment is used to perform treatment in a manner similar to that in the fifteenth embodiment, the site targeted for treatment such as vessel blood that is a tissue in the patent's body cavity is released. After the site has been grasped between the grasp portions 177 and 178, an interval between electrodes 198 and 199 of the grasp portions 177 and 178 is current-carried at a high frequency, and coagulation is performed.

Then, in this state, the surgical knife (not shown) or the high-frequency knife is inserted into the gap 188 of one grasp portion 178 of the treatment portion 179, and the site targeted for treatment such as coagulated blood vessel is cut.

With the above structure, the following effect is obtained. That is, in the forceps 172 of the present embodiment, a site targeted for treatment is coagulated by supplying the high-frequency bipolar power. At the same time, the high-frequency power supply unit is switched to monopolar, whereby the coagulated site can be cut by the high-frequency knife. Therefore, coagulation and cutting can be performed by a single power supply unit, making it advantageous in cost efficiency.

Figure 27:
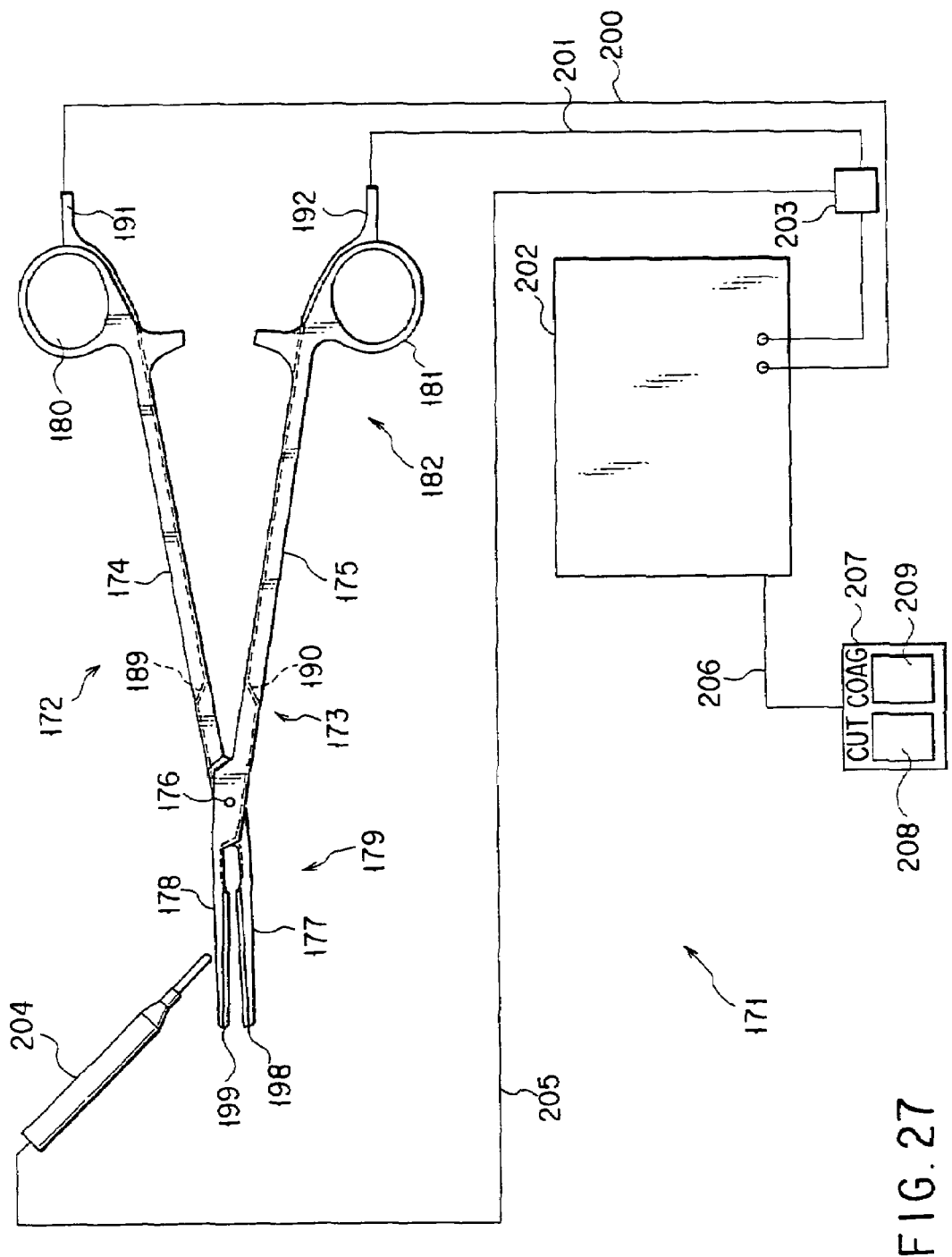
FIG. 27 is a schematic structural view showing the entire system of a medical treatment instrument according to a twentieth embodiment of the present invention.

FIG. 27 shows a twentieth embodiment of the present invention. In the present embodiment, a structure of the medical treatment instrument 171 according to the fifteenth embodiment (refer to FIGS. 21, 22A and 22B) is modified as follows:

That is, in the present embodiment, as in the nineteenth embodiment (refer to FIG. 26), the structure is changed such that the treatment portion 179 at the tip of the forceps 172 is provided with the high-frequency treatment electrodes 198 and 199, and the patient's body tissue is coagulated by supplying high-frequency power. Here, the electrode 198 on one grasp portion 177 side is connected to the inner end of the cable connection portion 191 of the finger insert ring 180 on the scissor constituent member 174 side via the lead wire 189. Further, the electrode 199 on the other grasp portion 178 side is connected to the inner end of the cable connection portion 192 of the finger insert ring 181 on the scissor constituent member 175 side via the lead wire 190.

At one end, a connector cable 200 is detachably connected to the outer end of the cable connection portion 191. At one end, the connector cable 201 is detachably connected to the outer end of the cable connection portion 192. At the other ends, these connector cables 200 and 201 are connected to the high-frequency power supply unit 202.

A switch unit 203 is intervened intermediately of the connector cable 201 of the high-frequency power supply unit 202. To this switch unit 203, a high-frequency knife 204 is connected via a cable 205. The high-frequency knife 204 is connected to the high-frequency power supply unit 202 via this switch unit 203. A foot switch 207 is connected to the high-frequency power supply unit 202 via a cable 206. This foot switch 207 is provided with a dissection output operating portion 208 and the coagulation output operating portion 209.

Now, an operation in the above structure will be described. When the forceps 172 of the present embodiment is used to perform treatment in a manner similar to that in the nineteenth embodiment, the following work are performed. First, the forceps 172 is operated in accordance with the procedure similar to that in the fifteenth embodiment, whereby a site targeted for treatment such as blood vessel that is a tissue in the patient's body cavity is released, and is grasped between the grasp portions 177 and 178. Then, a coagulation output operating portion 209 in the foot switch 207 is operated. In this manner, the site targeted for treatment such as blood vessel between the grasp portions 177 and 178 is coagulated by supplying high-frequency power between the electrodes 198 and 199.

Then, in this state, the high-frequency knife 204 is inserted into the gap 188 between the grasp portions 177 and 178 of the treatment portion 179, and a power supply route of the switch unit 203 is changed. Then, a dissection output operating portion 208 in the foot switch 207 is operated, whereby dissection power is supplied from the high-frequency knife 204 to the electrode 199 in the forceps 172, and the site targeted for treatment is cut.

With the above structure, the following effect is obtained. That is, when a site targeted for treatment such as blood vessel is cut in the forceps 172 of the present embodiment, the site targeted for treatment can be cut by only bipolar power without changing it to monopolar power, enabling safe treatment.

Figure 28:
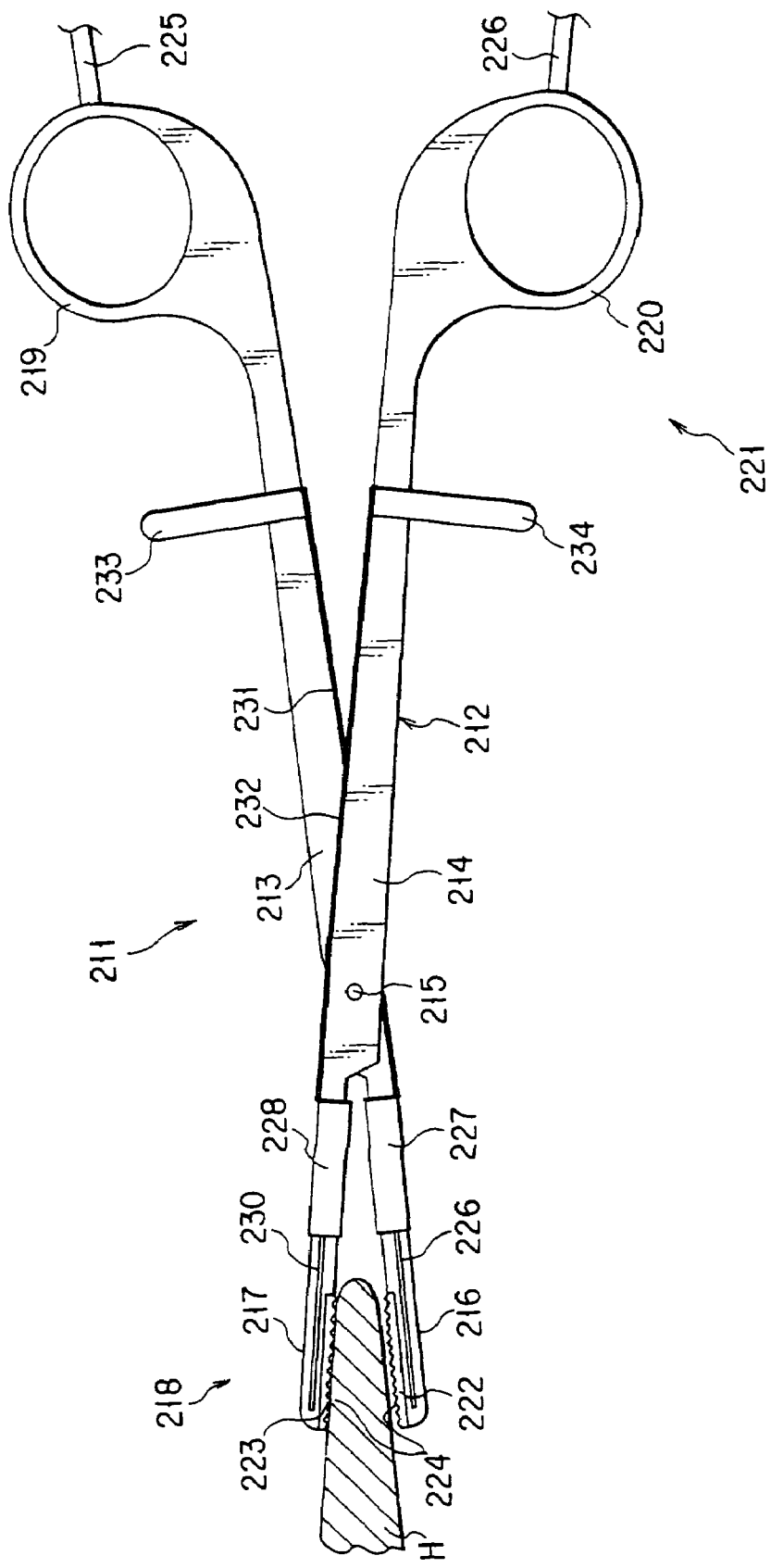
FIG. 28 is an entire plan view showing the medical treatment instrument according to a twenty-first embodiment of the present invention.
Figure 29:
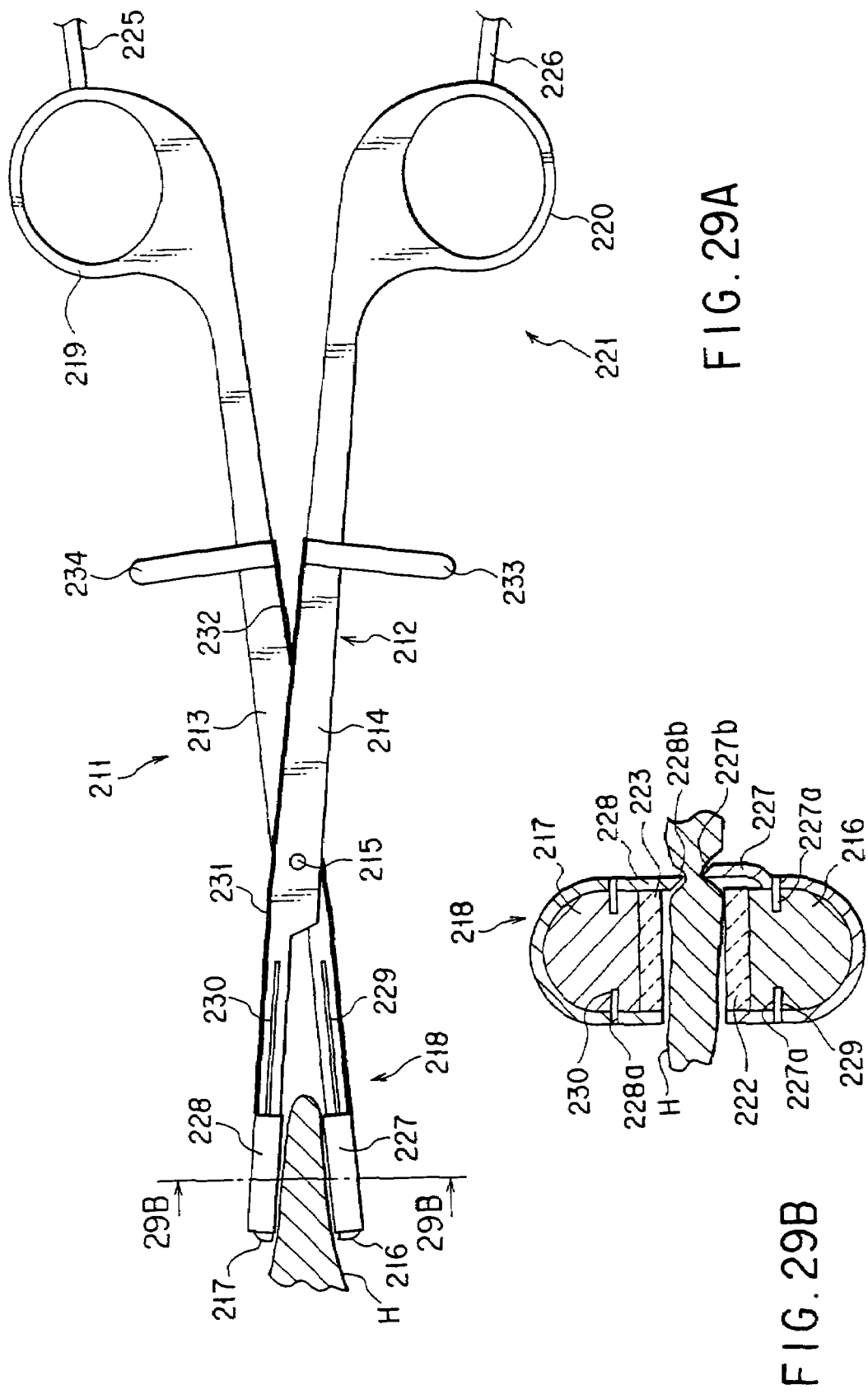
FIG. 29A is a plan view showing a state in which a scissor blade of the medical treatment instrument according to the twenty-first embodiment is slid to the tip side.
FIG. 29B is a cross sectional view taken along the line 29B-29B of FIG. 29A.

FIGS. 28, 29A and 29B show a twenty-first embodiment of the present invention. FIG. 28 shows a structure of a dissection cutting treatment instrument 211 that is a medical treatment instrument of the present embodiment.

Here, a main body 212 of the coagulation cutting treatment instrument 211 is provided with two scissor constituent members 213 and 214. These scissor constituent members 213 and 214 are placed so that the intermediate portions substantially cross with each other. Further, a support shaft 215 for rotatably linking these scissor constituent members 213 and 214 with each other is arranged at the cross section of these scissor constituent members 213 and 214.

A treatment portion 218 comprising a pair of jaws 216 and 217 capable of being opened and closed, which grasps the patient's body tissue, is arranged at the tip of the treatment instrument main body 212. Further, the substantially elliptical finger insert rings 219 and 220 are formed at the proximal ends of the scissor constituent members 213 and 214. A frontal operating portion 221 for opening/closing a pair of jaws 216 and 217 is formed by the portions of these finger insert rings 219 and 220.

Heaters 222 and 223 are provided for coagulating the patient's body tissue H at the jaws 216 and 217. Each of the heaters 222 and 223 is provided with a tooth portion 224 for preventing the patient's body tissue from slipping off. The heaters 222 and 223 may be any of publicly known heater means such as ceramic heaters, PTC heaters, semiconductor heaters, or electric heat wires.

Cable connection portions 225 and 226 are protruded, respectively, at the finger insert rings 219 and 220 of the operating portion 221. A heater 222 is connected to the inner end of one cable connection portion 225 via a lead wire. A heater 223 is connected to the inner end of the other cable connection portion 226 via the lead wire. Further, connector cables for supplying power to the heaters 222 and 223 are connected to the outer ends of cable connection portions 225 and 226.

The jaws 216 and 217 are provided with cutting treatment scissor blades 227 and 228 for cutting the patient's body tissue H, respectively. These scissor blades 227 and 228 are formed in sectional substantial U shape as shown in FIG. 29B. These scissor blades 227 and 228 are mounted on the jaws 216 and 217 while they surround the outer peripheries of the jaws 216 and 217.

In addition, slide grooves 229 and 230 for movably guiding the scissor blades 227 and 228 in the forward/backward direction are formed on both side surfaces of the jaws 216 and 217. Further, guide protrusions 227a and 228a to be inserted into these slide grooves 229 and 230 are protruded at the scissor blades 227 and 228. The scissor blades 227 and 228 are slidably supported forward and backward along the slide grooves 229 and 230. Sharp blade portions 227b and 228b are formed on the side portions of the U-shaped sections of the scissor blades 227 and 228, respectively.

At tips, operating bars 231 and 232 are linked with the scissor blades 227 and 228. The proximal ends of these operating bars 231 and 232 are linked with levers 233 and 234 disposed in the vicinity of the operating portion 221. The scissor blades 227 and 228 are operated to be slid forward and backward along the slide grooves 229 and 230 of the jaws 216 and 217 via the operating bars 231 and 232 together with forward/backward slide operations of the levers 233 and 234.

Now, an operation in the above structure will be described. When the coagulating/cutting treatment instrument 211 of the present embodiment is used, the scissor blades 227 and 228 are held at a standby position at which they are retracted to the frontal side of the treatment instrument main body 212 as shown in FIG. 28 at a usual time other than dissection of the patient's body tissue H. In this state, after the jaws 216 and 217 have been opened by the operating portion 221, the jaws 216 and 217 are closed as shown in FIG. 28, and the patient's body tissue H is grasped between the upper and lower heaters 222 and 223. At this time, the scissor blades 227 and 228 are held while they are not in contact with the patient's body tissue H. In this state, the upper and lower heaters 222 and 223 are current-carried and heated, and the patient's body tissue H between the upper and lower heaters 222 and 223 is coagulated.

Next, after the jaws 216 and 217 have been opened, the levers 233 and 234 of the scissor blades 227 and 228 are operated to be pushed out toward the tip side, and the scissor blades 227 and 228 are moved to the tip positions of the jaws 216 and 217 as shown in FIG. 29A.

In that state, the jaws 216 and 217 are closed, whereby the patient's body tissue H is sheared and cut between the upper and lower scissor blades 227 and 228 as if it were done by a pair of scissors.

With the above structure, the following effect is obtained. That is, in the present embodiment, the heaters 222 and 223 for coagulating the patient's body tissue H is provided at the jaws 216 and 217 of the treatment portion 218 of the treatment instrument main body 212, and the cutting treatment scissor blades 227 and 228 for cutting the patient's body tissue H are provided movably in the forward/backward direction of the jaws 216 and 217. The scissor blades 227 and 228 are held at a standby position at which these blades are retracted to the frontal side of the treatment instrument main body 212 as shown in FIG. 28. In this state, coagulating treatment of the patient's body tissue H is performed, and the scissor blades 227 and 228 are moved to the tip positions of the jaws 216 and 217 as shown in FIG. 29A. In this state, cutting treatment of the patient's body tissue H can be performed. In the present embodiment, coagulating treatment and cutting treatment can be performed at the tips of the jaws 216 and 217 of the treatment portion 218 of the treatment instrument main body 212, and thus, there is an effect that delicate treatment can be performed.

Further, when the patient's body tissue H is cut to be treated, the patient's body tissue H can be cut to be treated by opening/closing the scissor constituent members 213 and 214 like a pair of scissors, thus improving operability and enabling fine cutting treatment.

Figure 30:
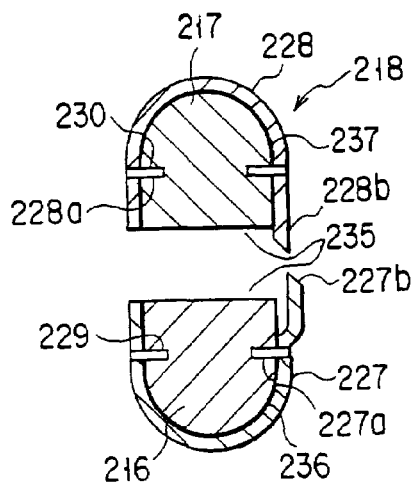
FIG. 30 is a cross sectional view of essential portions showing a medical treatment instrument according to a twenty-second embodiment of the present invention.

FIG. 30 shows a twenty-second embodiment of the present invention. In the present embodiment, a structure of the treatment portion 218 at the tip of the treatment instrument main body 212 in the coagulating/cutting treatment instrument 211 according to the twenty-first embodiment (refer to FIGS. 28, 29A, and 29B) is modified as follows:

That is, in the present embodiment, the heaters 222 and 223 of the twenty-first embodiment are eliminated, and a bipolar electrode 235 is structured by the jaws 216 and 217 themselves. In addition, insulation layers 236 and 237 are structured to be provided between the jaws 216 and 217 and the knife blades 227 and 228 so that a current is not supplied to the knife blades 227 and 228 during coagulation.

In the present embodiment, coagulating treatment is performed at the bipolar electrode 235 at the tip of each of the jaws 216 and 217 of the treatment portion 218 of the treatment instrument main body 212, and cutting treatment can be performed by the knife blades 227 and 228 of the jaws 216 and 217 on both sides. In the present embodiment, as in the twenty-first embodiment, coagulating treatment and cutting treatment can be performed at the tip of each of the jaws 216 and 217 of the treatment portion 218 of the treatment instrument main body 212, and thus, there is an effect that delicate treatment can be performed.

Figure 31:
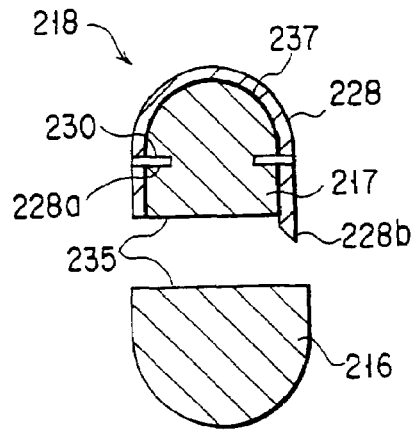
FIG. 31 is a cross sectional view of essential portions showing a medical treatment instrument according to a twenty-third embodiment of the present invention.

FIG. 31 shows a twenty-third embodiment of the present invention. In the present embodiment, a knife blade 228 is provided at only a single-sided jaw 217 of the treatment portion 218 at the tip of the treatment instrument main body 212 in the coagulating/cutting treatment instrument 211 according to the twenty-second embodiment (refer to FIG. 30).

In the present embodiment, coagulating treatment is performed at the bipolar electrode 235 at the tip of each of the jaws 216 and 217 of the treatment portion 218 of the treatment instrument main body 212, and cutting treatment can be performed by the knife blade 228 of the single-sided jaw 217. In the present embodiment, as in the coagulating/cutting treatment instrument 211 according to the twenty-second embodiment, there is an effect that delicate treatment can be performed.

A cutting current is supplied to the knife blade 228 of the present embodiment, and the knife blade 228 is current-carried and heated, whereby cutting treatment of the patient's body tissue H may be performed.

Figure 32:
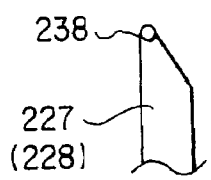
FIG. 32 is a structural side view of essential portions showing a coagulating/dissection treatment instrument according to a twenty-fourth embodiment of the present invention.

FIG. 32 shows a twenty-fourth embodiment of the present invention. In the present embodiment, a structure of the treatment portion 218 at the tip of the treatment instrument main body 212 in the coagulating/cutting treatment instrument 211 according to the twenty-first embodiment (refer to FIGS. 28, 29A and 29B) is modified as follows:

That is, in the present embodiment, a dissection treatment heat generating portion 238 such as nichrome wire is structured to be provided at the tip of each of the knife blades 227 and 228 of the jaws 216 and 217 on both sides of the treatment portion 218 so that cutting treatment is performed by this dissection treatment heat generating portion 238.

In the present embodiment, coagulating treatment is performed at the bipolar electrode 235 at the tip of each of the jaws 216 and 217 of the treatment portion 218 of the treatment instrument main body 212, and cutting treatment can be performed by the dissection treatment heat generating portion 238 of each of the jaws 216 and 217 on both sides. In the present embodiment, as in the coagulating/cutting treatment instrument 211 according to the twenty-first embodiment, coagulating treatment and cutting treatment can be performed at the tip of each of the jaws 216 and 217 of the treatment portion 218 of the treatment instrument main body 212, and thus, there is an effect that delicate treatment can be performed.

Figure 33:
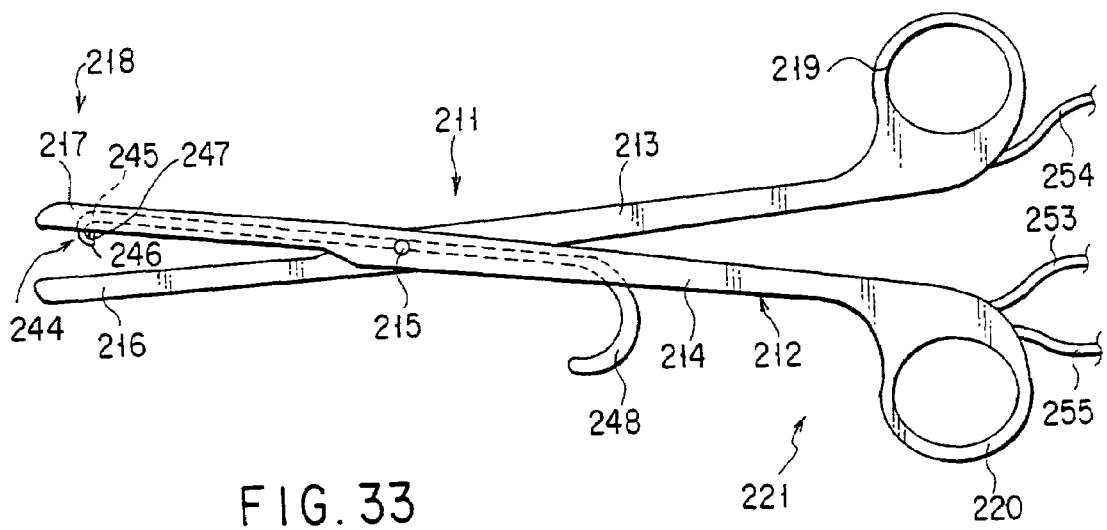
FIG. 33 is an entire plan view showing a coagulating/dissection treatment instrument according to a twenty-fifth embodiment of the present invention.
Figure 34A:
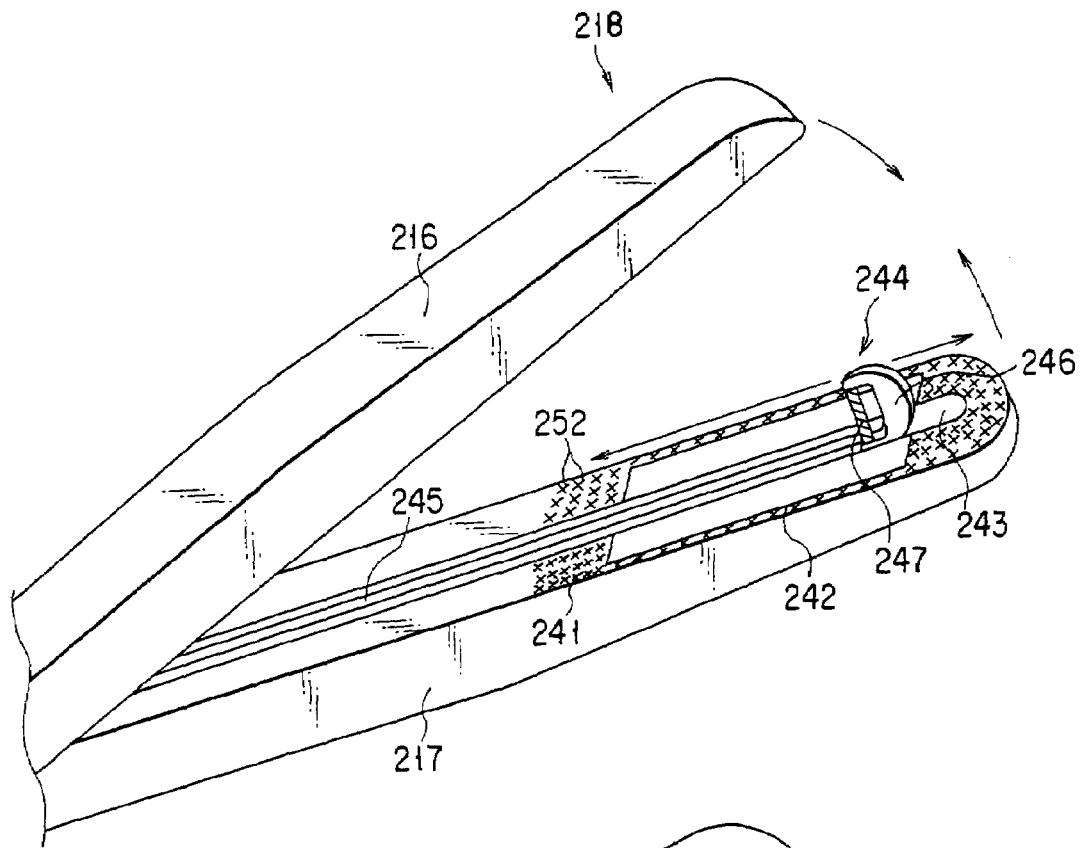
FIG. 34A is a perspective view showing a mount state of heating elements on a grasp surface of one jaw in the coagulating/dissection treatment instrument according to the twenty-fifth embodiment.
Figure 34B:
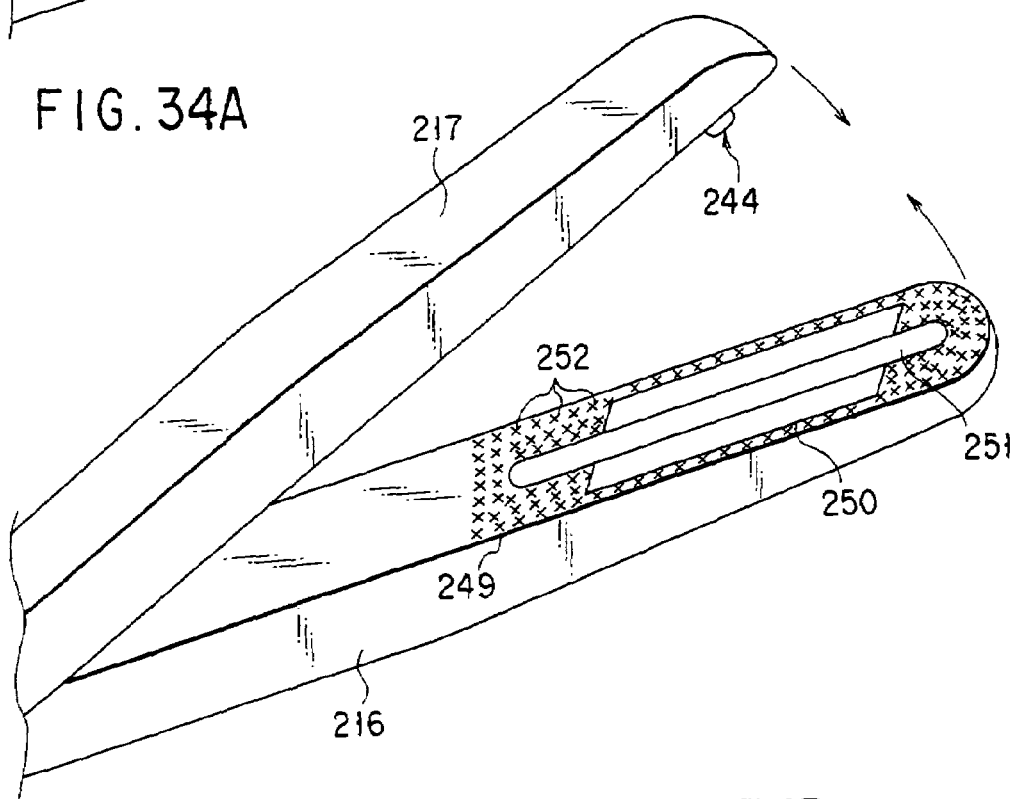
FIG. 34B is a perspective view showing a guide groove of a grasp surface of the other jaw in the coagulating/dissection treatment instrument according to the twenty-fifth embodiment.

FIGS. 33, 34A and 34B show a twenty-fifth embodiment of the present invention. In the present embodiment, a structure of the treatment portion 218 at the tip of the treatment embodiment main body 212 in the coagulating/cutting treatment instrument 211 according to the twenty-first embodiment (refer to FIGS. 28, 29A and 29B) is modified as follows:

That is, at one jaw 217 of the treatment portion 218 according to the present embodiment, as shown in FIG. 34A, a planar heating element 242 is provided partially of a grasp surface 241 meshed with the other jaw 216.

Further, a cutting instrument guide groove 243 extended in the centerline direction of the jaw 217 is formed at the substantial center site of the grasp surface 241 of this jaw 217. This cutting instrument guide groove 243 is extended from the tip to the end of this grasp surface 241 beyond the heating element 242. In this cutting instrument guide groove 243, a cutting instrument 244 having structure different from the scissor blades 227 and 228 according to the twenty-first embodiment is slidably arranged along this cutting instrument guide groove 243.

At this cutting instrument 244, a hook portion 246 to be protruded to the outside of the cutting instrument guide groove 243 is connected to the tip of a bar-shaped shank portion 245. A nichrome wire 247 is mounted on this hook portion 246. Further, a finger hoot portion 248 protruded to the outside of the cutting instrument guide groove 243 is formed at the end of the shank portion 245 of the cutting instrument 244 as shown in FIG. 33.

In addition, at the jaw 216 side, a planar heating element 250 is provided partially at the grasp portion 249 meshed with the grasp phase 241 of the opposite jaw 217, as shown in FIG. 34B. Further a hook portion guide groove 251 having the hook portion 246 of the cutting instrument 244 inserted thereinto is formed at the substantial center side of the grasp surface 249 of this jaw 216. This hook portion guide groove 251 is extended from the tip side of the grasp surface 24 to the end side beyond the longitudinal length of the heating element 250. When a pair of jaws 216 and 217 is meshed with each other, the depth of this hook portion guide groove 251 is set in dimensions in which the hook portion 246 on the tip side of the cutting instrument 244 is substantially recessed.

A fine irregularity 252 for preventing slip-off is formed on each of the grasp surfaces 241 and 249 of a pair of jaws 216 and 217, and on the surface of the heating elements 242 and 250.

Further, power supply cables 253 and 254 are connected, respectively to the heating elements 242 and 250, and are led out, respectively, from the finger insert rings 219 and 220. A power supply cable 255 is also connected to a nichrome wire 247. This power supply cable 255 is led out from the finger insert ring 220. The led-out power supply cables 253, 254, and 255 are connected to a power supply source (not shown).

Now, an operation in the above structure will be described. In the present embodiment, when the coagulating/cutting treatment instrument 211 is used, a tip side hook portion of the cutting instrument 244 is maintained in advance at a standby position at which the hook portion is moved to be positioned at the terminal end portion of the tip side of the cutting instrument guide groove 243 of the jaw 217. In this state, fingers are inserted into the finger insert rings 219 and 220 of the frontal operating portion 221. Then, jaws 216 and 217 of the treatment instrument main boy 212 are operated to be opened, and closed and a target site (for example, blood vessel) is grasped between a pair of jaws 216 and 217. In this state, power is supplied to the heating elements 242 and 250, the heating elements 242 and 250 are heated and the blood vessel is coagulated.

Subsequently, while this grasped state is maintained, power is supplied to the nichrome wire 247. While the nichrome wire 247 is heated, a finger hook portion 248 is pulled to the end side. Then, the nichrome wire 247 is moved from the tip side to the end side of the jaw 217. In this manner, a blood-coagulated site is cut by the nichrome wire 247.

With the above structure, the following effect is obtained. That is, in the present embodiment, since coagulation and dissection can be performed continuously while the target site is grasped, positioning operation during cutting is not required, and there is no worrying about mistaking a cutting site. Therefore, the operator's burden is reduced, and precision in coagulating/cutting treatment is improved.

FIGS. 35A to 35C, 36A and 36B show a twenty-sixth embodiment of the present invention. FIG. 35A shows a schematic structure of the coagulating treatment instrument 301 according to the present embodiment. The main body 302 of the coagulating treatment instrument 301 according to the present embodiment is provided with two scissor constituent members 303 and 304. These scissor constituent members 303 and 304 are placed in a state in which the intermediate portions substantially cross with each other. Further, a fulcrum pin 305 for rotatably connecting these scissor constituent members 303 and 305 with each other is arranged at the cross section of the scissor constituent members 303 and 304.

A treatment portion 308 comprising a pair of jaws 306 and 307 capable of being opened and closed, which grasps the patient's body tissue, is arranged at the tip of the treatment instrument main body 302. This treatment portion 308 is molded in the substantially same shape a release forceps.

Further, substantially elliptical finger insert rings 309 and 310 are formed at the proximal ends of the scissor constituent members 303 and 304. A frontal operating portion 311 for opening/closing a pair of jaws 306 and 307 is formed by portions of these finger insert rings 309 and 310.

A curve portion 312 gently curved in substantial arc shape as shown in FIG. 35B is formed at the treatment portion 308 of the treatment instrument main body 302. Further, ceramic heaters (heater means) 313 and 314 for coagulating the patient's body tissue is provided on a contact surface side with the patient's body tissue as shown in FIG. 35A.

Figure 36A:
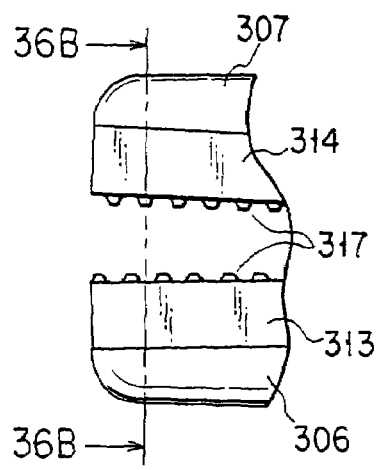
FIG. 36A is an enlarged side view showing the jaw section of the coagulating treatment instrument according to the twenty-sixth embodiment.
Figure 36B:
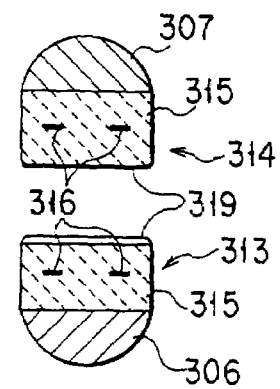
FIG. 36B is a cross sectional view taken along the line 36B-36B of FIG. 36A.

The ceramic heaters 313 and 314 consist of a heat transmitting portion 315 made of ceramic that is an insulation material as shown in FIG. 36B, and a heating element 316 recessed inside this heat transmitting portion 315. Types of ceramics of the heat transmitting portion 315 include alumina; aluminum nitrate; silicon nitrate or the like. Further, a material of the heating element 316 is often selected from among metals such as tungsten. In general, the heat transmitting portion 315 and heating element 316 are burned integrally, and the ceramic heaters 313 and 314 are molded.

In addition, a tooth portion 317 for preventing the patient's body tissue from slip-off as shown in FIG. 35C is provided on the surface of the heating element 316 of each of the ceramic heaters 313 and 314. In the present embodiment, this tooth portion 317 is formed by a number of substantially trapezoidal protrusions 318 protruded on the surface of the heating element 316. This tooth portion 317 is molded by cutting the surface of the heating element 316.

Further, a Teflon coating layer 319 for covering the surface of the heating body 316 with a Teflon coat is formed on the outer surface (constant surface with the patient's body tissue) of the heating element 316 of each of the ceramic heaters 313 and 314 to prevent scorching (adhering) of the patient's body tissue.

As shown in FIG. 35A, insulation lead wires 320 and 321 are arranged, respectively, at the scissor constituent members 303 and 304. At the tip, the insulation lead wire 320 on one scissor constituent member 303 side is connected to the ceramic heater 313. At the tip, the insulation lead wire 321 on the other scissor constituent member 304 side is connected to the ceramic heater 314.

In addition, one cable connection portion 322 is protruded on the outer periphery of the finger insert ring 309 on the scissor constituent member 303 side. One cable connection portion 323 is protruded similarly on the outer periphery of the finger insert ring 310 on the scissor constituent member 304 side. At the proximal end, the insulation lead wire 320 is connected to the cable connection portion 322 on the scissor constituent member 303 side. The insulation lead wire 321 is connected to the cable connection portion 323 on the scissor constituent member 304 side. Further, to these cable connection portions 322 and 323, the connector cables 324 and 325 each connected to a power supply unit (not shown) at one end is detachably connected at the other end. Then, power is supplied to the ceramic heaters 313 and 314 from the power supply unit (not shown).

Now, an operation of the coagulating treatment instrument 301 with the above structure according to the present embodiment will be described. First, the treatment portion 308 at the tip of the coagulating treatment instrument 301 is inserted into the patient's body tissue including a site targeted for treatment such as blood vessel (not shown) while the treatment portion 308 is closed. Thereafter a pair of jaws 306 and 37 is opened, whereby a site targeted for treatment such as blood vessel is released from the other patient's body tissue and is exposed.

Subsequently, the released blood vessel or the like is grasped while it is compressed between the jaws 306 and 307 of the coagulating treatment instrument 301 with a proper pressure suitable to the coagulating treatment. In this state, when a power supply unit (not shown) is output, power is supplied to the heating element 316 of the ceramic heaters 313 and 314 of each of the jaws 306 and 307 via the connector cables 320 and 321. The heating element 316 is heated by electrical resistance while the power is supplied; the heat transmitting portion 315 is heated; and the patient's body tissue is coagulated at the site targeted for treatment such as blood vessel coming into contact with the surface of this heat transmitting portion 315. The heat transmitting portion 315 is made of a insulating element, and a current supplied to the heating element 316 does not leak the patient's body tissue at the site targeted for treatment.

With the above structure, the following effect is obtained. That is, in the present embodiment, the ceramic heaters 313 and 314 are arranged at the jaws 306 and 307 of the treatment instrument main body 302. Thus, there is no need for applying another insulation coating to the ceramic heaters 313 and 314 of the jaws 306 and 307 each, and there is an effect that the durability and reliability of the coagulating treatment instrument 301 can be improved.

Figure 37:
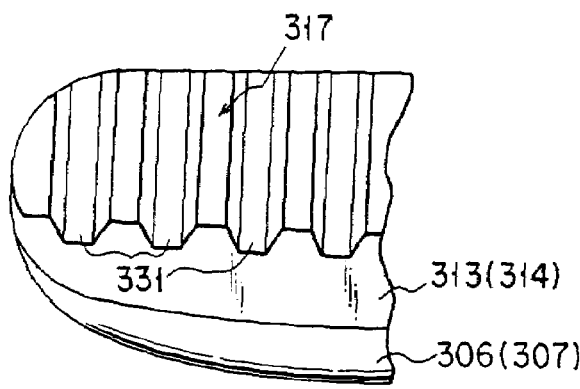
FIG. 37 is a perspective view of essential portions showing a modified example of the jaw of the coagulating treatment instrument according to the twenty-sixth embodiment.

FIG. 37 shows a modified example of the jaws 306 and 307 of the coagulating treatment instrument 301 according to the twenty-sixth embodiment. In the present modified example, the tooth portion 317 on the surface of each of the ceramic heaters 313 and 314 of the jaws 306 and 307 is formed by providing a plurality of transverse grooves 331.

Figure 38:
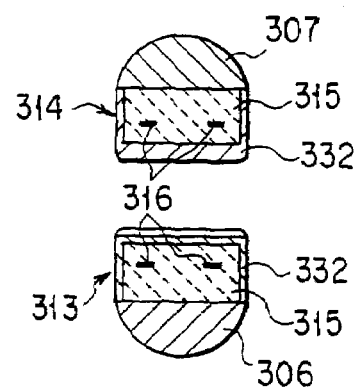
FIG. 38 is a cross sectional view of essential portions of a coagulating treatment instrument showing a twenty-seventh embodiment of the present invention.
Figure 39A:
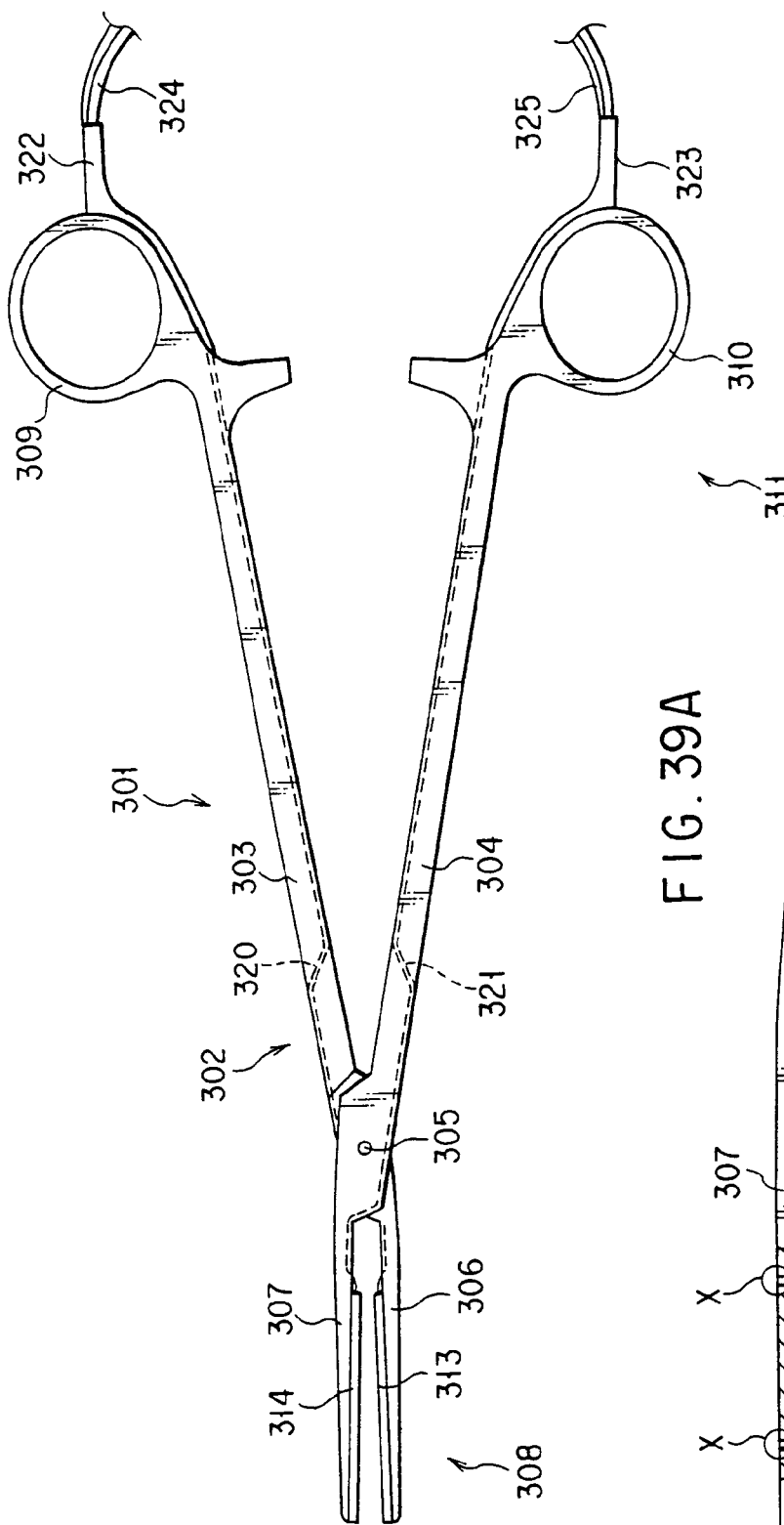
FIG. 39A is a side view of the entire coagulating treatment instrument showing a twenty-eighth embodiment of the present invention.
Figure 39B:
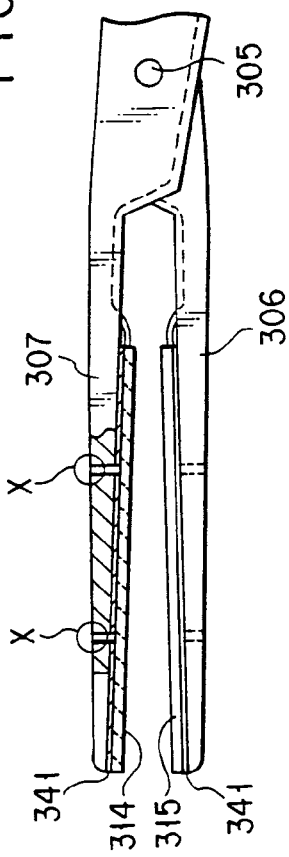
FIG. 39B is a sectional side view of essential portions showing a part of jaw of the coagulating treatment instrument according to the twenty-eighth embodiment.

FIG. 38 shows a twenty-seventh embodiment of the present invention. In the present embodiment, the ceramic heaters 313 and 314 of the jaws 306 and 307 of the coagulating treatment instrument 301 according to the twenty-sixth embodiment (refer to FIGS. 35A to 35C, 36A and 36B) are covered with a reinforce metal cover 332. It is desirable that a Teflon for preventing adhesion is coated on the surface of the reinforce metal cover 332.

In the present embodiment, the ceramic heaters 313 and 314 are covered with the reinforce metal cover 332, and thus, there is an effect that the strength of the jaws 306 and 307 of the coagulating treatment instrument 301 can be improved more significantly. The present invention may be a treatment instrument suitable to surgery under endoscope without being limited to the above embodiment.

FIGS. 39A, 39B, 40A and 40B show a twenty-eighth embodiment of the present invention. In the present embodiment, a structure of a fixing portion for fixing the ceramic heaters 313 and 314 to the jaws 306 and 307 of the treatment instrument main body 302 in the coagulating treatment instrument 301 according to the twenty-sixth embodiment (refer to FIGS. 35A to 35C, 36A and 36B) is modified as follows:

That is, in the present embodiment, as shown in FIGS. 40A and 40B, a connection plate (an intermediate connection member) 341 is brazed and connected to the inner surfaces of the ceramic heaters 313 and 314 (bonding surface with the jaws 306 and 307). This connection plate 341 may be a thin metal plate to decrease thermal stress during brazing, and is usable to be a stainless steel or a copal (a metal containing iron and cobalt).

Further, a plurality of connection pins 342 are protruded at the connection plate 341. Here, a hole 343 having connection pins 342 of the connection plate 341 inserted thereinto is formed at the jaws 306 and 307. Each connection pins 342 of the connection plate 341 has been inserted into the hole 343 of the jaws 306 and 307, and then, is fixed to the jaws 306 and 307 by bonding or laser-welding the upper surface portion around the hole 343 (X portion indicated by being surrounded by circle in FIG. 39B). Alternatively, the connection pin 342 may be used as a screw. Furthermore, as shown in FIG. 40C, the pins 342 are directly brazed and connected to the ceramic heaters 313 and 314.

Instead of blazing, connection between the ceramic heaters 313, 314 and the connection plate 341 may be made by bonding in which strength is slightly reduced. In addition, connection between the connection plate 341 and the jaws 306, 307 is directly bonded without using the connection pin 342.

With the above structure, the following effect is obtained. That is, in the present embodiment, when the ceramic heaters 313 and 314 are fixed to the jaws 306 and 307 each of the treatment instrument main body 302 in the coagulating treatment instrument 301, after a thin connection plate 341 has been blazed to be connected to the ceramic heaters 313 and 314, each connection pin 342 of the connection plate 341 is inserted into the hole 343 of the jaws 306 and 307. In this state, such each connection pin 342 is mechanically connected to the jaws 306 and 307 by bonding or laser-welding. Therefore, intervals between the resilient jaws 306, 307 formed of a metal and the hard, brittle ceramic heaters 313, 314 are linked with each other via each connection pin 342 of the connection plate 341. A resilience of the jaws 306 and 307 is absorbed by a slight gap between the ceramic heaters 313, 314 and the jaws 306, 307, whereby a load acted on the ceramic heaters 313 and 314 can be reduced.

As a result, ceramic heaters 313 and 314 can be reliably and easily linked with the jaws 306 and 307 with significantly different ceramics and thermal expansion rate.

Further, as in the case in which the hard, brittle ceramic heaters 313 and 314 are directly blazed to be rigidly connected to the jaws 306 and 307 with great volume and thermal expansion rate, an excessive load is prevented from being applied to the ceramic heaters 313 and 314, and there is an effect that strength of the link portion between the ceramic heaters 313, 314 and the jaws 306, 307 can be improved. In particular, the connection plate 341 is made of a copal with low thermal expansion rate, and there is an effect that the link strength can be improved more significantly.

FIG. 41A shows a first modified example of a mount structure of the connection plate 341 for linking between the jaws 306, 307 of the treatment instrument main body 302 and the ceramic heaters 313, 314 in the coagulating treatment instrument 301 according to the present modified example. In the present embodiment, a heater fixing claw 341a is protruded on the link portion side with the ceramic heaters 313 and 314 in the connection plate 341, and a jaw fixing claw 341b is protruded on the link portion side of the jaws 306 and 307. These heater fixing claw 341a and jaw fixing claw 341b are extended partially or over a full length of the connection plate 341.

Structurally, the heater fixing claw 341a of the connection plate 341 is mechanically engaged with the ceramic heaters 313 and 314 by means of caulking or the like, and the jaw fixing claw 341b is also engaged with the jaws 306 and 307 by means of caulking or the like. The heater fixing claw 341a may be provided at the jaws 306 and 307.

FIG. 41B shows a second modified example of a mount structure of the connection plate 341 for linking between the jaws 306, 307 of the treatment instrument main body 301 and the ceramic heaters 313, 314 in the coagulating treatment instrument 301 according to the twenty-eighth embodiment. In the present modified example, the connection plate 341 is formed in shape covering bottom surfaces of the ceramic heaters 313 and 314, and a fixing claw 341c protruded on both sides of this connection plate 341 is mechanically engaged with the jaws 306 and 307 together with the ceramic heaters 313 and 314 by means of caulking or the like.

In the above first and second modified examples, as in the coagulating treatment instrument 301 according to the twenty-eighth embodiment, there is an effect that the ceramic heaters 313 and 314 can be reliably and easily linked with the jaws 306 and 307 with significantly different thermal expansion rate from ceramics.

FIGS. 42A and 42B show a twenty-ninth embodiment of the present invention. In the present embodiment, a structure of the fixing portion for fixing the ceramic heaters 313 and 314 to the jaws 306 and 307 of the treatment instrument main body 302 in the coagulating treatment instrument 301 according to the twenty-eighth embodiment (refer to FIGS. 39A, 39B, 40A and 40B) is modified as follows:

That is, in the present embodiment, a split shape portion 342a is provided at the connection pin 342 of the connection plate 341 according to the twenty-eighth embodiment. At the tip of this split shape portion 342a, an engagement portion 342b having large diameter is provided. When this connection pin 342 has inserted into the hole 343 of the jaws 306 and 307, an engagement portion 342b at the tip of the split shape portion 342a is engaged with a peripheral edge site of the hole 343 of the jaws 306 and 307, whereby the ceramic heaters 313 and 314 are freely and detachably fixed to the jaws 306 and 307.

In the present embodiment, as in the coagulating treatment instrument 301 according to the twenty-eighth embodiment, there is an effect that the ceramic heaters 313 and 314 can be reliably and easily linked with the jaws 306 and 30 with significantly different thermal expansion rate from ceramics.

Figure 43:
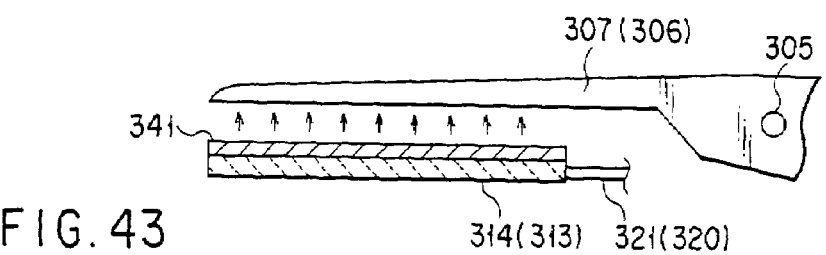
FIG. 43 is a sectional side view partially showing a state before mounting the intermediate connecting member of the jaw in the coagulating treatment instrument according to a thirtieth embodiment of the present invention.

FIG. 43 shows a thirtieth embodiment of the present invention. In the present embodiment, the connection plate 341 for fixing the ceramic heaters 313 and 314 to the jaws 306 and 307 of the treatment instrument main body 302 in the coagulating treatment instrument 301 according to the twenty-eighth embodiment (refer to FIGS. 39A, 39B, 40A and 40B) is formed of an elastic member such as rubber. In the present embodiment, the connection plate 341 is bonded with the ceramic heaters 313, 314 and the jaws 306, 307, respectively, and fixed thereto.

With the above structure, the connection plate 341 is made of an elastic member such as rubber. In this manner, there is an effect that resilience of the resilient jaws 306 and 307 formed of a metal material can be positively absorbed by the elastic member of the connection plate 341, and a load acted to the ceramic heaters 313 and 314 can be reliably reduced.

Figure 44:
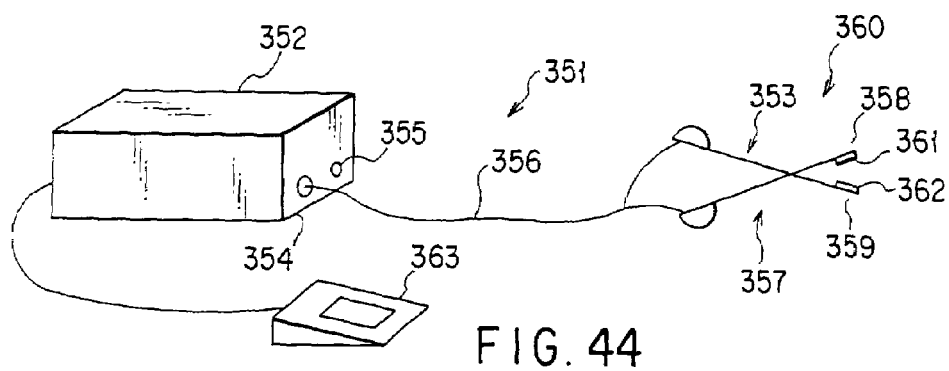
FIG. 44 is a perspective view showing a schematic configuration of the entire system of a coagulating treatment instrument according to a thirty-first embodiment of the present invention.
Figure 45:
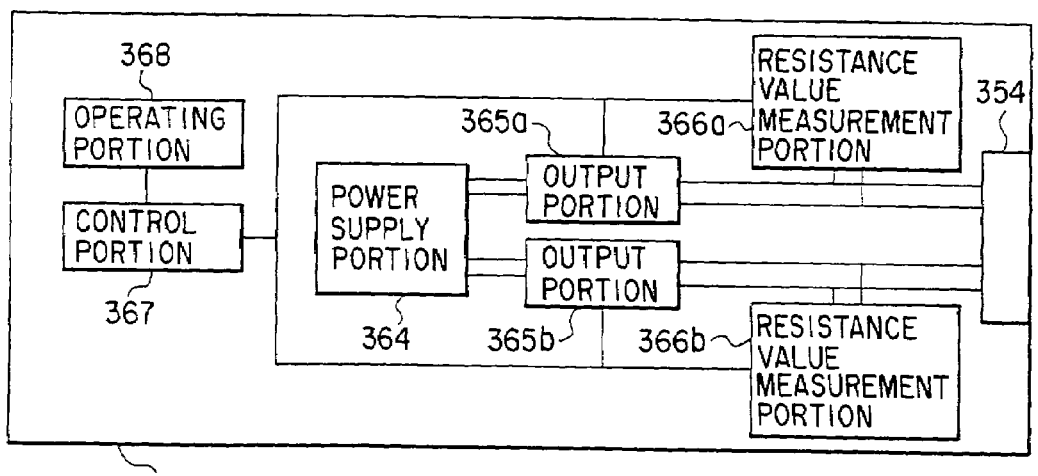
FIG. 45 is a schematic structural view showing an electric circuit of the coagulating treatment instrument system according to the thirty-first embodiment.

FIGS. 44 and 45 show a thirty-first embodiment of the present invention. FIG. 44 shows a schematic structure of the entire system of the medical treatment embodiment 351 according to the present embodiment. A system of the medical treatment instrument 351 according to the present embodiment is provided with a power supply unit 352 and a substantial scissors-shaped, thermal coagulating/cutting forceps 353. An output connector 354 and an initial resistance measurement switch 355 are provided in front of the power supply unit 352. A thermal coagulating/cutting forceps 353 is connected to the output connector 354 of the power supply unit 352 via a cable 356.

A treatment portion 360 comprising a pair of jaws 358 and 359 capable of being opened and closed, which grasps the patient's body tissue is arranged at the tip of the main body 357 of the thermal coagulating/cutting forceps 353. Further, heaters 361 and 362 are incorporated into the jaws 358 and 359, respectively. These heaters 361 and 362 are ceramic heater, for example.

A foot switch 363 for controlling power supply of the heaters 361 and 362 is connected to the power supply unit 352. Although there is shown an example when the foot switch 363 is connected to the power supply unit 352, a hand switch for controlling power supply of the heaters 361 and 362 may be provided at the thermal coagulating/cutting forceps 353.

FIG. 45 is a block diagram showing an electric circuit inside the power supply unit 352. A power supply portion 364 for a heater power source is provided inside the power supply unit 352. This power supply portion 364 is a constant voltage power source, for example.

Further, two heaters 361 and 362 of the thermal coagulating/cutting forceps 353 are provided with output portions 365a, 365b and resistance value measurement portions 366a, 366b, respectively. An individually independent output control and resistance value measurement are possible for the two heaters 361 and 362 of the thermal coagulating/cutting forceps 353.

The resistance value measurement portions 366a, 366b and the output portions 365a, 365b are connected to a control portion 367, and individually suitable output correction can be performed. An operating portion 368 is connected to this control portion 367. This operating portion 368 is provided with the initial resistance measurement switch 355.

Now, an operation in the above structure will be described. When a system of the medical treatment instrument 351 according to the present embodiment is used, the operation is controlled as follows:

While the medical treatment instrument 351 according to the present embodiment is connected as shown in FIG. 44, the initial resistance measurement switch 355 is first pressed.

Then, the resistance value measurement portions 366a and 366b measure the respective heater resistance values of the heaters 361 and 362 of the thermal coagulating/cutting forceps 353, and sends data to the control portion 367. This values are judged as initial resistance values of the heaters 361 and 362.

When measurement of this initial resistance values has been completed, an output of the foot switch 363 is made possible. Even if the foot switch 363 is pressed before measuring the initial resistance values of the heaters 361 and 362 of the thermal coagulating/cutting forceps 353, a buzzer or the like indicates a warning, and the output of the foot switch 363 is made impossible.

When the foot switch 363 is pressed, the control portion 367 sends an output correction signal to the output portions 365a and 365b according to the respective initial resistance values of the heaters 361 and 362. This correction method is as follows:

Assuming that a power voltage is denoted by V, and a heater initial resistance value is denoted by Ri, (1) The voltage V is adjusted so that V2/Ri becomes a predetermined value, and a constant voltage is output by the voltage V;

(2) A duty ratio of the voltage is denoted by D, and output is performed at the voltage duty ratio of D so that (V×D)2/Ri become a predetermined value.

The output portions 365a and 365b perform outputting using any one of the above correction methods.

With the above structure, the following effect is obtained. That is, in the present embodiment, even if heater resistance values are dispersed, heating characteristics of the heaters 361 and 362 can be identical substantially, and stable coagulation capability can be obtained.

Figure 46:
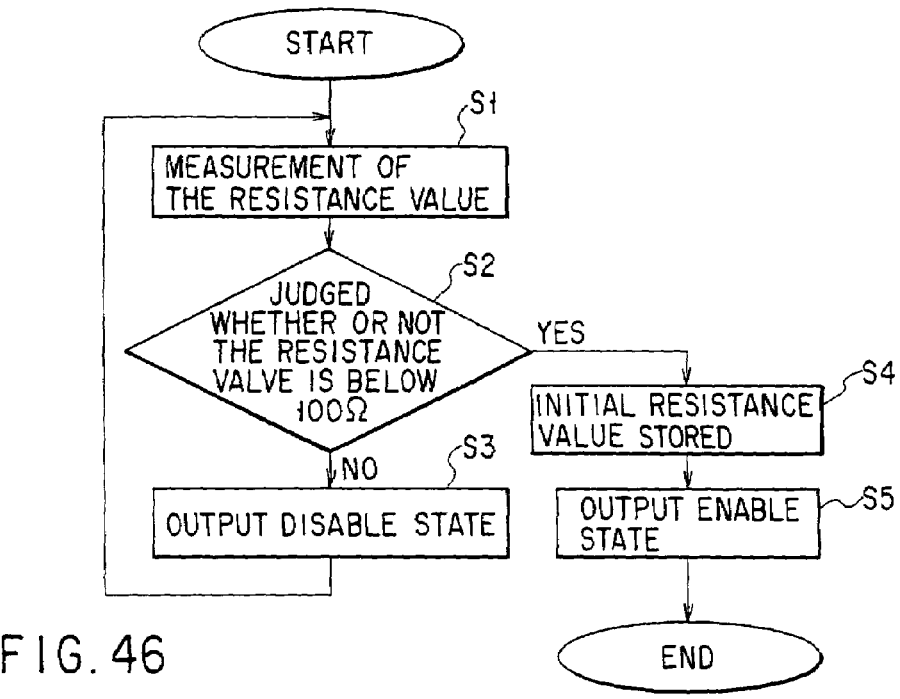
FIG. 46 is a flowchart showing an operation of the coagulation treatment instrument according to a thirty-second embodiment of the present invention.

Further, FIG. 46 shows a thirty-second embodiment of the present invention. In the present embodiment, an initial resistance measurement switch 355 is omitted from the power supply unit 352 according to the thirty-first embodiment (refer to FIGS. 44 and 45). Further, while the thermal coagulating/cutting forceps 353 is connected after the power supply unit 352 has been current-carried, the control portion 367 controls operation in accordance with a flowchart shown in FIG. 46. The other portions are same as those in the system of the medical treatment instrument 351 according to the thirty-first embodiment. Like elements identical to those in the system of the medical treatment instrument 351 according to the thirty-first embodiment are denoted by like reference numerals, and a description thereof will be omitted here.

Now, an operation in the above embodiment will be described. In the present embodiment, while the thermal coagulating/cutting forceps 353 is connected after the power supply unit 352 has been current-carried, the control portion 367 controls operation in accordance with a flowchart shown in FIG. 46. First, in step S1, measurement of the resistance value is repeated in the resistance value measurement portions 366a and 366b with certain time intervals. In the next step S2, it is judged whether or not the resistance value is below 100Ω. Here if the thermal coagulating/cutting forceps 353 is not connected, the resistance value is an open value. When, in step S2, it is judged that the resistance value is not below 100Ω, processing goes to the next step S3, and it is judged that it is in an output disable state. In this case, processing returns to step S1, measurement of resistance values is repeated.

Further, in step S2, when it is judged that the resistance value is below 100Ω, processing goes to the next step S4. In step S4, a resistance value below 100Ω is stored as an initial resistance value. Subsequently, processing goes to the next step S5 in which switching operation is performed to enter an output enable state, and processing is ended. In the present embodiment, although a resistance value threshold is 100Ω, a value suitable to the heater used may be predetermined.

Thereafter, as in the thirty-first embodiment, when the foot switch 363 is pressed, an output corrected by the initial resistance value is performed.

With the above structure, an effect identical to that in the thirty-first embodiment is achieved. In the present embodiment, in particular, an initial resistance is measured automatically, and thus, there is an effect that operation of the thermal coagulating/cutting forceps 353 is further simplified.

Figure 47A:
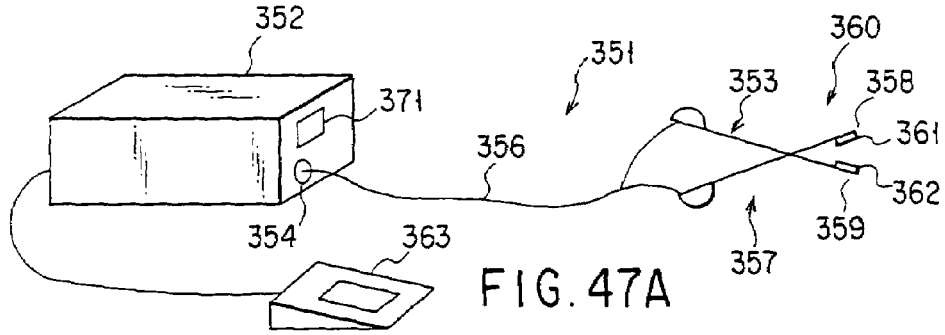
FIG. 47A is a perspective view showing a schematic configuration of the entire system of a coagulating treatment instrument in a thirty-third embodiment of the present invention.
Figure 47B:
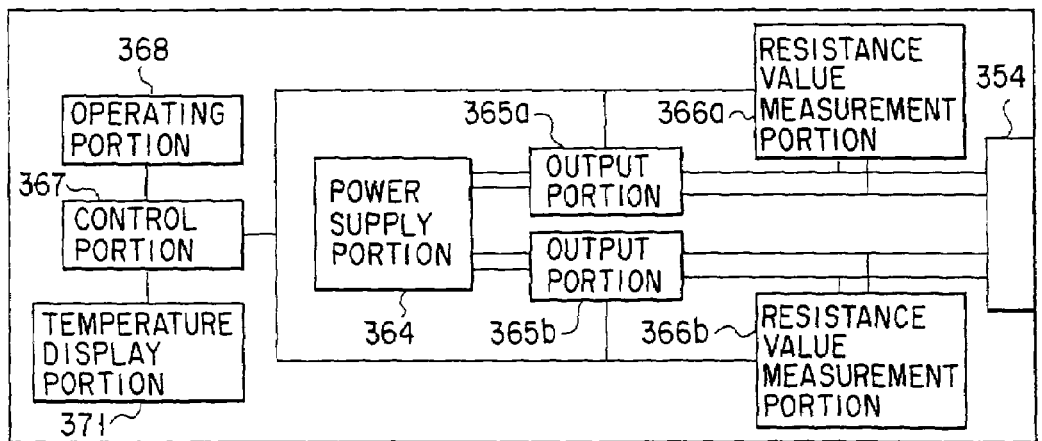
FIG. 47B is a schematic structural view showing an electric circuit of the coagulating treatment instrument system according to the thirty-third embodiment.

FIGS. 47A and 47B show a thirty-third embodiment of the present embodiment. In the present embodiment, a temperature display portion 371 is provided in the front surface of the power supply unit 352 according to the thirty-first embodiment (refer to FIGS. 44 and 45). This temperature display portion 371 is connected to the control portion 367.

This temperature display portion 371 is structured so that the temperatures of the heaters 361 and 362 of the thermal coagulating/cutting forceps 353 are displayed. The other portions are structurally identical to those in the system of the medical treatment instrument 351 according to the thirty-first embodiment. Like elements identical to those in the system of the medical treatment instrument 351 according to the thirty-first embodiment is denoted by like reference numeral, and a description thereof is omitted here.

Now an operation in the above structure will be described. In the present embodiment, as in the thirty-second embodiment (refer to FIG. 46), the power supply unit 352 is turned on, the thermal coagulating/cutting forceps 353 is connected, and then, an initial resistance value is measured.

Subsequently, the control portion 367 utilizes the fact that the resistance values of the heaters 361 and 362 are changed according to a temperature. Then, the control portion 367 calculates the temperatures of the heaters 361 and 362 of the thermal coagulating/cutting forceps 353 from the resistance measurement values of the resistance value measurement portions 366a and 366b. At this time, a temperature error due to dispersion in heater resistance values is corrected in view of the initial resistance value. The thus obtained heater temperatures are displayed on the temperature display portion 371.

A temperature displayed on the temperature display portion 371 may be any of the higher temperature, lower temperature, and average temperature of the heaters 361 and 362. In addition, a temperature display portion 371 may be employed such that both temperatures can be displayed. Further, it is obvious that an output of the power supply unit 352 may be controlled so that the heater temperature becomes a predetermined temperature.

With the above structure, the following effect is obtained. That is, in the present embodiment, there is an effect that the temperatures of the heaters 361 and 362 of the thermal coagulating/cutting forceps 353 can be measured without a temperature sensor. Even if there is dispersion in heater resistance values, there is an effect that temperature precision can be improved.

In the thirty-first embodiment (refer to FIGS. 44 and 45) to the thirty-third embodiment (refer to FIGS. 47A and 47B), a PTC heater (a heater formed of a positive temperature coefficient material) is used as heaters 361 and 362 of the thermal coagulating/cutting forceps 353.

With the above structure, in the case where a constant voltage is applied to the PTC heater, when the heater temperature reaches a Curie temperature, the resistance value rapidly increases, and then, heating is restricted. As a result, the temperature is controlled close to the Curie temperature.

With the above structure, the PTC heater is used as a heater, and thus, there is an effect that the heater curie temperature is set according to a member with lowest heat resistance temperature, thereby making it possible to easily produce a temperature limiter.

For example, the curie temperature is set to 200° C. or less in order to protect a Teflon coating of the forceps. Thus, in the case where an attempt is made to set the upper limit of the heater temperature to about 200° C. in order to protect the Teflon coating, when the PTC heater with curie temperature of 190° C. is employed, a desired temperature limiter can be structured without requiring a special circuit or control to be provided at the power supply unit 352 side.

In addition, the curie temperature is set to about 150° C. in order to prevent overheat of the patient's body tissue. In this manner, a temperature limiter can be provided without any special structure. Thus, the PTC heater is used as heaters 361 and 362 of the thermal coagulating/cutting forceps 353, thereby making it possible to easily provide a temperature limiter in all of the thirty-first to thirty-third embodiments.

FIGS. 48A to 48D show a thirty-fourth embodiment of the present invention. FIG. 48A shows a schematic structure of the coagulating treatment instrument 401 according to the present embodiment. The main body 402 of the coagulating treatment instrument 401 according to the present embodiment is provided with two scissor constituent members 403 and 404. These scissor constituent members 403 and 404 are placed in a state in which its intermediate portions substantially cross with each other. Further, a fulcrum pin 405 for rotatably linking these scissor constituent members 403 and 404 with each other is arranged at the cross section of these scissor constituent members 403 and 404.

A treatment portion 408 comprising a pair of jaws 406 and 407 capable of being opened and closed, which grasps the patient's body tissue, is arranged at the tip of the treatment portion main body 402. Further, the substantially elliptical finger insert rings 409 and 410 are formed at the proximal ends of the scissor constituent members 403 and 404, respectively. A frontal operating portion 411 for operating a pair of jaws 406 and 407 to be opened and closed is formed by portions of these finger insert rings 409 and 410.

In addition, a curve portion 412 gently curved in the substantial arc shape is formed at the treatment portion 408 of the treatment instrument main body 402 as shown in FIG. 48B. Further, at the jaws 406 and 407 of the treatment main body 402, as shown in FIG. 48A, the coagulating treatment unit 413 for coagulating the patient's body tissue is provided on the contact surface side with the patient's body tissue.

This coagulating treatment unit 413 is provided with a heater 414 fixed to each of the jaws 406 and 407 and a cover 415 for covering the outer surface of this heater 414, as shown in FIG. 48C. The heater 414 to be used includes a ceramic heater, a PTC heater (a heater formed of positive temperature coefficient material), and a semiconductor heater.

The cover 415 is made of a metal such as stainless or copper, is formed in the substantially same shape as the heater 414, and is thinly formed so as to improve thermal conductivity. Further, a tissue adhesion preventing treatment portion 416 for preventing adhesion of the patient's body tissue is provided at the outer full surface of this cover 415 as shown in FIG. 48D. Examples of this tissue adhesion preventing treatment portion 416 include a Teflon coating available from Dupon and a ceramic coating (plasma flame spraying) or the like.

A plurality of inwardly projected protrusion portions 417 are pressed to be provided on the inner surface of the cover 415. In the heater 414, recess portions 418 to be detachably engaged with the protrusion portions 417 are projected respectively at the corresponding position of each protrusion portion 417. When the cover 415 is mounted on the heater 414, this cover 415 is designed to be removably mounted on the heater due to the elastic deformation of the cover 415 itself. At this time, each recess portion 417 of the cover 415 is detachably engaged with each recess portion 418 of the heater 414.

The recess portion 418 may be provided at the jaws 406 and 407 so as to fix the cover 415 for covering the heater 414 to each of these jaws 406 and 407. Further, an irregularity 419 or the like for preventing slip-off of the patient's body tissue is provided at the lower surface of the cover 415 so as to prevent the slip-off of the patient's body tissue by the irregularity 419 of the cover 415 when the patient's body tissue is grasped between the jaws 406 and 407. Additional preventive treatment for preventing adhesion of the patient's body tissue may be applied to a site free of being covered with the cover 415 on the outer surface side of the jaws 406 and 407.

As shown in FIG. 48A, insulation lead wires 420 and 421 are arranged respectively at the scissor constituent members 403 and 404. At the tip, an insulation lead wire 420 on one scissor constituent member 403 side is connected to the heater 414 of the coagulating treatment unit 413 on the jaw 406 side. At the tip, an insulation lead wire 421 on the other scissor constituent member 404 side is connected to the heater 414 of the coagulating treatment unit 413 on the jaw 407 side.

One cable connection portion 422 is protruded at the peripheral surface of the finger insert ring 409 on the scissor constituent member 403 side. Similarly, one cable connection portion 423 is protruded at the peripheral surface of the finger insert ring 410 on the scissor constituent member 404 side. At a proximal end, the insulation lead wire 420 is connected to the cable connection portion 422 on the scissor constituent member 403 side. The insulation lead wire 421 is connected to the cable connection portion 423 on the scissor constituent member 404 side. Further, to one ends of these cable connection portions 422 and 423, connector cables 424 and 425 connected to the power supply unit (not shown) are removably connected at the other ends. From the power supply unit (not shown), power is supplied to the heater 414 of each of the jaws 406 and 407.

Now, an operation of the coagulating treatment instrument 401 with the above structure according to the present invention will be described here. When the coagulating treatment instrument 401 according to the present embodiment is used, the cover 415 is set to be mounted on the heater 414 in advance. In this state, a site targeted for treatment such as blood vessel (not shown) is inserted into the patient's body tissue, while the treatment portion 408 at the tip of the coagulating treatment instrument 401 is closed. Then, a site targeted for treatment such as blood vessel is released from the other patient's body tissue and is exposed by opening a pair of jaws 406 and 407.

Subsequently, the released blood vessel or the like is grasped between the jaws 406 and 407 of the coagulating treatment instrument 401 while it is compressed with a proper pressure. At this time, the patient's body tissue of the site targeted for blood vessel grasped between the jaws 406 and 407 is prevented from slip-off by the irregularity 419 on the lower surface of the cover 415, and the slip-off of the patient's body tissue is prevented.

In this state, when power is output from a power supply unit (not shown), the power is supplied to the heater 414 of each of the jaws 406 and 407. In this manner, thee patient's body tissue at the site targeted for treatment such as blood vessel grasped between the jaws 406 and 407 is coagulated.

In the case where the tissue adhesion preventing treatment portion 416 of the cover 415 is degraded by use of the coagulating treatment instrument 401, the cover 415 is removed from the heater 414. In this state, a new cover 415 is mounted on the heater 414.

With the above structure, the following effect is obtained. That is, in the case where the tissue adhesion preventing treatment portion 416 of the cover 415 is degraded by use of the coagulating treatment instrument 401, the cover 415 can be simply replaced with another one. Thus, the tissue adhesion preventing treatment portion 416 around the heater 414 can be always maintained in a proper state. Therefore, an effect of preventing the adhesion of the tissue around the heater 414 can be maintained over a long period, and there is an effect that maintenance cost due to the degradation of the patient's body tissue adhesion preventing treatment portion 416 can be reduced, making it advantageous in cost efficiency.

Figure 49A:
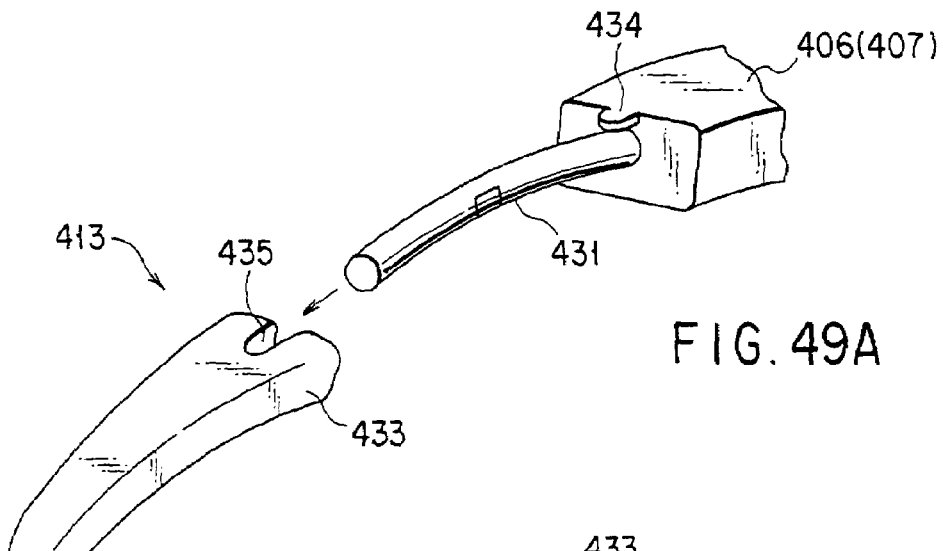
FIG. 49A is a perspective view of a heater cover of an upper jaw of a coagulating treatment instrument according to a thirty-fifth embodiment of the present invention.
Figure 49B:
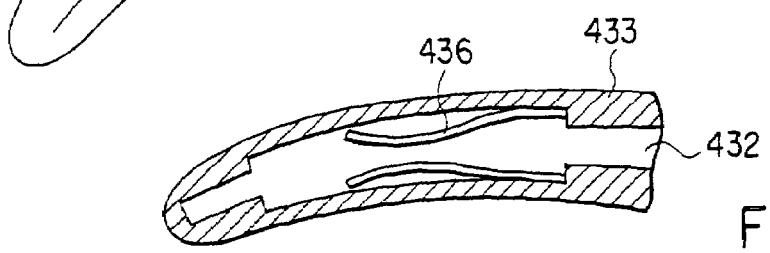
FIG. 49B is a longitudinal sectional view of the heater cover in the coagulating treatment instrument according to the thirty-fifth embodiment.

FIGS. 49A and 49B show a thirty-fifth embodiment of the present invention. In the present embodiment, a structure of the coagulating treatment unit 413 of the jaws 406 and 407 of the coagulating treatment instrument 401 according to the thirty fourth embodiment (refer to FIGS. 48A to 48D) is modified as follows:

That is, in the present embodiment, a bar-shaped heater 431 is protruded at the tip of each of the jaws 406 and 407 of the treatment instrument main body 402; a cover 433 comprising a heater insert hole 431 for inserting this heater 431 is provided; and the heater 431 is inserted into the heater insert hole 432 of this cover 431, whereby the entire outer surface of the heater 431 is covered with the cover 433. The cover 433 is formed in a curved shape as in the jaws 406 and 407 according to the thirty-forth embodiment. The tissue adhesion preventing treatment portion 416 similar to that in the thirty-fourth embodiment is provided on the peripheral surface of this cover 433.

Further, a positioning protrusion portion 434 is protruded at the tip surface of the jaws 406 and 407 as shown in FIG. 49A. In addition, a recess portion 435 to be detachably engaged with the positioning protrusion portion 434 is provided at the front side end of the cover 433. When the cover 433 is mounted on the heater 431, the recess portion 435 of the cover 433 is detachably engaged with the positioning protrusion portion 434 of the heater 431 so that the cover 433 is prevented from rotating with respect to the axial direction of the heater 431.

A plurality of plate spring members 436 to be brought into pressure-contact with the heater 431 are provided inside the heater insert hole 432 of the cover 433. When the heater 431 is inserted into the heater insert hole 432 of the cover 433, these plate spring members 436 are brought into pressure-contact with the heater 431 so as to ensure thermal conductivity of the heater 431.

In the present embodiment, the bar-shaped heater 431 protruded at the tip side of each of the jaws 406 and 407 is entirely covered with the cover 433, and thus an effect of preventing adhesion due to the tissue adhesion preventing treatment portion 416 of the cover 433 can be improved more significantly.

Figure 50A:
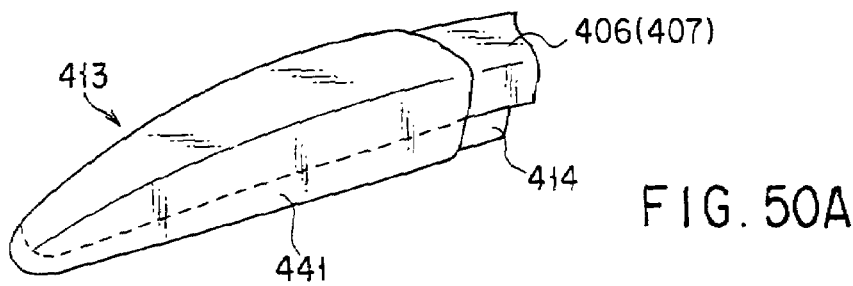
FIG. 50A is an enlarged perspective view showing a heater cover of a jaw of a coagulating treatment instrument according to a thirty-sixth embodiment of the present invention.

FIG. 50A shows a thirty-sixth embodiment of the present invention. In the present embodiment, a structure of the coagulating treatment unit 413 of each of the jaws 406 and 407 in the coagulating treatment instrument 401 according to the thirty-fourth embodiment (refer to FIGS. 48A to 48D) is modified as follows:

That is, in the present embodiment, a cover member 441 for covering the heater 414 fixed to each of the jaws 406 and 407 together therewith is provided. The cover member 441 according to the present embodiment is formed by an elastic tube. A tissue adhesion preventing treatment portion 416 similar to that in the thirty-fourth embodiment is provided at the outer full surface of this cover member 441.

An example of the cover member 441 formed by such elastic tube includes a Teflon tube. In addition, the cover member 441 is formed by a Teflon tube with heat shrink properties, and mounting on each of the jaws 406 and 407 may be implemented by utilizing the heating of the heater 414. In that case, when the cover member 441 is replaced with another one, the tube of the cover member 441 is cut to be removed from each of the jaws 406 and 407.

In the present embodiment, as in the thirty-fourth embodiment, an effect of preventing adhesion of the patient's body tissue can be maintained over a long period of time, and the maintenance cost due to the degradation of the patient's body tissue adhesion preventing treatment portion 416 is reduced, making it advantageous in cost efficiency.

Figure 50B:
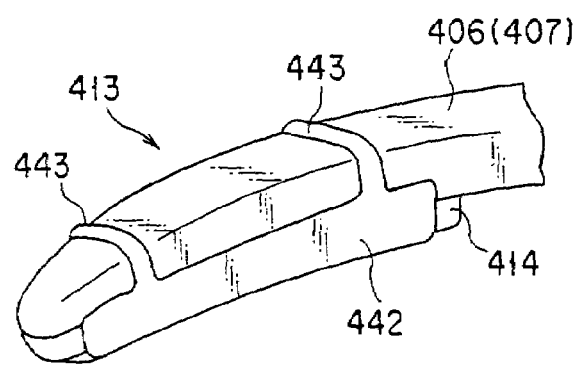
FIG. 50B is a perspective view showing a modified example of the heater cover of the jaw of the coagulating treatment instrument according to the thirty-sixth embodiment.

In addition, FIG. 50B shows a modified example of the cover member 441 of the coagulating treatment instrument 401 according to a thirty-sixth embodiment (refer to FIG. 50A). In this modified example, a thin film sheet (made of Teflon or the like) on which the adhesion preventing treatment portion 416 is formed by applying tissue adhesion preventing treatment is used, thereby to form a cover 442 as shown in FIG. 50B. This cover 442 is provided with a band-shaped fixing portion 443 to be fixed to each of the jaws 406 and 407. In this modified example, there is an effect that the manufacturing cost of the cover 442 is reduced.

FIGS. 51A to 51C and 52A show a thirty-seventh embodiment of the present invention. In the present embodiment, there is provided a thermal coagulating treatment instrument 454 comprising a scissor forceps 451 shown in FIG. 51A and a heater unit 453 detachable to a main body 452 of this scissor forceps 451. The forceps main body 452 is provided with two scissor constituent members 455 and 456. These scissor constituent members 455 and 456 are placed in a state in which their intermediate portions substantially cross with each other. Further, a fulcrum pin 457 for rotatably linking these scissor constituent members 455 and 456 with each other is arranged at the cross section of the scissor constituent members 455 and 456.

In addition, a treatment portion 460 comprising a pair of jaws 458 and 459 capable of being opened and closed, which grasps the patient's body tissue, is arranged at the tip of the forceps main body 452. Further, substantially elliptical finger insert rings 461 and 462 are formed at the proximal ends of the scissor constituent members 455 and 456. A frontal operating portion 463 for operating a pair of the jaws 461 and 462 to be opened and closed is formed by the portion of these finger insert rings 461 and 462.

Figures 51A, 51B:
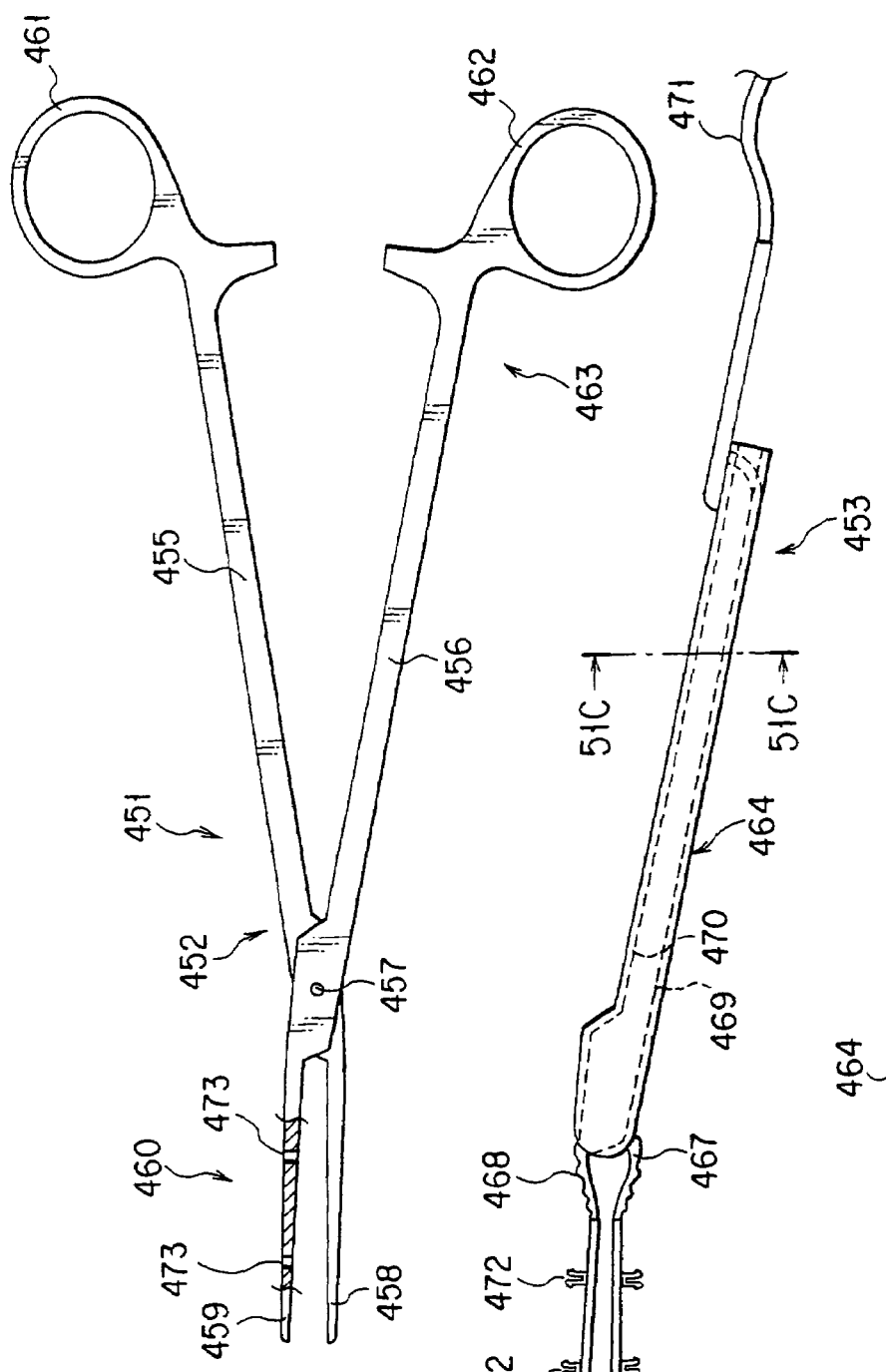
FIG. 51A is a front view of the entire coagulating treatment instrument showing a thirty-seventh embodiment of the present invention.
FIG. 51B is a front view of a heater unit according to the thirty-seventh embodiment.
Figure 51C:
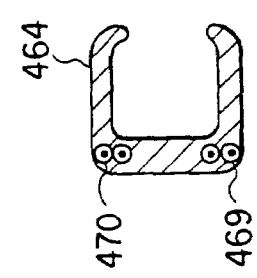
FIG. 51C is a cross sectional view taken along the line 51C-51C of FIG. 51B.

A substantially U-shaped unit main body 464 is provided at the heater unit 453 as shown in FIG. 51C. This unit main body 464 is designed to be detachably mounted on one scissor constituent member 456 side. Further, two heaters 465 and 466 are linked with the tip side of this unit main body 464 via elastic members 467 and 468. Tissue adhesion preventing treatment for preventing adhesion of the patient's body tissue is applied to the peripheral surfaces of the heaters 465 and 466. The elastic members 467 and 468 include synthetic resin, rubber or the like.

As shown in FIG. 51C, insulation lead wires 469 and 470 are arranged inside the unit main body 464. At one end, the insulation lead wire 469 is routed into the elastic member 467, and is connected to the heater 465. Further, at one end, the other insulation lead wire 470 is routed into the elastic member 468, and is connected to the heater 466.

In addition, a connector cable 471 for supplying power to the heaters 465 and 466 is provided in the front surface of the unit main body 464. This connector cable 471 and the heaters 465 and 466 are electrically connected with each other via the insulation lead wires 469 and 470.

Further, a plurality of tip-split connector pins 472 are provided at each of the heaters 465 and 466. Heater mounting engagement holes 473 are provided at the jaws 458 and 459 of the forceps main body 452. Each of the heaters 465 and 466 are detachably engaged by the connector pins 472 being inserted into the engagement holes 473 of the jaws 458 and 459 of the forceps main body 452.

Still further, the cover 415 and cover member 441 shown in the thirty-fourth embodiment (refer to FIGS. 48A to 48D) and the thirty-sixth embodiment (refer to FIG. 50A) are detachably provided at the heaters 465 and 466.

Now, an operation in the above embodiment will be described here. When the thermal coagulating treatment instrument 454 according to the present embodiment is used, one scissor constituent member 456 of the forceps main body 452 is inserted into a U-shaped opening of the unit main body 464 of the heater unit 453. In this manner, the unit main body 464 of the heater unit 453 is detachably mounted at one scissor constituent member 456 side of the forceps main body 452.

Subsequently, the connector pin 472 of each of the heaters 465 and 466 are inserted into the engagement hole 473 of each of the jaws 458 and 459 of the forceps main body 452, and the heaters 465 and 466 are detachably engaged with the jaws 458 and 459. In this manner, the heaters 465 and 466 are fixed to the jaws 458 and 459 of the forceps main body 452.

In the case where tissue adhesion preventing treatment of the heaters 465 and 466 is degraded by use of the thermal coagulating treatment instrument 454 according to the present embodiment, the heater unit 453 is removed from the forceps main body 452. Instead, a new heater unit 453 is designed to be mounted on the forceps main body 452.

With the above structure, in the case where tissue adhesion preventing treatment of the heaters 465 and 466 is degraded by use of the thermal coagulating treatment instrument 454 according to the present embodiment, only the heater unit 453 is replaced with another one without replacing the entire forceps main unit 452. Thus, there is an effect that tissue adhesion preventing treatment can always be maintained in a proper state, and the maintenance cost can be reduced.

Figure 52A:
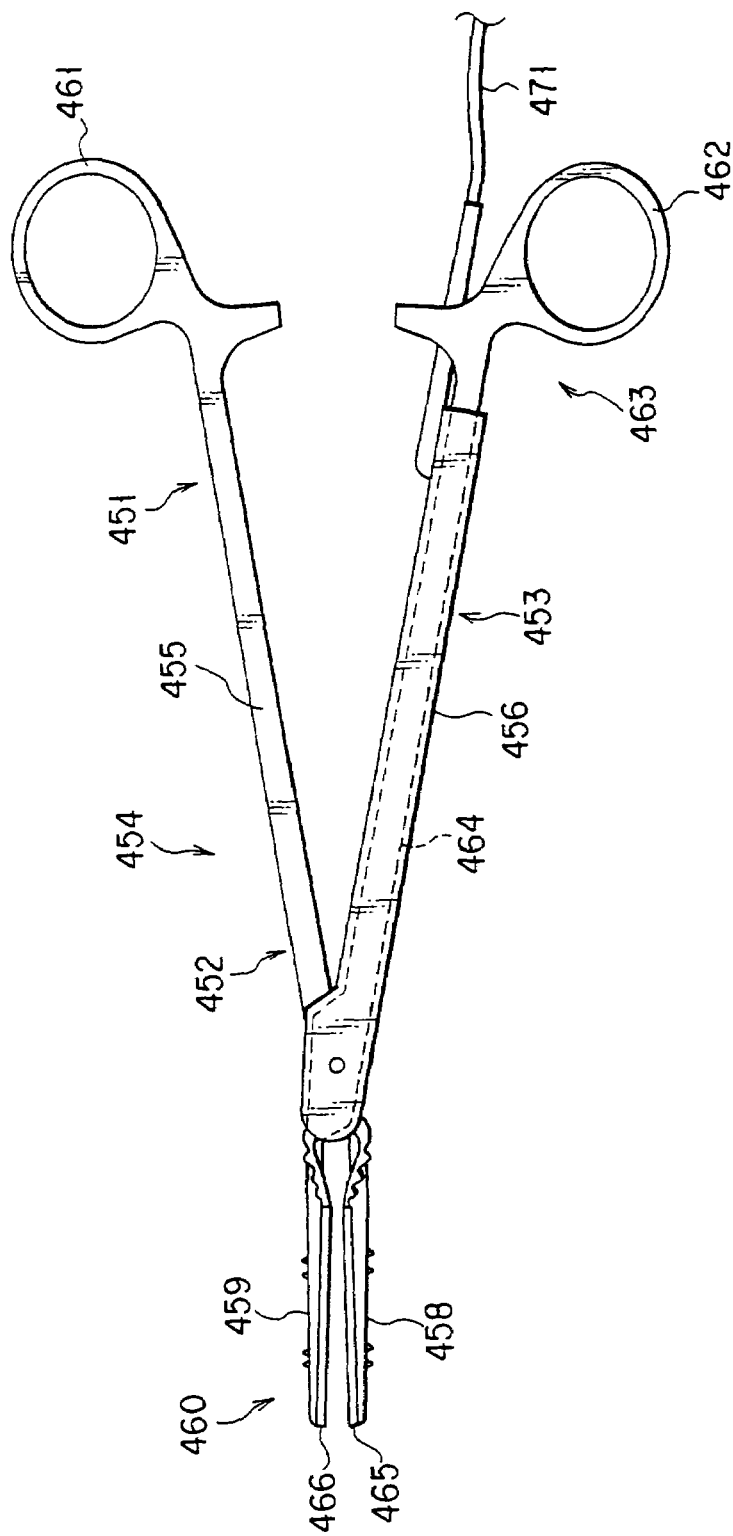
FIG. 52A is a front view showing a state in which a heater unit is mounted on the coagulating treatment instrument according to the thirty-seventh embodiment.
Figure 52B:
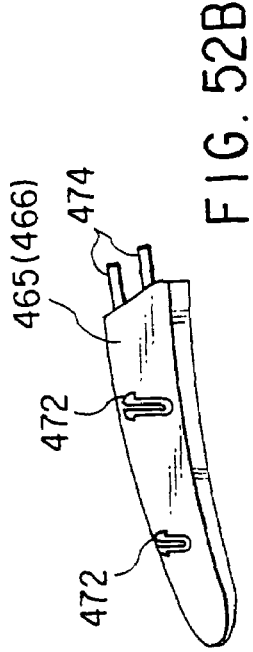
FIG. 52B is a perspective view of essential portions showing a modified example of the coagulating treatment instrument according to the thirty-seventh embodiment.

FIG. 52B shows a modified example of a thirty-seventh embodiment (refer to FIGS. 51A to 51C and 52A). In the present embodiment, lead electrodes 474 are provided at the heaters 465 and 466; and a heater receiving electrode (not shown) is provided at the forceps main body 452 of the scissor forceps main body 451 so that the lead electrodes 474 of the heaters 465 and 466 are detachably linked with the heater receiving electrode of this forceps main body 452. In the present embodiment, an effect similar to that in the thirty seventh embodiment will be obtained.

Figure 53A:
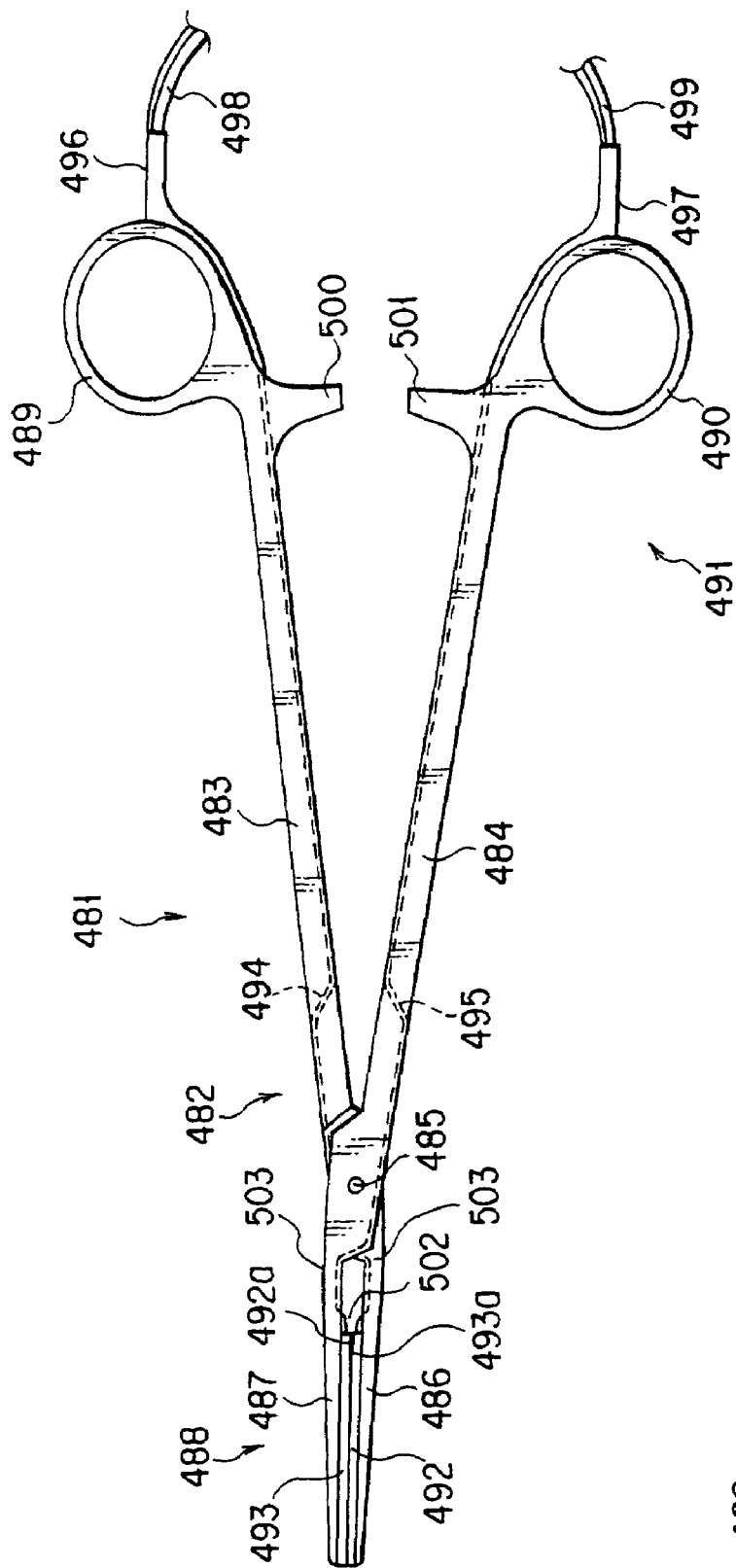
FIG. 53A is a front view of the entire coagulating treatment instrument showing a thirty-eighth embodiment of the present invention.

FIGS. 53A, 53B, 54A and 54B show a thirty-eighth embodiment of the present invention. FIG. 53A shows a schematic structure of a coagulating treatment instrument 481. The main body 482 of the coagulating treatment instrument 481 according to the present embodiment is provided with two scissor constituent members 483 and 484. These scissor constituent members 483 and 484 are placed in a state in which their intermediate portions substantially cross with each other. Further, a fulcrum pin 485 for rotatably linking the scissor constituent members 483 and 484 with each other is arranged at the cross section of the scissor constituent members 483 and 484.

A treatment portion 488 comprising a pair of jaws 486 and 487 capable of being opened and closed, which grasps the patient's body tissue, is arranged at the tip of the treatment instrument main body 482. Further, substantially elliptical finger insert rings 489 and 490 are formed at the proximal ends of the scissor constituent members 483 and 484. A frontal operating portion 491 for operating a pair of jaws 486 and 487 to be opened and closed is formed by the portions of these finger insert rings 489 and 490.

At the jaws 486 and 487 of the treatment instrument main body 482, as shown in FIG. 48A, heaters 492 and 493 for coagulating the patient's body tissue are provided on the contact surface side with the patient's body tissue. These heaters 492 and 493 include a ceramic heater, a PTC heater, a semiconductor heater or the like. The PTC heater has a rigid metal case.

As shown in FIG. 53A, insulation lead wires 494 and 495 are arranged, respectively, at the scissor constituent members 483 and 484. At the tip, the insulation lead wire 494 on one scissor constituent member 483 side is connected to the heater 492 on the jaw 486 side. At the tip, the insulation lead wire 495 on the other scissor constituent member 484 side is connected to the heater 493 of the jaw 487 side.

In addition, one cable connection portion 496 is protruded at the peripheral surface of the finger insert ring 489 on the scissor constituent member 483 side. Similarly, one cable connection portion 497 is protruded at the peripheral surface of the finger insert ring 490 on the scissor constituent member 484 side. At a proximal end, the insulation lead wire 494 is connected to the cable connection portion 496 on the scissor constituent member 483 side, and the insulation lead wire 495 is connected to the cable connection portion 497 on the scissor constituent member 484 side. Further, to these cable connection portions 496 and 497, connector cables 498 and 499 whose one ends are connected to a power supply unit (not shown) are detachably connected at the other ends. From the power supply unit (not shown), power is supplied to the heaters 492 and 493 of the jaws 486 and 487, respectively.

In addition, the upper and lower heaters 492 and 493 are provided with contact surfaces 492a and 493a coagulating in contact with the patient's body tissue, respectively. Further, on the proximal end side of each of the scissor constituent members 483 and 484, stoppers 500 and 501 for restricting the closed position of the operating portion 491 are protruded, respectively, at a position close to the finger insert rings 489 and 490 inwardly of the operating portion 491.

Figure 53B:
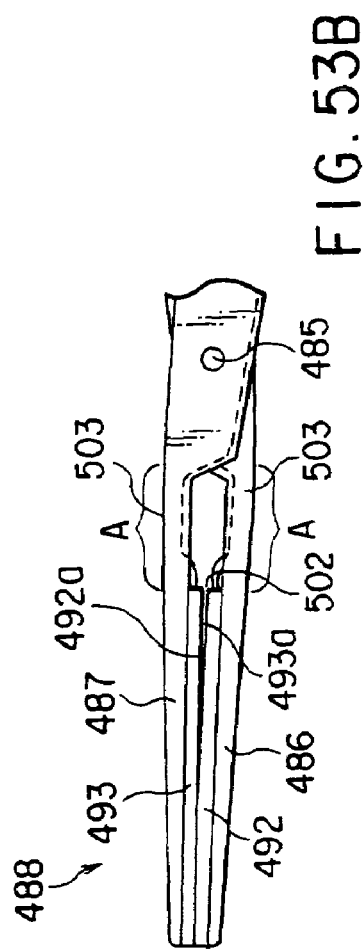
FIG. 53B is an enlarged front view showing the jaw at the tip of the coagulating treatment instrument according to the thirty-eighth embodiment.

In the present embodiment, when the jaws 486 and 497 of the treatment main body 482 is operated to be closed by the operating portion 491 of each of the scissor constituent members 483 and 484, as shown in FIGS. 53A and 53B, a gap 502 is formed between the rear ends of the contact surfaces 492a and 493a of the heaters 492 and 493 while the contact surfaces 492a and 493a of the heaters 492 and 493 of the jaws 486 and 497 abuts against each other at their tips. At this time, an interval between stoppers 500 and 501 of the scissor constituent members 483 and 484 is maintained so that these stoppers do not abut against each other. These scissor constituent members are set at a first closing operation position when the jaws 486 and 487 are operated to be closed each other.

Further, a closing force is strongly applied to the operating portion 491 from the first closing operation position when the jaws 486 and 487 shown in FIGS. 53A and 53B are operated to be closed with each other, whereby a path between the stoppers 500 and 501 of the scissor constituent member 483 and 484 moves to a position (a final closing operation position) such that the stoppers abut against each other. At this time, the contact surfaces 492a and 493a of the heaters 492 and 493 abut against their rear ends, and are set to be entirely closed.

Now, an operation in the above structure will be described here. In the present embodiment, when each of the jaws 486 and 487 is operated to be closed by the operating portion 491 of each of the scissor constituent members 483 and 484, these members are moved to the first closing operation position shown in FIGS. 53A and 53B. Then, the members are moved to the final closing operation position shown in FIGS. 54A and 54B. At the first closing operation position, when the contact surfaces 492a and 493a of the heaters 492 and 493 of the jaws 486 and 487 abut against each other at their tips, a gap 502 is formed between the rear ends of the contact surfaces 492a and 493a of the heaters 492 and 493. At this time, an interval between the stoppers 500 and 501 of the scissor constituent members 483 and 484 is maintained so that these stoppers do not abut against each other.

Further, a closing force is strongly applied to the operating portion 491 from the first closing operation position when each of the jaws 486 and 487 shown in FIGS. 53A and 53B is operated to be closed, whereby the stoppers 500 and 501 of the scissor constituent members 483 and 484 move to a position (a final closing operation position) such that these members do not abut against each other. At this time, a root side portion 503 of each of the jaws 486 and 487 is elastically deformed, and the contact surfaces 492a and 493a of the heaters 492 and 493 abut against each other at their rear ends, and the entire contact surfaces 492a and 493a of the heaters 492 and 493 are closed in their contact state.

When the contact surfaces 492a and 493a of the heaters 492 and 493 abut against each other at their rear ends, it is desirable that a load of 1 Kgf (9.8 N) or more is applied to an interval between the tips of the jaws 486 and 487.

In addition, the upper and lower stoppers 500 and 501 are adjusted to be in contact with each other at an interval between the contact surfaces 492a, 493a of the heater 492, 493 abut against each other at their rear ends. The abutment position of the upper and lower stoppers 500 and 501 can be adjusted by an adjustment screw or the like (not shown).

If the stoppers 500 and 501 are not provided, when a closing force is further applied from the final closing operation position shown in FIGS. 53A and 53B, the root side portion 503 of each of the jaws 486 and 487 is further elastically deformed. Then, a gap is provided at the tip of each of the contact surfaces 492a and 493a of the heaters 492 and 493 of the jaws 486 and 487. The range of elastic deformation of the jaws 486 and 487 depends on the mounting method of the heaters 492 and 493, and may exceed the range of A shown in FIG. 53A in the case where these heaters are mounted to the jaws 486 and 487 relatively loosely, for example.

With the above structure, the following effect will be obtained. That is, in the present embodiment, stoppers 500 and 501 for restricting the closed position of the operating portion 491 inwardly of the operating portion 491 is protruded at a position close to the finger insert rings 489 and 490 on the proximal end sides of the scissor constituent members 483 and 484. Even if an excessive closing force is applied to the operating portion 491, the stoppers 500 and 501 abut against it, making it possible to prevent a gap from being provided between tips of the contact surfaces 492a and 493a in the heaters 492 and 493 of the jaws 486 and 487.

Further, while the stoppers 500 and 501 are acting in abutment, a wide range of the full surfaces of the contact surfaces 492a and 493a of the heaters 492 and 493 is closed, and a sufficient closing force of 1 kgf or more is acted to the jaws 486 and 487. Therefore, there is an effect that the patients body tissue grasped between the jaws 486 and 487 is well compressed, improving coagulation.

The user may only grip the operating portion 491 until the stoppers 500 and 501 have been actuated, and thus, there is no need for worrying about adjustment of the closing force. Therefore, there is an effect that operation of the coagulating treatment instrument 481 becomes simpler.

Figure 54A:
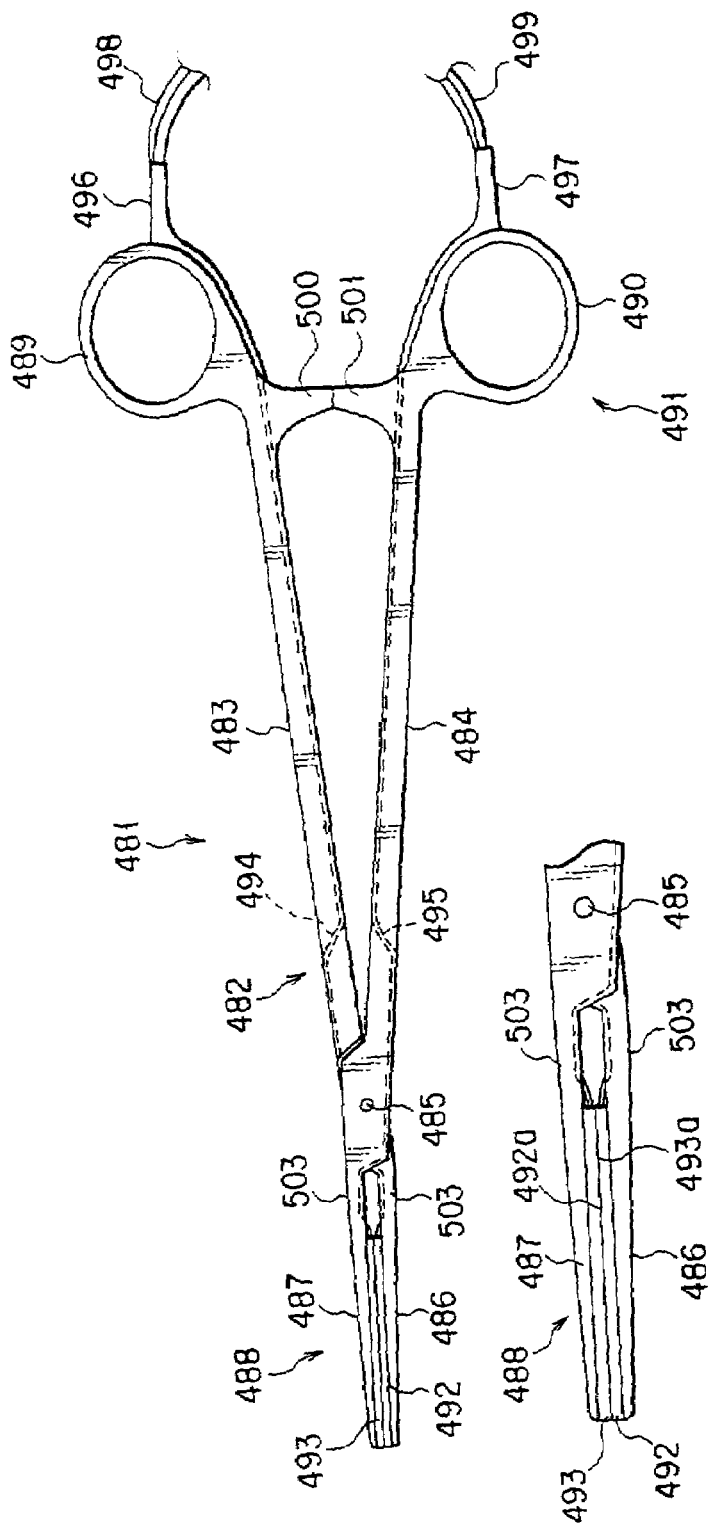
FIG. 54A is a front view showing a state in which the coagulating treatment instrument according to the thirty-eighth embodiment is closed to a position at which the treatment instrument abuts against a stopper, and a closing force is applied to the jaw.
Figure 54B:
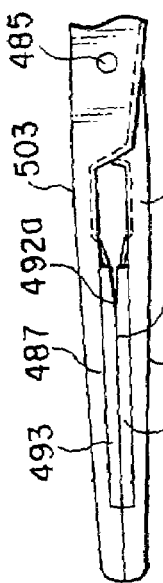
FIG. 54B is an enlarged front view showing the jaw at the tip of the coagulating treatment instrument according to the thirty-eighth embodiment.
Figure 54C:
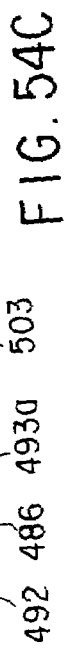
FIG. 54C is a front view of essential portions showing a modified example of the coagulating treatment instrument according to the thirty-eighth embodiment.

FIG. 54C shows a modified example of the coagulating treatment instrument 481 of the thirty-eighth embodiment (refer to FIGS. 53A, 53B, 54A and 54B). In this modified example, the heaters 492 and 493 are disposed intermediately of the jaws 486 and 487, and the contact surfaces 492a and 493a are partially formed by the tip part of the jaws 486 and 487. In this case, an effect similar to the thirty-eighth embodiment can be obtained.

FIGS. 55A to 55F show a thirty-ninth embodiment of the present invention. FIG. 55A shows a schematic structure of a coagulating treatment instrument 511 according to the present embodiment. A main body 512 of the coagulating treatment instrument 511 according to the present embodiment is provided with two scissor constituent members 513 and 514. These scissor constituent members 513 and 514 are placed in a state in which their intermediate portions substantially cross with each other. Further, a fulcrum pin 515 for rotatably linking these scissor constituent members 513 and 514 with each other is arranged at the cross section of the scissor constituent members 513 and 514.

A treatment portion 518 comprising a pair of jaws 516 and 517 capable of being opened and closed, which grasps the patient's body tissue, is arranged at the tip of the treatment instrument main body 512. Further, substantially elliptical finger insert rings 519 and 520 are formed at the proximal ends of the scissor constituent members 513 and 514. A frontal operating portion 521 for operating a pair of jaws 516 and 517 to be opened and closed is formed by the portions of these finger insert rings 519 and 520.

In addition, as shown in FIGS. 55C and 55D, a curve portion 522 gently curved in a substantial arc shape is formed at the treatment portion 518 of the treatment instrument main body 512. Further, at the jaws 516 and 517 of the treatment instrument main body 512, as shown in FIG. 55A, heaters 523 and 524 for coagulating the patient's body tissue is provided on the contact surface side with the patient's body tissue. The heaters 523 and 524 to be used here include a ceramic heater, a PTC heater (a heater formed of a positive temperature coefficient material), a semiconductor heater or the like.

As shown in FIG. 55A, insulation lead wires 525 and 526 are arranged, respectively, at the scissor constituent members 513 and 514. At the tip, the insulation lea wire 525 on one scissor constituent member 513 side is connected to the heater 523 on the jaw 516 side. At the tip, the insulation lead wire 526 on the other scissor constituent member 514 side is connected to the heater 524 on the jaw 517 side.

When power is supplied to each of the heaters 523 and 524, an anode and a cathode are required. Thus, as shown in FIG. 55D, two insulation lead wires 525 and 526 requires a total of four lead wires, i.e., two lead wires 526a and 526b to be connected to the upper heater 524 as shown in FIG. 55D and two lead wires 525a and 525b to be connected to the lower heater 523. These lead wires 526a, 526b, 525a, and 525b are required to be insulated from each other. In the present embodiment, each of these wires is covered with an insulation cover.

One cable connection portion 527 is protruded at the peripheral surface of the finger insert ring 519 on the scissor constituent member 513 side. Similarly, one cable connection portion 528 is protruded at the peripheral surface of the finger insert ring 520 on the scissor constituent member 514 side. At a proximal end, the insulation lead wire 525 is connected to the cable connection portion 527 on the scissor constituent member 513 side, and the insulation lead wire 526 is connected to the cable connection portion 528 on the scissor constituent member 514 side. Further, to these cable connection portions 527 and 528, connector cables 529 and 530 whose one ends are connected to the power supply unit (not shown) are detachably connected at the other ends. From the power supply unit (not shown), power is supplied to the heaters 523 and 524 of the jaws 516 and 517, respectively.

As shown in FIG. 55E, a lead wire storage groove portion 531 is formed at one scissor constituent member 513. Two lead wires 525a and 525b of the insulation lead wire 525 are stored in this lead wire storage groove portion 531. Similarly, as shown in FIG. 55F, a lead wire storage groove portion 532 is formed at the other scissor constituent member 514. Two lead wires 526a and 526b of the insulation lead wire 526 are stored in this lead wire storage portion 532.

A combination of these two lead wires to be stored in the lead wire storage groove portions 531 and 532 is not limited to that of the present embodiment, and these four lead wires may be stored in a single lead wire storage groove portion.

In addition, in order to ensure electrical insulation of each connection portion 533 between the heaters 523, 524 and the insulation lead wires 525, 526, each connection portion 533 may be covered with a rubber seal material or the like. Further, a rubber seal material 534 for fixing the insulation lead wires 525 and 526 may be charged in the lead wire storage groove portions 531 and 532 of the scissor constituent members 513 and 514. Any shape or configuration of the insulation lead wires 525 and 526 may be employed as long as power can be supplied. An elongated thin plate covered to be insulated may be employed without being limited to these lead wires.

With the above structure, the following effect will be obtained. That is, in the present embodiment, the lead wire storage groove portion 531 is formed at one scissor constituent member 513, and two lead wires 525a and 525b of the insulation lead wire 525 are stored at this lead wire storage groove portion 531. Further, a lead wire storage groove portion 532 is formed at the other scissor constituent member 532, and two lead wires 526a and 526b of the insulation lead wire 526 are stored in this lead wire storage groove portion 532. Thus, there is no possibility that the insulation lead wires 525 and 526 are exposed to the scissor constituent members 513 and 514 of the treatment instrument main body 512. Therefore, the insulation lead wires 525 and 526 do not interfere with operation, and operability of the coagulating treatment instrument 511 can be improved.

FIG. 55G shows a modified example of the coagulating treatment instrument 511 according to the thirty-ninth embodiment (refer to FIGS. 55A to 55F). In the modified example, a cover 541 made of an insulation material is provided outside the scissor constituent members 513 and 514 of the treatment instrument main body 512. In this cover 541, insulation lead wires 525 and 526 are stored. In the modified example, an effect similar to that in the thirty-ninth embodiment will be obtained. In the modified example, there is an effect that insulation and covering of the insulation lead wires 525 and 526 are eliminated.

FIGS. 56A to 56F show a fortieth embodiment of the present invention. In the present embodiment, a structure of the coagulating treatment instrument 511 according to the thirty ninth embodiment (refer to FIGS. 55A to 55F) is modified as follows:

That is, in the present embodiment, as shown in FIGS. 56C and 56D, there is provided a connection portion 551, wherein the same electrodes of the insulation lead wires 525 and 526 of the heaters 523 and 524 mounted on the jaws 516 and 517, for example, lead wires 525a and 526a that are cathodes (lead wires 525b and 526b that are anodes) are connected to the jaws 516 and 517, respectively. This connection portion 551 is electrically insulated from the outside with a rubber seal material. In the meantime, the jaws 516 and 517, the scissor constituent members 513 and 514 of the treatment instrument main body 512 and the jaws 516 and 517 are made of a metal such as stainless.

A cable connection portion 552 electrically connected to this scissor constituent member 513 is added to the peripheral surface of the finger insert ring 519 of one constituent element 513. An external connector cable 553 is detachably connected to this cable connection portion 552. In the meantime, the scissor constituent members 513 and 514 of the treatment instrument main body 512 and at least a part of the peripheral surface of the operating portion 521 are covered with an insulation cover.

As shown in FIG. 56E, one insulation lead wire 525b that is an anode is stored in the lead wire storage groove portion 531 of the scissor constituent member 513. Similarly, as shown in FIG. 56F, one insulation lead wire 526b that is an anode is stored in the lead wire storage groove portion 532 of the scissor constituent member 514.

In the meantime, there may be provided a connection portion 551, wherein the lead wire 525b that is an anode and the lead wire 526b are connected to the jaws 516 and 517, respectively. Further, one insulation lead wire 525a that is a cathode may be stored in the lead wire storage groove portion 531 of the scissor constituent member 513, and one insulation lead wire 526a that is an anode may be stored in the lead wire storage groove portion 532 of the scissor constituent member 514.

With the above structure, the following effect will be obtained. That is, one scissor constituent member 513 and the jaw 516 are utilized as a electrically conducting member of an anode or a cathode for supplying power to each of the heaters 523 and 524. Thus, the number of insulation lead wires to be stored in the lead wire storage groove portions 531 and 532 of the scissor constituent members 513 and 514 of the treatment instrument main body 512 can be reduced. Therefore, there is an affect that the scissor constituent members 513 and 514 of the treatment instrument main body 512 can be thinned. In addition, the insulation lead wires themselves can be thickened, and a loss due to an electric resistance can be decreased.

FIGS. 57A to 57F show a forty-first embodiment of the present invention. In the present embodiment, a structure of the coagulating treatment instrument 511 according to the fortieth embodiment (refer to FIGS. 56A to 56F) is modified as follows:

That is, in the present embodiment, there is provided one insulation lead wire 561, wherein insulation lead wires 525$b$ and 526$b$ to be arranged respectively at the scissor constituent members 513 and 514 of the treatment instrument main body 512 according to the present embodiment are provided in common. This insulation lead wire 561 is diverged into two ways near the jaws 516 and 517, and is connected to the same electrodes of the upper and lower heaters 523 and 524, i.e., an anode in the present embodiment.

Further, in the present embodiment, a lead wire storage groove portion 562 is provided at only one scissor constituent member 514 of the two scissor constituent members 513 and 514 of the treatment instrument main body 512. One insulation lead wire 561 is stored in this lead wire storage groove portion 562.

With the above structure, the following effect will be obtained. That is, in the present embodiment, there is provided one insulation lead wire 561, wherein insulation lead wires 525$b$ and 526$b$ to be arranged respectively at the scissor constituent members 513 and 514 of the treatment instrument main body 512 according to the fortieth embodiment are provided in common. This insulation lead wire 561 is connected to the same electrodes of the upper and lower heaters 523 and 524, i.e., an anode in the present embodiment. Further, a lead wire storage groove portion 562 is provided only at one scissor constituent member 514, and one insulation lead wire 561 is stored in this lead wire storage groove portion 562. Thus, power is supplied from a power source to the heaters 523 and 524 through one insulation lead wire 561 and the treatment instrument main body 512. Therefore, there is an effect that the number of insulation lead wires to be arranged at the treatment instrument main body 512 can further be reduced, and a structure can be simplified more significantly.

Further, of course, the present invention is not limited to the above mentioned embodiment, and can be deformed and implemented without departing from the gist of the present invention.

Figure 58:
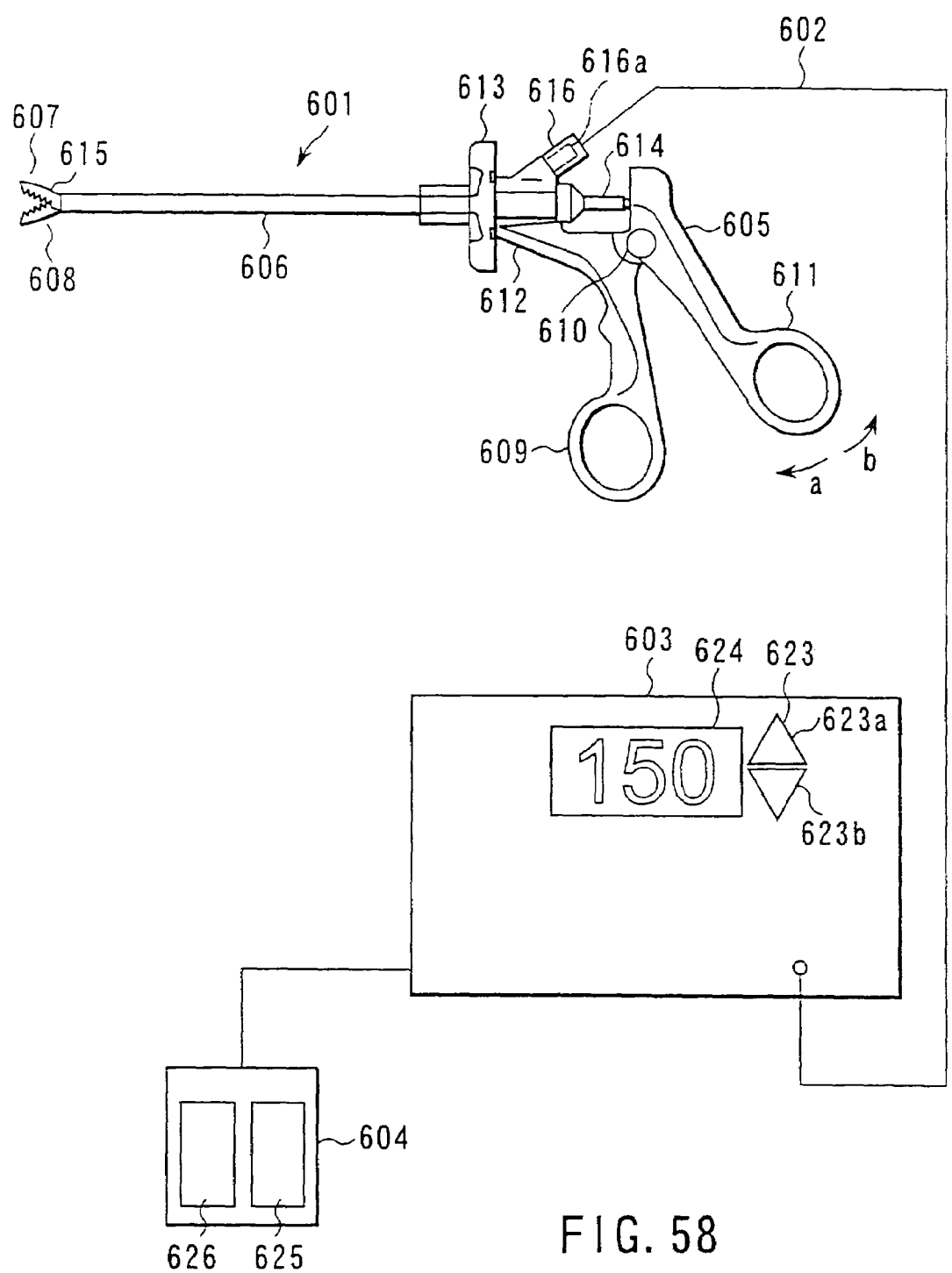
FIG. 58 is a general view of a coagulating/cutting system according to a forty-second embodiment of the invention.
Figure 59:
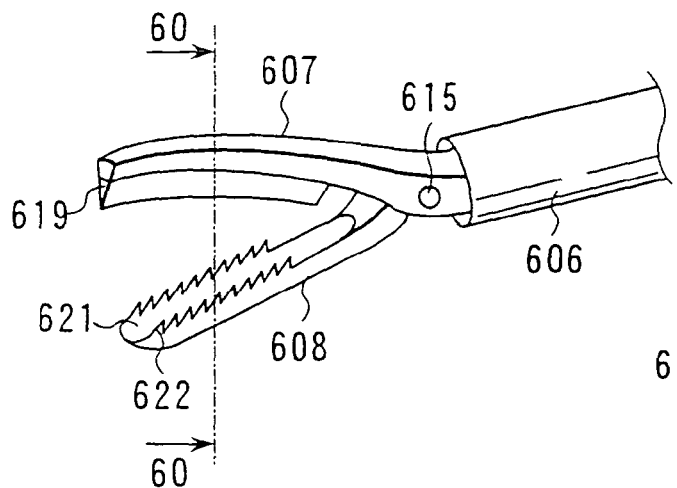
FIG. 59 is a perspective view of a treatment portion according to the forty-second embodiment.
Figure 60:
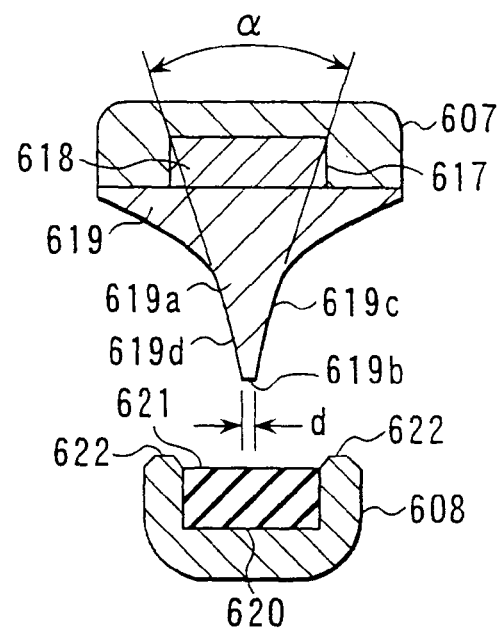
FIG. 60 is a sectional view taken along line 60-60 of FIG. 59.
Figure 61A:
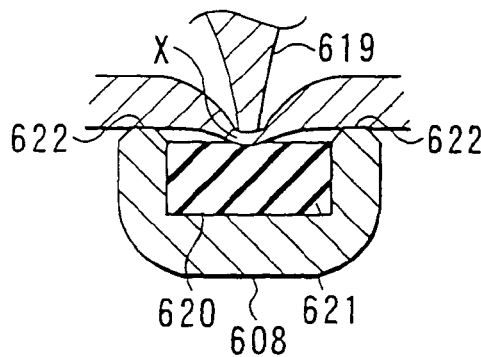
FIG. 61A is a longitudinal sectional view of a principal part of the system, showing a state in which an organism tissue is held stressed under a force of pressure that suits a coagulative treatment, by means of the treatment portion of the forty-second embodiment.
Figure 61B:
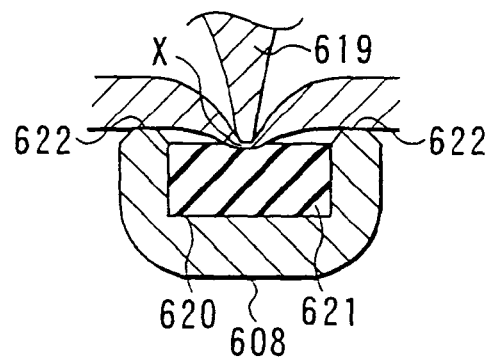
FIG. 61B is a longitudinal sectional view of the principal part, showing a state in which a weakened organism tissue is cut and incised.
Figure 62:
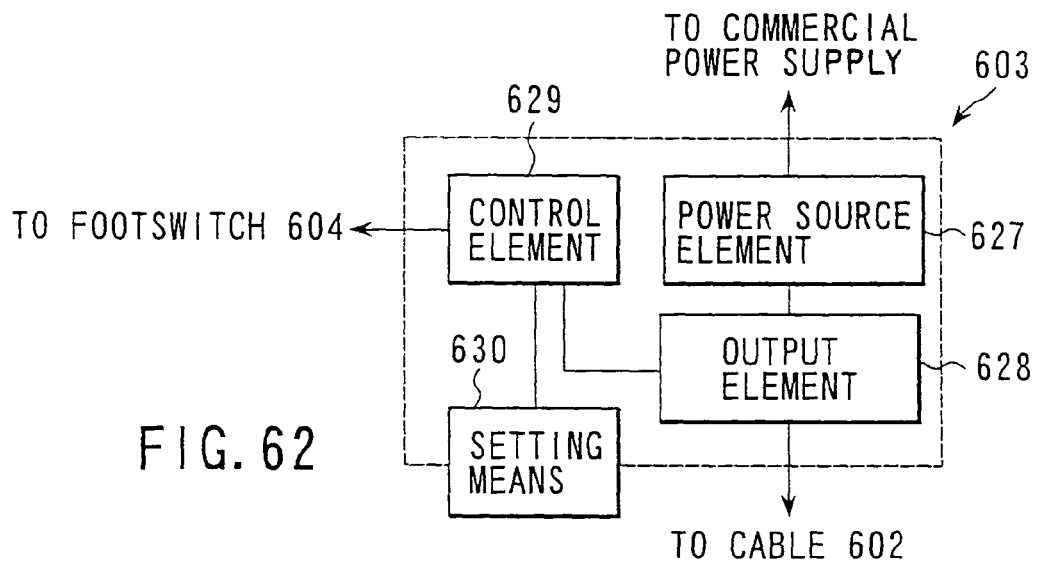
FIG. 62 is a diagram showing an electric circuit of a power source unit according to the forty-second embodiment.

FIGS. 58 to 62 show a forty-second embodiment of the present invention. FIG. 58 is a general view of a coagulating/cutting system according to the present embodiment, FIG. 59 is a perspective view of holding portions of a thermocoagulation cutting forceps, FIG. 60 is a sectional view taken along line 60-60 of FIG. 59, FIGS. 61A and 61B are views for illustrating processes of operation for coagulating and incising a tissue, and FIG. 62 is an electric circuit diagram of a power source unit.

As shown in FIG. 58, a thermocoagulation cutting forceps 601 for uses as a surgical instrument is connected to a power source unit 603 as power supply means by means of a cable 602, and a footswitch 604 for output control is also connected to the unit 603. The forceps 601 is composed of a hand operating portion 605 for use as holding portion drive means, insert portion 606, and a pair of holding portions 607 and 608 as first and second engaging surfaces on the distal end of the insert portion 606.

The hand operating portion 605 is formed of an operating portion body 612, fixed handle 609 integral with the body 612, and a movable handle 611 rockable around a pivot 610. The insert portion 606 is mounted on the operating portion body 612 for rotation around it axis by means of a rotation control portion 613.

The insert portion 606 is formed of a slender pipe, in which a drive shaft 614 is inserted for axial movement. The proximal end portion of the shaft 614 is coupled to the movable handle 611. The first and second holding portions 607 and 608 are provided on the distal end portion of the shaft 614. The holding portions 607 and 608 are swingable around a pivot pin 615. If the movable handle 611 is rocked in the direction of arrow a, the drive shaft 614 retreats to close the holding portions 607 and 608. If the handle 611 is rocked in the direction of arrow b, the shaft 614 advances to open the holding portions 607 and 608.

The operating portion body 612 is provided with a connector junction 616$a$, which is removably connected with a connector 616 of the cable 602. The junction 616$a$ is connected electrically to a heating unit 618 (mentioned later), which is provided on the first holding portion 607 so as to extend along the drive shaft 614.

As shown in FIGS. 59 and 60, the first holding portion 607 is provided with a groove 617 that opens toward the second holding portion 608. The groove 617 extends in the longitudinal direction of the first holding portion 607. A heating unit 618 is stored in the groove 617. A heating plate 619 is bonded to the heating unit 618.

The heating unit 618 is formed of, for example, a molybdenum-film resistance-heating element that is small-sized and enjoys high heating efficiency. As shown in FIG. 60, the heating plate 619 is profiled having a substantially chevron-shaped projection 619$a$. A flat portion 619$b$ with a width d is formed on the distal end of the projection 619$a$, and two flat surfaces 619$c$ and 619$d$ are formed individually on the opposite sides of the flat portion 619$b$ in a manner such that an angle α is formed between them.

In order to prevent an organism tissue from sticking to the outer surface of the heating plate 619 and the respective outer surfaces of the first and second holding portions 607 and 608, these outer surfaces are coated with fluoroplastics, such as Teflon (trademark, Dupont). Recommended values for the width d range from about 0.1 to 0.15 mm. Preferably, moreover, the angle α ranges from about 30 to 90 degrees (angle α may be asymmetric).

The width d is a dimension that covers a Teflon coating on the surface of the heating plate 619 (the Teflon coating is not shown). Preferably, the heating plate 619 should be formed of a material with high thermal conductivity, such as copper, silver, tungsten, etc., and the heating unit 618 may alternatively be a ceramic heater, cartridge heater, PTC heater, etc.

The second holding portion 608 has a wide recess 620 that opens toward the first holding portion 607, and its cross section is U-shaped. A receiving member 621 of a soft material is provided in the recess 620. Available materials for the receiving member 621 include, for example, rubber (silicone rubber, fluororubber, ethylene-propylene rubber, butyl rubber, etc.), gel (silicone-based α gel or the like), and fluoroplastics (e.g., Teflon). Serrated antiskid portions 622 are provided individually on the opposite side edges of the recess 620.

As shown in FIG. 58, moreover, the power source unit 603 is provided with a setting portion 623 capable of setting the heating temperature of the heating unit 618 and a display portion 624. The setting portion 623 is provided with an upper button 623a for raising the set temperature and a lower button 623b for lowering the set temperature. Further, the display portion 624 displays the set heating temperature (e.g., 150° C.) of the heating unit 618. The heating temperature can be set by means of the setting portion 623. The set temperature can be raised and lowered by depressing the upper and lower buttons 623a and 623b, respectively.

The footswitch 604 is provided with first and second pedals 625 and 626. The first pedal 625 is an incision pedal for an output set at a possible incision temperature, for example. The second pedal 626 is a coagulation pedal for an output set at a possible coagulation temperature, for example.

FIG. 62 shows an electric circuit of the power source unit 603. A power source element 627 that is connected to the commercial power supply is connected to the cable 602 through an output element 628. The output element 628 is connected to a control element 629. The control element 629 is connected with setting means 630 for setting the heating temperature and the footswitch 604.

The following is a description of the operation of the forty-second embodiment. In operating the thermocoagulation cutting forceps 601 of the present embodiment, an operator holds the hand operating portion 605 and rocks the movable handle 611 in the direction of arrow b of FIG. 58 with respect to the fixed handle 609. Thereupon, the drive shaft 614 advances to open the first and second holding portions 607 and 608. In this state, the forceps 601 is advanced, and the movable handle 611 is rocked in the direction of arrow a of FIG. 58 in a manner such that a region X of the organism tissue to be coagulated and incised is interposed between the first and second holding portions 607 and 608. Thereupon, the drive shaft 614 retreats to close the holding portions 607 and 608.

Then, the region X of the organism tissue to be coagulated and incised is held stressed under a force of pressure that suits a coagulative treatment, as shown in FIG. 61A. Thus, the organism tissue is compressed between the flat portions 619b, 619c and 619d of the heating plate 619 and the receiving member 621. Owing to the presence of the flat portion 619b, in this state, the distal end of the 619 is not sharp enough to be able to cut the organism tissue. Thus, the organism tissue cannot be incised.

If the heating unit 618 is then supplied with current from the power source unit 603 and heated, the heating plate 619 is heated by transferred heat. Thereupon, a region of the organism tissue in contact with the thin flat portion 619b is coagulated at high pressure, so that evaporation of water from the organism tissue advances. Then, the weakened organism tissue is cut and incised. As this is done, those portions of the receiving member 621 which engage the flat portions 619b, 619c and 619d are delicately deformed, so that a coagulative force for compressing the periphery of the organism tissue to be incised is enhanced.

The organism tissue incised by this deformation is compressed throughout the length between the flat portion 619b and the receiving member 621, so that the heating plate 619 can securely coagulate and incise the tissue throughout its length.

The following is a description of the heating temperature of the heating unit 618. It is known that if the heating temperature is set at 200° C., water evaporates from the organism tissue relatively drastically, so that incision can be carried out rapidly. Since the heating time need not be long, the organism tissue cannot be coagulated much and looks as if it were cut by means of a sharp edge tool. Thus, the arrangement of the present embodiment is suited for the incision of tissues that include very fine blood vessels or rarely include ones.

If the heating temperature is then adjusted to 180° C., water evaporates more slowly than in the case where the heating temperature is set at 200° C. Since the heating time is a little longer in this case, the organism tissue is fully coagulated, the coagulative force can be enhanced, and incision can be carried out. Thus, tissues including blood vessels can be incised without bleeding.

If the heating time is set at 160° C., moreover, evaporation of water from the organism tissue is insufficient for incision. In this state, therefore, the organism tissue can be only coagulated without being incised.

Since the thin heating plate compresses the organism tissue according to the forty-second embodiment, it produces a great coagulative force. The organism tissue can be incised the moment it is coagulated. Further, the organism tissue is never cut in an unheated state. When the holding portions are closed, moreover, the receiving member is deformed to compress the tissue uniformly throughout the length, so that the tissue can be coagulated and incised securely. The coagulative force increases as the receiving member is delicately deformed. Furthermore, thin-film resistance-heating elements or other heating units that are susceptible to external environment enjoy higher durability, since they are embedded in holding portions.

The following is a description of another example of the coagulating/cutting operation. The operator steps on the first or second pedal 625 or 626 in a manner such that the region X of the organism tissue to be coagulated and incised is held stressed under a force of pressure that suits the coagulative treatment, as shown in FIG. 61A. The case where the first pedal 625 is worked will be described first. The thermocoagulation cutting forceps 601 is supplied with current from the power source unit 603 through the cable 602. If the first pedal 625 is worked without regard to the setup of the setting means 630, the control element 629 controls the heating unit 618 of the first holding portion 607 so that it is heated at its maximum temperature, whereupon current is supplied.

Since the heating unit 618 is heated at the maximum temperature, water quickly evaporates from the organism tissue, so that incision can be carried out rapidly. In consequence, the incisive force becomes greater. Since the heating time is short, however, the organism tissue cannot be coagulated much and looks as if it were cut by means of a sharp edge tool. Thus, the arrangement of the present embodiment is suited for the incision of tissues that include very fine blood vessels or rarely include ones.

The following is a description of the case where the second pedal 626 is worked. If the second pedal 626 is worked, the control element 629 controls the heating unit 618 so that it is heated at a temperature set by means of the setting means 630, whereupon current is supplied. Let it be supposed that the operator sets a temperature a little lower than the maximum temperature of the heating unit 618 as a set temperature. Since the heating unit 618 is heated at a temperature a little lower than the maximum temperature, incision is slower than in the case where the first pedal 625 is worked. Thus, the heating time lengthens, so that the coagulative force can be enhanced. In this case also, the organism tissue can be incised the moment it is coagulated, so that tissues including blood vessels can be incised without bleeding.

If the set temperature is then further lowered, evaporation of water from the organism tissue is insufficient for incision. In this state, therefore, the organism tissue can be only coagulated without being incised.

In this manner, the one thermocoagulation cutting forceps 601 can be freely alternatively used for any of three operation modes, including incision-only, continuous coagulation/incision, and coagulation-only. Thus, it can provide expediency of a level that can be attained with use of a plurality of medical instruments. This arrangement can produce a great effect in an endoscopic surgical operation that requires troublesome intra-operative replacement of forceps, in particular.

In the operation of the footswitch 604 according to the embodiment described above, the operator can previously omit the setup of the set temperature for an incisive treatment that is frequently used in surgical operations for digestive organs or the like.

The operation of the footswitch 604 is not limited to the embodiment described above, and may be carried out in the following manner.

The first pedal 625 is heated at a set temperature.

The second pedal 626 is always heated at its minimum temperature (lower limit of the set temperature).

Thus, if the second pedal 626 is worked, only coagulation can be carried out without incision, so that the setup can be omitted for surgical operations that involve much bleeding or the like. It is to be understood that the operator may be enabled to select one of the above-described operation patterns.

According to the forty-second embodiment, moreover, the first or second pedal is used for the output at the set temperature set by means of the setting means 630. Alternatively, however, the setting means 630 may be given an additional function to set the maximum or minimum temperature or provided with two setting means for setting the set temperature and setting the maximum or minimum temperature.

Further, the setting means 630 may be formed of various means including input means, such as various switches, keyboard, mouse, etc., memories stored with set values, and circuits with the set values.

Figure 63:
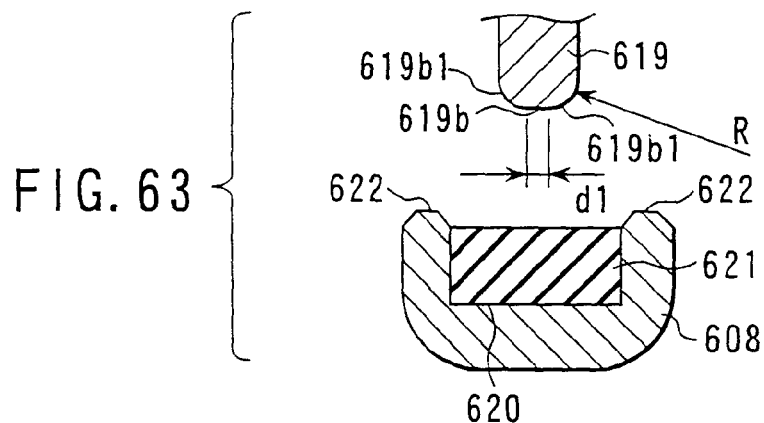
FIG. 63 is a sectional view of holding portions of a thermocoagulation cutting forceps according to a forty-third embodiment of the invention.

FIG. 63 shows a forty-third embodiment. Like reference numerals refer to like components of the present embodiment and the forty-second embodiment (see FIGS. 58 to 62), and a description of those components is omitted. In the present embodiment, a flat portion 619*b* with a width d1 is formed on the distal end portion of a heating plate 619. Each corner portion of the flat portion 619*b* is cut into a smooth arcuate shape, thus forming a chamfer portion 619*b*1. Recommended values for the width d1 range from about 0.1 to 0.15 mm (dimensions covering a resin coating of fluoroplastics, such as Teflon).

In the heating plate 619 of the present embodiment, compared with that of the forty-second embodiment, the presence of the chamfer portion 619*b*1 results in an increased area of contact with the organism tissue and enhanced coagulative force (and correspondingly reduced incisive force).

Figure 64:
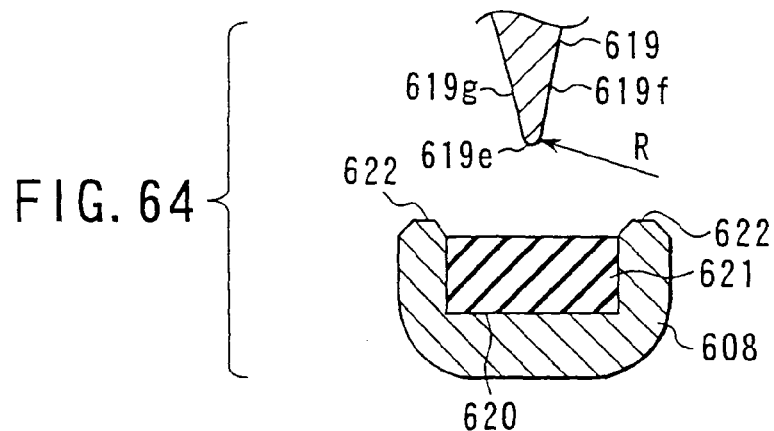
FIG. 64 is a sectional view of holding portions of a thermocoagulation cutting forceps according to a forty-fourth embodiment of the invention.

FIG. 64 shows a forty-fourth embodiment. Like reference numerals refer to like components of the present embodiment and the forty-second embodiment (see FIGS. 58 to 62), and a description of those components is omitted. In the present embodiment, a distal end portion 619*e* of a heating plate 619 is in the form of a circular arc with a radius R, and flat portions 619*f* and 619*g* are formed individually on the opposite sides of the heating plate 619. Recommended values for the radius R range from about 0.05 to 0.15 mm (dimensions covering a Teflon coating).

According to the present embodiment, compared with the forty-second embodiment, the distal end portion 619*e* of the heating plate 619 is smoother as a whole and has no shape angle portions, so that it can be reliably coated with Teflon.

Figure 65:
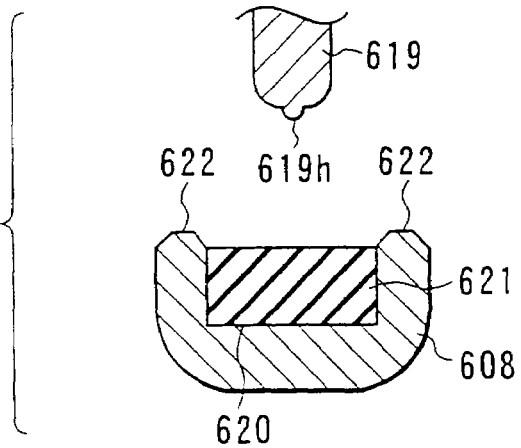
FIG. 65 is a sectional view of holding portions of a thermocoagulation cutting forceps according to a forty-fifth embodiment of the invention.

FIG. 65 shows a forty-fifth embodiment. Like reference numerals refer to like components of the present embodiment and the forty-second embodiment (see FIGS. 58 to 62), and a description of those components is omitted. In the present embodiment, an arcuate protrusion 619*h* is formed on the distal end portion of a heating plate 619. The protrusion 619*h* is not limited to the arcuate shape, and may alternatively be rectangular or triangular.

According to the present embodiment, the protrusion 619*h* on the distal end portion of the heating plate 619 is used for incision, so that the incisive force is greater than in the case of the forty-fourth embodiment.

Figure 66:
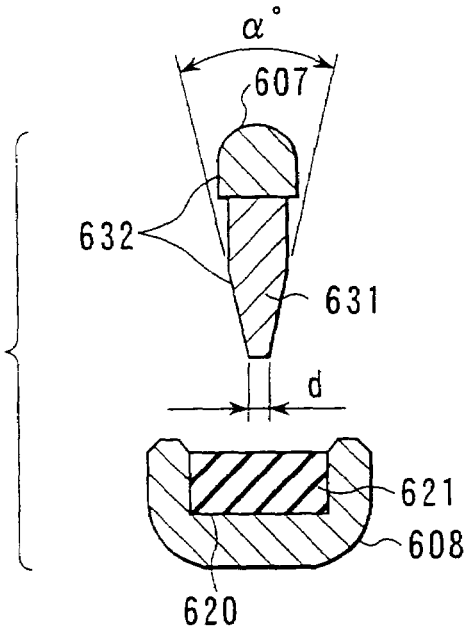
FIG. 66 is a sectional view of holding portions of a thermocoagulation cutting forceps according to a forty-sixth embodiment of the invention.

FIG. 66 shows a forty-sixth embodiment. Like reference numerals refer to like components of the present embodiment and the forty-second embodiment (see FIGS. 58 to 62), and a description of those components is omitted. In the present embodiment, a ceramic heater 631 is provided directly in place the heating plate 619.

More specifically, the ceramic heater 631 is fixed directly to the lower part of a first holding portion 607. Although the heater 631 has the same cross profile as that of the heating plate 619 of the forty-second embodiment, it may have the same cross profile as those of the heating plates 619 of the forty-third to forty-fifth embodiments. A Teflon coating 632 covers the respective outer surfaces of the ceramic heater 631 and the first holding portion 607. Since the heater 631 is a relatively strong simple, it can be used in this manner and its construction can be simplified.

Figure 67:
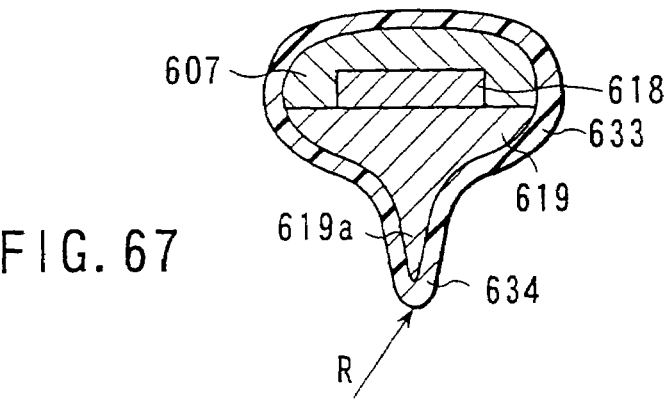

FIG. 67 shows a forty-seventh embodiment. Like reference numerals refer to like components of the present embodiment and the forty-second embodiment (see FIGS. 58 to 62), and a description of those components is omitted. In the present embodiment, a Teflon coating 633 covers the outer surface of a heating plate 619 that has a sharp projection 619*a*.

Although the projection 619*a* on the distal end of the heating plate 619 according to the present embodiment is very sharp, the Teflon coating 633 can form a thin straight portion and a smooth arcuate portion 634 at the distal end of the plate 619, thus producing the same effect of the forty-second embodiment.

The shape of the heating plate 619 (including the ceramic heater 631) is not limited to the embodiments described above, and may be changed as required. The respective cross profiles of the heating plate and the ceramic heater need not be uniform throughout the length, and may be varied partially. For example, the remote-side portion of the heating plate 619 may be sharpened so that it can serve as a portion for incision only. In this case, the hand-side portion of the plate 619 is given the shape according to the foregoing embodiment so that it can serve for coagulation and incision.

FIG. 68A shows a forty-eighth embodiment. Like reference numerals refer to like components of the present embodiment and the forty-second embodiment (see FIGS. 58 to 62), and a description of those components is omitted. The present embodiment is based on a modification of the second holding portion 608. A groove portion 621*a* having an arcuate cross section is formed on the upper surface of a receiving member 621, substantially covering the overall length of the member 621. The receiving member 621 is formed of the material described in connection with the forty-second embodiment.

The groove portion 621*a* may be replaced with a rectangular groove portion 621*b* according to a modification shown in FIG. 68B or a triangular groove portion 621*c* according to a modification shown in FIG. 68C.

The coagulative and incisive forces can be improved as the organism tissue is caught between the heating portion (heating plate, ceramic heater, etc.) of the first holding portion 607 and the groove portion 621*a*.

FIG. 69 shows a forty-ninth embodiment. Like reference numerals refer to like components of the present embodiment and the forty-second embodiment (see FIGS. 58 to 62), and a description of those components is omitted. In the present embodiment, a Teflon coating 633 covers a recess 620 of a second holding portion 608. According to the present embodiment, the system can be easily manufactured at low cost.

FIGS. 70A and 70B show a fiftieth embodiment. Like reference numerals refer to like components of the present embodiment and the forty-second embodiment (see FIGS. 58 to 62), and a description of those components is omitted. In the present embodiment, a receiving member 635 of a synthetic resin is pivotally supported in a recess 620 of a second holding portion 608 by means of a pivot pin 636 so that it can slightly rock around the pin 636. Available synthetic resin materials for the receiving member 635 include, for example, fluoroplastics (e.g., Teflon), PEEK, polyimide, PPS, etc.

According to the present embodiment, the receiving member 635 rocks around the pivot pin 636 following the action of the second holding portion 608 as a first holding portion 607 and the second holding portion 608 are closed. Accordingly, a heating plate 619 and the receiving member 635 come intimately into contact with each other without a gap, so that the organism tissue can be uniformly compressed and securely coagulated and incised.

FIGS. 71A, 71B and 72 show a fifty-first embodiment, which is based on modifications of the display portion 624 of the power source unit 603 according to the forty-second embodiment (see FIGS. 58 to 62). In the present embodiment, a display portion 641 for displaying the temperature level is provided in place of the display portion 624 of the forty-second embodiment that displays the heating temperature. FIG. 71A shows a plurality of bars 641*a* of different heights that indicate the temperature level (level 3 is illustrated as an example).

FIG. 71B shows a display portion 642 that indicates the temperature level by a figure (for level 3 as an example). FIG. 72 shows the relation between the set level and the heating temperature. In this case, levels 5 and 1 correspond to T5 (maximum temperature) and T1 (minimum temperature), respectively.

As shown in FIG. 72, the relation between the set level and the heating temperature T is nonlinear. In the range near the maximum temperature T5, in particular, the change of the temperature T relative to the change of the set level is slower. This is based on the fact that even a small temperature difference near the maximum temperature T5 causes a difference in the way the region of the organism tissue to be coagulated and incised is cut, and that the region of the tissue to be coagulated and incised can be cut without any substantial difference at somewhat lower temperatures.

Thus, the nonlinear relation is established in a manner such that the current supply and heating are effected in a desired coagulating/cutting state that is selected by changing the level by means of the setting portion 623 of the power source unit 603. If the level is changed, therefore, the incisive force changes only slowly, ensuring user-friendliness.

FIG. 73 shows a fifty-second embodiment. In the present embodiment, a fixed handle 609 of a thermocoagulation cutting forceps 601 is provided with a hand switch unit 643 for output control in place of the footswitch 604 of the forty-second embodiment (see FIGS. 58 to 62). The hand switch unit 643 is provided with first and second switches 643*a* and 643*b* that correspond to the first and second pedals 625 and 626 of the footswitch 604, respectively. The first switch 643*a* is used for the output at a set temperature for incision, and the second switch 643*b* for the output at a set temperature for coagulation, for example.

According to the present embodiment, the output of the thermocoagulation cutting forceps 601 can be controlled by only manipulating the hand switch 643 of the fixed handle 609 of the forceps 601 with fingers, so that the user-friendliness is higher than in the case where the footswitch 604 is used.

Figure 74:
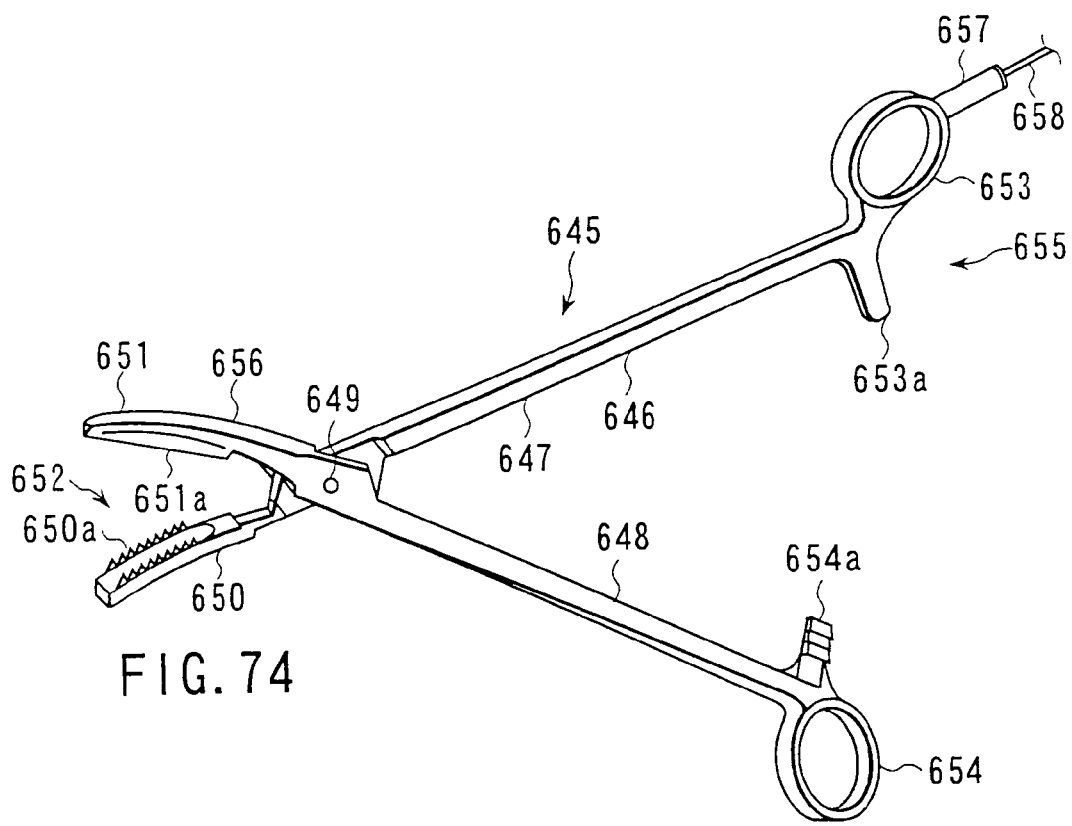

FIG. 74 is a perspective view of a scissors-type thermocoagulation cutting forceps 645 according to a fifty-third embodiment. A body 646 of the forceps 645 of the present embodiment is provided with two scissors members 647 and 648. The members 647 and 648 are lapped crossing each other substantially in the middle. Further, a pivot pin 649 for rockably connecting the scissors members 647 and 648 is provided on the intersection of the members 647 and 648.

A treatment portion 652 is formed on the distal end portion of the body 646. It is provided with a pair of jaws 650 and 651 that constitute swingable holding portions for holding the organism tissue. Further, substantially elliptic finger rings 653 and 654, having ratchets 653*a* and 654*a*, respectively, are formed on the proximal end portions of the scissors members 647 and 648, respectively. These finger rings 653 and 654 form a hand operating portion 655 for opening and closing the jaws 650 and 651.

The treatment portion 652 of the body 646 is formed having a curved portion 656 that is curved gently in the shape of a substantially circular arc. Further, a serrated antiskid portion 650*a* is provided on the inner surface of the one jaw 650, while a thin heating plate 651*a*, having a heating unit for coagulating the organism tissue embedded therein, is formed on the inner surface of the other jaw 650, that is, on the side in contact with the organism tissue. The heating plate 651*a* is connected to a connector 657 by means of the scissors member 647. The connector 657 is connected with a cable 658 that connects with a power source unit (not shown).

The following is a description of the operation of the thermocoagulation cutting forceps 645 constructed in this manner. First, the treatment portion 652 at the distal end portion of the body 646 is inserted in a closed state into the organism tissue that includes a to-be-treated region such as a blood vessel (not shown). Thereafter, the jaws 650 and 651 are opened so that the blood vessel or the like is separated from other organism tissues and exposed.

Subsequently, the separated blood vessel or the like is held stressed between the jaws 650 and 651 under a relatively small appropriate force of pressure that suits the coagulative treatment. If the power source unit (not shown) is worked in this state, current is supplied to the heating unit of the heating plate 651*a* of the jaw 651 through the cable 658. The heating unit is heated by electrical resistance during the power supply, whereupon the blood vessel or other organism tissue to be treated, in contact with the surface of the heating plate 651a, is coagulated and incised.

According to the present embodiment, as in the case of the forty-second embodiment, the organism tissue can be satisfactorily incised with a small grip force of the jaws 650 and 651 that are substantially in linear contact with the tissue. Thus, there may be provided a thermocoagulation cutting forceps that can efficiently coagulate and incise the organism tissue in a series of operations.

It is to be understood that the heating unit may alternatively be a thin-film resistance-heating element, PTC heater, cartridge heater, or ceramic heater.

FIGS. 75 and 76 show a fifty-fourth embodiment. FIG. 75 is a perspective view of a scissors-type forceps 661 for use as a medical instrument. In the present embodiment, a body 662 of the forceps 661 is provided with two scissors members 663a and 663b. The members 663a and 663b are lapped crossing each other substantially in the middle. Further, a pivot 665 for rockably connecting the scissors members 663a and 663b is provided on the intersection of the members 663a and 663b.

A pair of swing elements 666 and 667 are provided on the distal end side of the forceps body 662 with respect to the pivot 665. The swing elements 666 and 667 are formed having holding portions 668a and 668b, respectively, which are curved gently in the shape of a substantially circular arc each.

As in the forty-second embodiment (see FIGS. 58 to 62), a heating unit 618 is located in each of respective holding portions 668a and 668b of the swing elements 666 and 667. When the heating units 618 are energized and heated, their heat is transferred to the surface side of the holding portions 668a and 668b through heating plates 619, so that the organism tissue held between the holding portions 668a and 668b of the swing elements 666 and 667 can be coagulated.

As shown in FIG. 76, a cutting edge portion 669 for incising the organism tissue protrudes from the one holding portion 668b of the scissors-type forceps 661 toward the other holding portion 668a. The edge portion 669 is located substantially in the center of the-holding portion 668b and extends in the longitudinal direction of the holding portion 668b.

The following is a description of the operation of the present embodiment. In using the forceps 661 to treat a blood vessel or other affected region that are intimately in contact with an organism tissue such as an internal organ, as in the case of the forty-second embodiment, the blood vessel is held between the holding portions 668a and 668b after it is separated from the organism tissue. As this is done, the blood vessel is stressed between the holding portions 668a and 668b under a relatively small force of pressure such that the edge portion 669 on the holding portion 668b cannot cut off the blood vessel.

If the heating units 618 are energized and heated in this state, their heat is transferred through the heating plates 619 to the blood vessel that is held between the holding portions 668a and 668b, whereupon the lumen of the blood vessel is coagulated. If a hand operating portion 664 is held tight to move the holding portions 668a and 668b further toward each other, the top of the edge portion 669 of the holding portion 668b is pressed hard against the holding portion 668a. In this manner, the coagulated portion of the blood vessel can be incised by means of the edge portion 669 of the holding portion 668b.

According to the present embodiment, the lumen of the blood vessel is coagulated as the heating units 618 are energized and heated with the blood vessel stressed under a relatively small force of pressure such that the edge portion 669 of the holding portion 668b cannot cut it off when it is held between the holding portions 668a and 668b of the scissors-type forceps 661. Further, the coagulated portion of the blood vessel can be easily incised by means of the edge portion 669 of the holding portion 668b in a manner such that the hand operating portion 664 is held tight to press the top of the edge portion 669 hard against the holding portion 668a.

Thus, according to the present embodiment, as in the case of the forty-second embodiment, the organism tissue can be coagulated and incised with use of the one scissors-type forceps 661. It is unnecessary, therefore, to replace separate medical instruments for individual treatments, so that the user-friendliness is improved and costs are lowered.

FIGS. 77A and 77B show a fifty-fifth embodiment. Like reference numerals refer to like components of the present embodiment and the forty-second embodiment (see FIGS. 58 to 62), and a description of those components is omitted. In the present embodiment, as shown in FIG. 77A, a receiving member 671 of a soft material is located in a recess 620 of a second holding portion 608. A corrugated antiskid portion 672 for organism tissue is formed on a holding surface of the receiving member 671.

When a first holding portion 607 and the second holding portion 608 are closed tight to coagulate and incise the organism tissue, as shown in FIG. 77B, the corrugated portion 672 of the receiving member 671 can be elastically deformed into a substantially flat shape, thereby preventing the organism tissue from slipping off.

FIGS. 78A and 78B show a fifty-sixth embodiment. Like reference numerals refer to like components of the present embodiment and the forty-second embodiment (see FIGS. 58 to 62), and a description of those components is omitted. In the present embodiment, as shown in FIG. 78A, a receiving member 681 of a soft material is located in a recess 620 of a second holding portion 608. An arcuate portion 682 with a wide radius of curvature is formed on a holding surface of the receiving member 681.

FIG. 78A shows a state in which a first holding portion 607 and the second holding portion 608 are closed softly. In coagulating and incising the organism tissue, the first and second holding portions 607 and 608 in this state are closed tight. Thus, the arcuate portion 682 of the receiving member 681 can be elastically deformed into a substantially flat shape by means of the first holding portion 607, so that the organism tissue can be held securely.

FIGS. 79A and 79B show a fifty-seventh embodiment. Like reference numerals refer to like components of the present embodiment and the forty-second embodiment (see FIGS. 58 to 62), and a description of those components is omitted. In the present embodiment, as shown in FIG. 79A, a receiving member 691 of a soft material is located in a recess 620 of a second holding portion 608. A protrusion 692 is formed on that region of a holding surface of the receiving member 691 which engages a heating plate 619 of a first holding portion 607. As shown in FIG. 79B, moreover, the protrusion 692 may be chevron-shaped.

The protrusion 692 thus formed on the receiving member 691 serves to facilitate incision of the organism tissue. Further, the protrusion 692 may be designed so that it can be elastically deformed into a substantially flat shape when the first and second holding portions 607 and 608 are closed tight to coagulate and incise the organism tissue.

FIGS. 80A and 80B show a fifty-eighth embodiment. Like reference numerals refer to like components of the present embodiment and the forty-second embodiment (see FIGS. 58 to 62), and a description of those components is omitted. In the present embodiment, as shown in FIG. 80A, a receiving member 701 of a soft material is located in a recess 620 of a second holding portion 608. A concave surface 702 is formed in that region of a holding surface of the receiving member 701 which engages a heating plate 619 of a first holding portion 607. As shown in FIG. 80B, moreover, the concave surface 702 may be formed only in a part of the holding surface of the receiving member 701.

The concave surface 702 thus formed in the holding surface of the receiving member 701 is an effective measure for the case where the organism tissue to be held is slippery cannot be seized with ease, owing to its shape or properties. The concave surface 702 may be designed so that it can be elastically deformed into a substantially flat shape when the first and second holding portions 607 and 608 are closed tight to coagulate and incise the organism tissue.

FIGS. 81 to 86 collectively show a fifty-ninth embodiment of the present invention, wherein FIG. 81 is an entire structural view of a surgical instrument, FIG. 82 is a side view of the surgical instrument, FIG. 83 is a perspective view of the holding portion, FIG. 84 is a cross sectional along the line A-A shown in FIG. 83, FIG. 85 is an electrical circuit diagram of the power source apparatus, and FIG. 86 is a graph.

As shown in FIG. 81, a thermocoagulation cutting forceps 801 constituting a surgical instrument is connected to a power source apparatus 803 via a cable 802. A foot switch 804 is connected to the power source apparatus 803.

As shown in FIGS. 82 to 84, the thermocoagulation cutting forceps 801 comprises a slender inserting portion 806, a manual operating portion 805 arranged at a proximal end portion of the inserting portion 806, and a treating portion 807 mounted at the distal end portion of the inserting portion 806. A pair of first and second holding portions 808A and 808B are arranged in the treating portion 807.

An operating body 812 and a stationary handle 809 are integrally mounted to the manual operating portion 805. Further, a movable handle 811 is swingably mounted to the operating body 812 such that the handle 811 is swingable about a pivotal shaft 810 providing the fulcrum.

The inserting portion 806 is joined to the operating body 812 such that the inserting portion 806 is rotatable about its own axis. A rotary operating portion 813 is arranged in the operating body 812. The proximal end portion of the inserting portion 806 is joined to the rotary operating portion 813. It should be noted that the rotary operating portion 813 permits the inserting portion 806 to be rotated relative to the operating body 812.

The inserting portion 806 is formed of a pipe having a small diameter, and a driving shaft 814 is movably inserted into the inserting portion 806. The proximal end portion of the driving shaft 814 is joined to the movable handle 811, and the first and second holding portions 808A, 808B are arranged in the distal end portion of the driving shaft 814. It is possible to open the first and second holding portions 808A, 808B about a pivotal pin 815 providing a fulcrum. If the movable handle 811 is rotated in a direction denoted by an arrow a in FIG. 82, the driving shaft 814 is moved backward so as to close the first and second holding portions 808A, 808B. Further, if the movable handle 811 is moved in a direction denoted an arrow b shown in FIG. 82, the driving shaft 814 is moved forward so as to open the first and second holding portions 808A and 808B.

A connector connecting portion 816a is mounted to project upward from the operating body 812, as shown in FIG. 82. An electrical contact 816b is mounted to the connector connecting portion 816a. The electrical contact 816b is electrically connected to a heating element 823 of a ceramic heater 822, which will be described hereinlater, arranged in the second holding portion 808B along the driving shaft 814. Further, a connector 816 of a cable 802 is detachably connected to the connector connecting portion 816a.

The first and second holding portions 808A and 808B will now be described. As shown in FIG. 84, the first holding portion 808A is wide and is formed in the shape of a letter "U" in its cross section. A concave portion 817 open in its lower portion is formed in the first holding portion 808A. Further, saw tooth-like slip-preventing portions 818 are formed in the edge portions on the lower side of the first holding portion 808A in a manner to have the concave portion 817 sandwiched therebetween. Incidentally, a heat insulating member 819 formed of a flexible material such as Teflon is buried in the concave portion 817.

A heater holding portion 820 having a width smaller than that of the concave portion 817 and having a rectangular cross section is arranged in the second holding portion 808B. An arcuate groove 821 is formed on the upper surface of the heater holding portion 820. Further, the columnar ceramic heater 822 acting as a heat generating portion is fixed to the arcuate groove 821. The ceramic heater 822 is formed by burying a heating element 823, which is a heat generating resistor, within the ceramic material, which is an insulating material. Further, a Teflon coating is applied to the outer surfaces of the first and second holding portions 808A and 808B so as to prevent the scorch of the living tissues.

FIG. 85 shows the electric circuit of the power source apparatus 803. As shown in the drawing, a power source circuit 824 connected to a commercial power source is connected to the cable 802 via an output circuit 825. The output circuit 825 is connected to a control circuit 826, which is connected to the foot switch 804. Further, the control circuit 826 is connected to a setting means 827 for setting the temperature, time, etc.

FIG. 86 is a graph showing the change with time in temperature during the cutting time, the coagulation time and the coagulating cutting time. In the graph of FIG. 86, the time t (seconds) is plotted on the abscissa, with the temperature T (° C.) being plotted on the ordinate. It is possible for the setting means 827 to set selectively the temperature elevation in the cutting step in which the temperature is rapidly elevated to temperature T1 as denoted by curve f1, the temperature elevation in the coagulation step in which the temperature is slowly elevated to temperature T2 and temperature T2 is maintained for several seconds as denoted by curve f2, and the temperature elevation in the coagulation cutting step in which the temperature is slowly elevated to temperature T2 and, then, rapidly elevated to temperature T1 as denoted by curve f3.

The operation for coagulating-cutting the coagulation cutting portion of the living tissue by the thermocoagulation cutting forceps of the construction described above will now be described.

If the operator holds the manual operating portion 805 and rotates the movable handle 811 relative to the stationary handle 809 in a direction denoted by an arrow b in FIG. 82, the driving shaft 814 is moved forward so as to open the first and second holding portions 808A and 808B. If the thermocoagulation cutting forceps 801 is moved forward under this condition, the coagulation cutting portion of the living tissue is held between the first and second holding portions 808A and 808B. If the movable handle 811 is rotated under this condition in the direction denoted by the arrow "a" in FIG. 82, the driving shaft 814 is moved backward so as to close the first and second holding portions 808A and 808B.

Then, the coagulation cutting portion of the living tissue is held under a compressed state with a relatively small appropriate compressing force adapted for the coagulation treatment. If the foot switch 804 is turned on under this state, an electric current is supplied from the power source apparatus 803 to the thermocoagulation cutting forceps 801 through the cable 802. As a result, the current set by the setting means 827 is supplied to the heating element 823 arranged within the ceramic heater 822 of the second holding portion 808B, with the result that heat is generated from the heating element 823.

Since the temperature is gradually elevated to temperature T2 by the heat generation from the heating element 823 and temperature T2 maintained for several seconds as denoted by curve f2 in FIG. 86, the coagulation cutting portion of the living tissue is coagulated. In this case, the heat of the ceramic heater 822 is not released to the first holding portion 808A because that region of the first holding portion 808A which is in contact with the living tissue is formed of the heat insulating material 819.

Then, the electric current set by the setting means 827 is supplied to the heating element 823 at time t4. As a result, the temperature is rapidly elevated to temperature T1 as denoted by curve f3 in FIG. 86. At the same time, if the movable handle 811 is rotated in the direction denoted by the arrow "a", the driving shaft 814 is moved backward so as to further close the first and second holding portions 808A and 808B, thereby making it possible to cut the coagulation cutting portion of the living tissue.

It should be noted that the contact surface of the second holding portion 808B with the living tissue is formed of the columnar ceramic heater 822, making it possible for the second holding portion 808B to be brought into a linear contact with the living tissue, leading to an excellent cutting performance. As a result, the living tissue can be cut with a small holding force between the first and second holding portions 808A and 808B. It follows that the present invention provides a thermocoagulation cutting forceps, which permits the operations ranging between the coagulation and the cutting to be performed by a series of continuous operations and which is excellent in the cutting performance of the living tissue.

FIG. 87A shows a sixtieth embodiment of the present invention. This embodiment is substantially equal to the fifty-ninth embodiment shown in FIGS. 81 to 86, except that, in the sixtieth embodiment, the treatment portion 807 of the thermocoagulation cutting forceps 801 is constructed as described in the following. Incidentally, the constructions of the embodiment shown in FIG. 87A, which are the same as those of the fifty-ninth embodiment, are denoted by the same reference numerals.

In the embodiment shown in FIG. 87A, a columnar ceramic heater 831 is arranged in the concave portion 817 of the first holding portion 808A. A heating element 832 formed of a heat generating resistor is buried in the ceramic heater 831. In this embodiment, heat is generated from both the heater 832 within the first holding portion 808A and the heater 823 within the second holding portion 808B.

FIG. 87B shows a first modification of the treatment portion 807 in the surgical instrument according to the sixtieth embodiment of the present invention, which is shown in FIG. 87A. In this modification, a rectangular ceramic heater 833 is arranged within the concave portion 817 of the first holding portion 808A. A heating element 834 formed of a heat generating resistor is buried in the ceramic heater 833. It follows that the heat energy is generated from both the heating element 834 within the first holding portion 808A and the heating element 823 within the second holding portion 808B.

FIG. 87C shows a second modification of the treatment portion 807 in the surgical instrument according to the sixtieth embodiment of the present invention, which is shown in FIG. 87A. In this modification, a rectangular heater holding portion 835 having a small width is mounted to the first holding portion 808A. An arcuate groove 836 is formed in the heater holding portion 835. Also, a ceramic heater 837 is arranged in the arcuate groove 836. A heating element 838 formed of a heat generating resistor is buried in the ceramic heater 837. It follows that the heat energy is generated from both the heating element 838 within the first holding portion 808a and the heating element 823 within the second holding portion 808B.

FIG. 87D shows a third modification of the treatment portion 807 in the surgical instrument according to the sixtieth embodiment of the present invention, which is shown in FIG. 87A. In this modification, a rectangular ceramic heater 839 having a small width is mounted to the heater holding portion 820 of the second holding portion 808B. A heating element 840 formed of a heat generating resistor is buried in the ceramic heater 839, thereby improving the cutting performance.

FIG. 87E exemplifies another construction of the second holding portion 808B in the third modification (FIG. 87D) of the surgical instrument according to the sixtieth embodiment of the present invention shown in FIG. 87A. In this modification, a chamfered portion 839a, which is prepared by a C-chamfering process, is formed in the corner portion of the ceramic heater 839 of the second holding portion 808B, as shown in FIG. 87E.

FIG. 87F exemplifies still another construction of the second holding portion 808B in the third modification (FIG. 87D) of the surgical instrument according to the sixtieth embodiment of the present invention shown in FIG. 87A. In this modification, a chamfered portion 839b, which is prepared by an R-chamfering process for cutting the edge portion so as to provide an edge portion having an obtuse angle, is formed in the corner portion of the ceramic heater 839 of the second holding portion 808B.

According to the sixtieth embodiment of the present invention shown in FIG. 87A and the modifications shown in FIGS. 87B to 87F, a substantially linear contact with the living tissue can be achieved as in the fifty-ninth embodiment, leading to an excellent cutting performance. As a result, the living tissue can be cut with a small holding force between the first and second holding portions 808A and 808B. It follows that the present invention provides a thermocoagulation cutting forceps, which permits the operations ranging between the coagulation and the cutting to be performed by a series of continuous operations and which is excellent in the cutting performance of the living tissue.

FIG. 88 shows a sixty-first embodiment of the present invention. A scissors-type thermocoagulation cutting forces 841 is used in this embodiment. Two scissors components 843, 844 are mounted to a main body 842 of the thermocoagulation cutting forceps 841. These scissors components 843, 844 are overlapped one upon the other such that these scissors components are allowed to substantially cross each other in the intermediate portions. Further, a pivotal pin 845 for rotatably joining these scissors components 843, 844 is arranged in the crossing portion of these scissors components 843 and 844.

A treatment portion 848 provided with a pair of jaws 846, 847, which can be opened and closed so as to act as a holding portion of the living tissue, are arranged in the distal end portion of the main body 842. Further, substantially elliptical finger-inserting rings 849, 850 provided with ratchets 849a, 850a, are formed in the proximal end portions of the scissors components 843, 844, respectively. These finger-inserting rings 849 and 850 collectively form a manual operation portion 851 for opening or closing the pair of jaws 846 and 847.

A bent portion 852, which is moderately bent to form a substantially arcuate configuration, is formed in the treatment portion 848 of the main body 842. Further, a saw tooth-shaped slip preventing portion 847a is formed on the inner surface one jaw 847. Also, a columnar ceramic heater 846a having a heating element buried therein is formed on the inner surface of the other jaw 846, i.e., on the surface that is brought into contact with the living tissue. The heating element buried in the ceramic heater 846 serves to coagulate the living tissue. The ceramic heater 846a is connected to the connector 853 through the scissors component 843, and the cable 854 connected to the power source apparatus (not shown) is connected to the connector 853.

The operation of the thermocoagulation cutting forceps 841 of the construction described above will now be described. In the first step, the forceps 841 is inserted into the portion to be treated including, for example, a blood vessel, with the treatment portion 848 at the distal end portion of the main body 842 closed. Then, the pair of jaws 846, 847 are opened so as to peel the treated portion such as a blood vessel from the living tissue and expose the peeled treated portion.

In the next step, the peeled blood vessel or the like is compressed and held between the jaws 846 and 847 with a relatively small appropriate compressing force adapted for the coagulation treatment. If the power source apparatus (not shown) is turned on under this condition, an electric current denoted by f2 in FIG. 86 is supplied from the power source apparatus to the heating element of the ceramic heater 846a of the jaw 847 through the cable 854. The ceramic heater 846a generates heat because of the electrical resistance during the current supply so as to coagulate the living tissue of the treated portion such as the blood vessel, which is in contact with the surface of the ceramic heater 846a.

When the coagulated portion is cut open in the subsequent step, the current denoted by f3 in FIG. 86 is supplied through the cable 854 to the heating element of the ceramic heater 846a arranged in the jaw 846. If the jaws 846 and 847 are further closed under this condition, the coagulated portion of the living tissue is cut open.

According to the embodiment described above, the columnar ceramic heater 846a is mounted to the inner surface of the jaw 846 of one scissors component 843, i.e., to the contact surface with the living tissue. Also, since the contact surface of the jaw 846 with the living tissue is formed of the columnar ceramic heater 846a, the columnar ceramic heater 846a is brought into a substantially linear contact with the living tissue, leading to an excellent cutting performance. It follows that the living tissue can be cut open with a small holding force of the jaws 846 and 847, as in the fifty-ninth embodiment.

FIGS. 89A to 89C collectively show a sixty-second embodiment of the present invention, wherein FIG. 89A is a side view showing the entire construction of a scissors type coagulation treatment apparatus, FIG. 89B is a plan view showing the treatment portion, and FIG. 89C is a perspective view of the jaw. Two scissors components 863, 864 are mounted to a main body 862 of a coagulation treatment apparatus 861 according to the sixty-second embodiment of the present invention. These scissors components 863, 864 are overlapped one upon the other such that these scissors components are allowed to substantially cross each other in the intermediate portions. Further, a pivotal pin 865 for rotatably joining these scissors components 863, 864 is arranged in the crossing portion of these scissors components 863 and 864.

A treatment portion 868 provided with a pair of jaws 866, 867, which can be opened and closed so as to act as a holding portion of the living tissue, are arranged in the distal end portion of the main body 862. Further, substantially elliptical finger-inserting rings 869, 870 are formed in the proximal end portions of the scissors components 863, 864, respectively. These finger-inserting rings 869 and 870 collectively form a manual operation portion 871 for opening or closing the pair of jaws 866 and 867.

A bent portion 872, which is moderately bent to form a substantially arcuate configuration, is formed in the treatment portion 868 of the main body 862. Further, rectangular ceramic heaters 873, 874 each having a large contact area with the living tissue and serving to coagulate the living tissue are arranged on the contact surfaces of the jaws 866, 867 with the living tissue on the rear sides of the jaws 866, 867.

Each of these ceramic heaters 873 and 874 is formed by burying a heating element in a ceramic material, which is an insulating material. Teflon coating is applied to the outer surface, which is brought into contact with the living tissue, of each of the ceramic heaters 873 and 874 so as to prevent the baking (or attachment) of the living body to the outer surface of each of the ceramic heaters 873 and 874.

Further, holding portions 875, 876 for holding the living tissue are mounted on the side of the distal end of the jaws 866 and 867, respectively. As shown in FIG. 89C, saw tooth-shaped slip preventing portions 875a, 876a are mounted to these holding portions 875a, 876a.

Insulated lead wires 877, 878 are arranged in the scissors component members 863, 864, respectively, as shown in FIG. 89A. It should be noted that the distal end of the insulated lead wire 877 on the side of the scissors component member 863 is connected to the ceramic heater 873. Likewise, the distal end of the insulated lead wire 878 on the side of the other scissors component 864 is connected to the ceramic heater 674.

A cord connecting portion 879 is mounted on the outer circumferential surface of the finger-inserting ring 869 on the side of the scissors component 863. Likewise, another code connection portion 880 is mounted on the outer circumferential surface of the finger-inserting ring 870 on the side of the scissors component 864. The proximal end portion of the insulated lead wire 877 is connected to the cord connecting portion 879 on the side of the scissors component 863. Also, the insulated lead wire 878 is connected to the cord connecting portion 880 on the side of the scissors component 864. Further, connecting cords 881, 882 having one end portions connected to a power source apparatus (not shown) are detachably connected to these cord connecting portions 879, 880. It should be noted that an electric current is supplied from the power source apparatus (not shown) to the ceramic heaters 873, 874 through the current paths noted above.

The operation of the coagulation treatment apparatus of the construction described above will now be described. In the first step, the forceps is inserted into the portion to be treated including, for example, a blood vessel, with the treatment portion 868 at the distal end portion of coagulation treatment apparatus 861 closed. Then, the pair of jaws 866, 867 are opened so as to peel the treated portion such as a blood vessel from the living tissue and expose the peeled treated portion.

In the next step, the peeled blood vessel or the like is held by the holding portions 875, 876 positioned forward of the treating portion 868 so as to withdraw the held blood vessel or the like toward the proximal end. Then, the blood vessel or the like is held between and compressed by the jaws 866, 867 of the coagulation treatment apparatus with an appropriate pressurizing force adapted for the coagulation treatment. If the power source apparatus (not shown) is turned on under this condition, an electric current is supplied to the heating elements of the ceramic heaters 873, 874 of the jaws 866, 867 through the current path formed of the connection cords 881, 882, etc. The heating element is caused to generate heat by the electric resistance of the heating element during flow of the current, with the result that the living tissue of the portion to be treated such as the blood vessel, which is in contact with the surface of each of the ceramic heaters 873, 874, is coagulated. It should be noted that, since the ceramic heaters 873, 874 are insulators, the current flowing through the heating element does not leak into the living tissue of the portion to be treated.

In this embodiment, the ceramic heaters 873, 874 are arranged in the jaws 866, 867 of the main body 862. It should be noted that the ceramic heaters 873, 874 themselves, which are brought into direct contact with the living tissue of the portion to be treated such as the blood vessel, are insulators, making it unnecessary to cover the ceramic heaters 873, 874 of the jaws 866, 867 with an additional insulating material. It follows that it is possible to improve the durability and the reliability of the coagulation treatment apparatus 861.

FIGS. 90 and 91 collectively show a sixty-third embodiment of the present invention. The sixty-third embodiment is substantially equal to the fifty-ninth embodiment shown in FIGS. 81 to 86, except that, in the sixty-third embodiment, a distal end treatment portion 807 of a coagulation treatment apparatus 801 capable of insertion into a body cavity like an endoscope is modified to be constructed like the treatment portion 868 included in the sixty-second embodiment shown in FIGS. 89A to 89C.

It follows that, in the sixty-third embodiment, the treatment portion 868 of the coagulation treatment apparatus 801 constructed to be capable of insertion into a body cavity like an endoscope permits producing an effect similar to that produced by the sixty-second embodiment.

FIGS. 92 and 93 collectively show a sixty-fourth embodiment of the present invention. In the sixty-fourth embodiment, a housing case 890 for housing the coagulation treatment apparatus 861 of the sixty-second embodiment shown in FIGS. 89A to 89C is arranged as shown in FIG. 92. The housing case 890 is formed of a material having a high thermal conductivity such as a aluminum material having an anodizing treatment applied thereto. A substantially V-shaped housing groove 891 for housing the distal end portion of the main body 862 including the treatment portion 868 of the coagulation treatment apparatus 861 is formed in the housing case 890. A lever-like holding member 892 for holding the treatment portion 868 of the coagulation treatment portion 861 in a manner to prevent the treatment portion 868 from being withdrawn is arranged on the side of the distal end of the housing groove 891. Further, a fixing band 893 is mounted to the housing case 890.

When a surgery is performed, the housing case 890 is disposed on a sterilized cloth 894 covering the body of a patient, as shown in FIG. 93. Under this condition, the fixing band 893 is fixed to the sterilized cloth 894 by using a forceps 895 so as to fix the housing case 890 without fail.

The treatment portion 868 of the coagulation treatment apparatus 861 used for the surgery is heated to a high temperature. However, since the main body 862 including the treatment portion 868 of the coagulation treatment apparatus 861 is disposed in the groove 891 of the housing case 890, the heat of the treatment portion 868 is conducted to the housing case 890, with the result that the treatment portion 868 is cooled in a short time. It follows that a high safety can be ensured. In addition, the temperature can be controlled accurately when the coagulation treatment apparatus 861 is used again.

FIGS. 94 to 96 collectively show a sixty-fifth embodiment of the present invention, wherein FIG. 94 is a side view showing the entire structure of an ultrasonic coagulation cutting instrument, FIG. 95 is a perspective view of the treatment portion, and FIG. 96 is a cross sectional view showing the state that the treatment portion is closed.

As shown in FIG. 94, a slender inserting portion 902 is formed in a main body 901 of an ultrasonic coagulating cutting instrument 900. A rotatable jaw 903 is mounted to the distal end portion of the inserting portion 902. As shown in FIG. 95, a saw tooth-like slip preventing portion 905 is formed on the lower surface of the jaw 903.

Also, a manual operating portion 904 is joined to the proximal end portion of the inserting portion 902. The jaw 903 can be rotated by the manual operation portion 904.

Further, a probe 906 is inserted movable in the axial direction into the inserting portion 902. The proximal end portion of the probe 906 is joined to an ultrasonic oscillator 907 mounted to the main body 901. The probe 906 is vibrated in the axial direction by the ultrasonic oscillator 907.

As shown in FIG. 96, a plurality of projecting stripes 908 are arranged a predetermined distance apart from each other in the circumferential direction in the distal end portion of the probe 906. These projecting stripes 908 extend in parallel to the vibrating direction. Further, recessed stripes 909 are formed between adjacent projecting stripes 908. When the jaws 903 are closed so as to hold a living tissue, the projecting stripes 908 of the probe 906 are brought into contact with the living tissue, and the recessed stripes 909 are not brought into contact with the living tissue.

It follows that, when the ultrasonic coagulation cutting instrument 900 is used, the jaw 903 is closed so as to hold the living tissue between the jaw 903 and the probe 906. If the probe 906 is subjected to an ultrasonic vibration under this state, the living tissue is coagulated by the heat generated by the ultrasonic vibration. Then, when the jaw 903 is further closed, the coagulated portion is brought into a linear contact with the projecting stripes 908 of the probe 906 so as to cut the living tissue open.

If the ultrasonic vibration of the ultrasonic oscillator 907 is stopped in the subsequent step, the temperature of the probe 906 is rapidly lowered because the projecting stripes 908 and the recessed stripes 909 have a large heat dissipating area. It follows that a high safety can be ensured. In addition, the temperature can be controlled accurately when the coagulation treatment apparatus 861 is used again.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A medical treatment instrument used for coagulating and cutting a patient's body tissue, the medical treatment instrument comprising:
   a treatment portion, which is arranged at a tip of the treatment instrument, and which comprises a grasp portion including a pair of grasp members, which are openable and closeable with respect to each other, for grasping the patient's body tissue;
   an operating portion which is arranged at a proximal end of the treatment instrument, and which is operable to open and close the pair of grasp members;
   a heat generating portion which is provided at a first grasp member of the pair of grasp members, and which generates heat in accordance with current supplied thereto; and
   a cutting member which is disposed at the first grasp portion in contact with the heat generating portion and projecting toward a second grasp member of the pair of grasp members, and which is heated by the heat generating portion to cut the patient's body tissue grasped between the grasp members;
   wherein the cutting member is shaped so as to be capable of cutting the patient's body tissue only when the heat generating portion is activated.

2. The treatment instrument according to claim 1, wherein the treatment instrument comprises a surgical operation instrument adapted for use in an endoscopy operation;
   wherein the surgical operation instrument comprises an insert portion to be inserted into the patient's body;
   wherein the treatment portion is disposed at a distal end of the insert portion; and
   wherein the operating portion is disposed at the proximal end of the insert portion.

3. The treatment instrument according to claim 1, wherein each of the grasp members comprises a curved portion that is curved substantially in an arc shape.

4. The treatment instrument according to claim 1, wherein the heat generating portion is connected to temperature control means for controlling a heating temperature.

5. The treatment instrument according to claim 1, wherein the heat generating portion is provided at only the first grasp member.

6. The treatment instrument according to claim 1,
   wherein the cutting portion comprises a heat treatment protrusion portion which protrudes from the first grasp member toward a second grasp member of the pair of grasp members, and wherein a receiving portion is provided at the second grasp member to receive the heat treatment protrusion portion.

7. The treatment instrument according to claim 1,
   wherein the heat generating portion comprises an insulation material.

8. The treatment instrument according to claim 7, wherein the heater portion comprises a ceramic heater having a heat transmitting portion made of ceramic and a heating element provided in the heat transmitting portion.

9. A coagulating/cutting system comprising:
   a medical instrument used to coagulate and incise a living tissue; and
   a control element for controlling operation of the medical instrument,
   wherein the medical instrument comprises:
      a first engaging portion comprisinci a protrusion having a first engaging surface;
      a second engaging portion having a second engaging surface which is adapted to cooperate with the first engaging surface to hold the living tissue;
      a holding drive element which is operable to move the first and second engaging portions toward and away from each other to hold the living tissue; and
      a heating unit which is provided in the first engaging portion in contact with the protrusion, and which heats the protrusion when energized;
   wherein the control element comprises:
      a current supply element for supplying current to the heating unit;
      a first setting element for adjusting the current supply element to set a temperature of the heating unit to a temperature at which the living tissue is coagulated when the living tissue is held between the first and second engaging surfaces; and
      a second setting element for adjusting the current supply element to set a temperature of the heating unit to a temperature at which the living tissue is incised when the living tissue is held between the first and second engaging surfaces; and
   wherein the first engaging surface is shaped such that the medical instrument is only capable of incising the living tissue when the temperature of the heating unit is set to the temperature at which the living tissue is incised.

10. A coagulating/cutting system according to claim 9, wherein said control element further comprises a set state changing element capable of changing a set state of the current supply element set by at least one of the first and second setting elements.

11. A coagulating/cutting system according to claim 9, wherein said control element includes a first switch for driving the current supply element set by the first setting element and a second switch for driving the current supply element set by the second setting element.

12. A coagulating/cutting instrument used to coagulate and incise a living tissue, comprising:
   a first engaging portion comprising a protrusion having a first engaging surface;
   a second engaging portion having a second engaging surface which is adapted to cooperate with the first engaging surface to hold the living tissue;
   a holding drive element which is operable to move the first and second engaging portions to hold the living tissue, and
   a heating unit which is provided in the first engaging portion in contact with the protrusion and which heats the protrusion when energized;
   wherein the first engaging surface is shaped such that the coagulating/cutting instrument is capable of incising the living tissue held between the first and second engaging portions only when the protrusion is heated by the heating unit.

13. A coagulating/cutting instrument according to claim 12, wherein the first engaging surface comprises an elongate flat surface opposed to the second engaging surface.

14. A coagulating/cutting instrument according to claim 12, wherein the first engaging surface comprises an elongate curved surface curved in a shape of a substantially circular arc.

15. A coagulating/cutting instrument according to claim 12, wherein said second engaging portion includes a receiving member formed of a resin.

16. A coagulating/cutting instrument according to claim 15, wherein said resin comprises a flexible material.

17. A coagulating/cutting instrument according to claim 12, wherein said second engaging portion includes a receiving member formed of rubber.

18. A coagulating/cutting instrument according to claim 12, wherein said second engaging portion includes a receiving member formed of gel.

19. A coagulating/cutting instrument according to claim 12, wherein said second engaging portion includes a receiving member formed of fluoroplastic.

20. A coagulating/cutting instrument according to claim 15, wherein said receiving member has a groove at a portion thereof in contact with the first engaging surface.

21. A surgical instrument, comprising:
a distal end portion including a pair of holding portions for holding a living tissue, each of said holding portions having a contact surface that is adapted to be brought into contact with said living tissue; and
a manual operating portion for opening and closing said holding portions;
wherein a first holding portion of said pair of holding portions comprises a heat generating portion which generates heat, and a protrusion which comprises the contact surface of the first holding portion and which is in contact with the heat generating portion to be heated by the heat generating portion; and
wherein the contact surface of the first holding portion has a contact area with the living tissue that is smaller than a contact area with the living tissue of the contact surface of a second holding portion of the pair of holding portions that does not include the heat generating portion, and the protrusion is shaped such that the surgical instrument is capable of incising the living tissue only when the protrusion is heated by the heat generating portion.

22. The surgical instrument according to claim 21, wherein the contact surface of the first holding portion is arcuate in cross section.

23. The surgical instrument according to claim 21, wherein the contact surface of the second holding portion, which is arranged to face the contact surface of the first holding portion, is formed of a heat insulating material.

24. The surgical instrument according to claim 21, wherein said holding portions are curved from a distal end toward a proximal end thereof.

25. The surgical instrument according to claim 21, wherein the contact surface of the second holding portion, which is arranged to face the contact surface of the first holding portion, comprises a slip preventing portion.

26. The surgical instrument according to claim 21, wherein a coating for preventing sticking of heated living tissue is applied to an outer surface of said first holding portion.

27. The surgical instrument according to claim 21, wherein the contact surface of the second holding portion, which is arranged to face the contact surface of the first holding portion, comprises a second heat generating portion that is rectangular in cross section.

28. The surgical instrument according to claim 21, wherein the second holding portion, which is arranged to face the contact surface of the first holding portion, comprises a chamfered portion in which both edge portions of the contact surface are cut to form an obtuse angle.

29. The surgical instrument according to claim 21, wherein the contact surface of the second holding portion, which is arranged to face the contact surface of the first holding portion, comprises a flexible heat insulating material.

* * * * *